(12) United States Patent
　　　Jury et al.

(10) Patent No.:　US 12,678,302 B2
(45) Date of Patent:　　Jul. 14, 2026

(54) AUTOMATED HAND

(71) Applicant: Taska Prosthetics Limited, Riccarton (NZ)

(72) Inventors: Mathew James Jury, Maungaraki (NZ); David Neil Lovegrove, Huntsbury (NZ); Ross Hughan Dawson, Addington (NZ); Oliver Charles Graham Jackson-Hill, Beckenham (NZ); Darryl John Best, Governors Bay (NZ); Jonathan David Lowy, Beach Haven (NZ)

(73) Assignee: Taska Prosthetics Limited, Christchurch (NZ)

( * ) Notice: Subject to any disclaimer, the term of this patent is extended or adjusted under 35 U.S.C. 154(b) by 0 days.

(21) Appl. No.: 18/935,147

(22) Filed: Nov. 1, 2024

(65) Prior Publication Data

US 2025/0057670 A1　　Feb. 20, 2025

Related U.S. Application Data

(63) Continuation of application No. 18/802,703, filed on Aug. 13, 2024, which is a continuation of application
(Continued)

(30) Foreign Application Priority Data

Jul. 12, 2016　(NZ) ........................................ 722088

(51) Int. Cl.
　　*A61F 2/72*　　　　(2006.01)
　　*A61F 2/54*　　　　(2006.01)
(Continued)

(52) U.S. Cl.
　　CPC .............. *A61F 2/586* (2013.01); *A61F 2/583* (2013.01); *A61F 2/72* (2013.01); *A61L 27/04* (2013.01);
(Continued)

(58) Field of Classification Search
　　CPC ................................................. A61F 2002/769
　　See application file for complete search history.

(56) References Cited

U.S. PATENT DOCUMENTS 2,182,627 A　　12/1939　Cowper
2,457,316 A　　12/1948　Northrop et al.
(Continued)

FOREIGN PATENT DOCUMENTS

CN　　　100439048 C　　12/2008
CN　　　101346107 A　　1/2009
(Continued)

OTHER PUBLICATIONS

International Search Report for PCT/NZ2013/000140 (Dec. 6, 2013).
(Continued)

*Primary Examiner* — David H Willse
(74) *Attorney, Agent, or Firm* — Fish & Richardson P.C.

(57) ABSTRACT

The invention relates to an automated hand, such as a prosthetic hand. In one form, the automated hand may be fluid compatible. In one form, the automated hand may comprise features to reduce the risk of harm to motors and/or other sensitive components of the hand when subject to an impact. In one form, the hand may comprise a wrist joint configured to allow the hand to curl and flex and/or to rotate. In one form, one or more digits of the hand may be individually controlled. In one form the hand may include a thumb rotation locking mechanism. In one form the hand may be provided with removable grip plates. In one form, the hand May be configured for use as a training hand.

25 Claims, 66 Drawing Sheets

809

Related U.S. Application Data

No. 17/719,605, filed on Apr. 13, 2022, now Pat. No. 12,090,068, which is a continuation of application No. 15/783,636, filed on Oct. 13, 2017, now Pat. No. 11,351,042, which is a continuation-in-part of application No. PCT/NZ2016/050163, filed on Oct. 5, 2016, and a continuation-in-part of application No. 14/420,706, filed as application No. PCT/NZ2013/000140 on Aug. 12, 2013, now Pat. No. 9,814,604.

(60) Provisional application No. 62/237,089, filed on Oct. 5, 2015, provisional application No. 61/682,291, filed on Aug. 12, 2012.

(51) Int. Cl.

| | |
|---|---|
| *A61F 2/58* | (2006.01) |
| *A61F 2/70* | (2006.01) |
| *A61L 27/04* | (2006.01) |
| *A61L 27/16* | (2006.01) |
| *A61L 27/56* | (2006.01) |
| *B25J 15/00* | (2006.01) |
| *B25J 15/10* | (2006.01) |
| *B25J 15/12* | (2006.01) |
| *A61F 2/50* | (2006.01) |
| *A61F 2/76* | (2006.01) |

(52) U.S. Cl.
CPC ............ *A61L 27/165* (2013.01); *A61L 27/56* (2013.01); *B25J 15/0009* (2013.01); *B25J 15/10* (2013.01); *B25J 15/12* (2013.01); *A61F 2002/5003* (2013.01); *A61F 2002/5007* (2013.01); *A61F 2002/5038* (2013.01); *A61F 2002/5079* (2013.01); *A61F 2002/5089* (2013.01); *A61F 2002/587* (2013.01); *A61F 2002/701* (2013.01); *A61F 2002/704* (2013.01); *A61F 2002/769* (2013.01)

(56) References Cited

U.S. PATENT DOCUMENTS

| | | | |
|---|---|---|---|
| 2,490,172 A | 12/1949 | Gunnar | |
| 2,679,649 A | 6/1954 | Weir | |
| 2,696,010 A | 12/1954 | Robinson | |
| 3,090,049 A | 5/1963 | Lyvin | |
| 3,413,658 A | 12/1968 | Becker | |
| 3,694,021 A | 9/1972 | Mullen | |
| 4,087,730 A | 5/1978 | Goles | |
| 4,364,593 A | 12/1982 | Maeda | |
| 4,685,928 A | 8/1987 | Yaeger | |
| 5,040,643 A | 8/1991 | Chapman et al. | |
| 5,336,289 A | 8/1994 | Yeom et al. | |
| 5,413,611 A | 5/1995 | Haslam, II et al. | |
| 5,888,246 A | 3/1999 | Gow | |
| 5,967,580 A | 10/1999 | Ross | |
| 6,244,644 B1 | 6/2001 | Lovchik et al. | |
| 6,423,099 B1 | 7/2002 | Iversen et al. | |
| 7,041,141 B2 | 5/2006 | Iversen et al. | |
| 7,914,587 B2 | 3/2011 | Archer et al. | |
| 8,257,446 B2 | 9/2012 | Puchhammer | |
| 8,343,234 B2 | 1/2013 | Puchhammer | |
| 8,579,991 B2 | 11/2013 | Puchhammer | |
| 8,585,775 B2 | 11/2013 | Hirota et al. | |
| 8,690,963 B2 | 4/2014 | Puchhammer | |
| 8,696,763 B2 | 4/2014 | Gill | |
| 8,808,397 B2 | 8/2014 | Gow | |
| 8,979,943 B2 | 3/2015 | Evans et al. | |
| 8,986,395 B2 | 3/2015 | McLeary | |
| 8,999,003 B2 | 4/2015 | Wenstrand et al. | |
| 9,101,499 B2 | 8/2015 | Haggas | |
| 9,539,118 B2 * | 1/2017 | Leuthardt | A61B 5/372 |
| 9,572,688 B2 | 2/2017 | Puchhammer et al. | |
| 9,724,211 B1 * | 8/2017 | Snell | A61F 2/60 |
| 9,814,604 B2 | 11/2017 | Jury | |
| 11,351,042 B2 | 6/2022 | Jury et al. | |
| 2004/0015240 A1 | 1/2004 | Archer et al. | |
| 2004/0034436 A1 * | 2/2004 | Einarsson | A61F 2/54 |
| | | | 623/24 |
| 2004/0103740 A1 | 6/2004 | Townsend et al. | |
| 2005/0006915 A1 | 1/2005 | Matsuda | |
| 2007/0040400 A1 | 2/2007 | Greenhill et al. | |
| 2007/0260328 A1 | 11/2007 | Bertels et al. | |
| 2008/0058668 A1 | 3/2008 | Seyed Momen et al. | |
| 2008/0188952 A1 | 8/2008 | Veatch et al. | |
| 2008/0269907 A1 | 10/2008 | Puchhammer | |
| 2009/0145254 A1 | 6/2009 | Hirabayashi et al. | |
| 2010/0176615 A1 | 7/2010 | Okuda et al. | |
| 2010/0198362 A1 | 8/2010 | Puchhammer | |
| 2010/0259057 A1 | 10/2010 | Madhani | |
| 2010/0318194 A1 | 12/2010 | Puchhammer et al. | |
| 2011/0144770 A1 | 6/2011 | Moyer et al. | |
| 2011/0257765 A1 | 10/2011 | Evans et al. | |
| 2012/0000304 A1 | 1/2012 | Hamminga et al. | |
| 2012/0109337 A1 * | 5/2012 | Schulz | A61F 2/586 |
| | | | 623/64 |
| 2012/0150321 A1 * | 6/2012 | Goldfarb | B25J 9/1612 |
| | | | 623/57 |
| 2012/0150322 A1 | 6/2012 | Goldfarb et al. | |
| 2013/0175816 A1 | 7/2013 | Kawasaki et al. | |
| 2013/0340560 A1 | 12/2013 | Burridge et al. | |
| 2015/0182353 A1 | 7/2015 | Evans et al. | |
| 2015/0216679 A1 | 8/2015 | Lipsey et al. | |
| 2015/0216680 A1 | 8/2015 | Lipsey et al. | |
| 2015/0230941 A1 | 8/2015 | Jury | |
| 2018/0133028 A1 | 5/2018 | Poirters | |

FOREIGN PATENT DOCUMENTS

| | | | |
|---|---|---|---|
| CN | 201572217 U | 9/2010 | |
| CN | 201640540 U | 11/2010 | |
| CN | 102806563 A | 12/2012 | |
| CN | 202572400 U | 12/2012 | |
| CN | 204274729 U | 4/2015 | |
| DE | 746023 C | 5/1944 | |
| DE | 1908364 A1 | 11/1970 | |
| EP | 1457294 B1 | 11/2008 | |
| EP | 1977865 B1 | 10/2010 | |
| FR | 1 604 289 A | 10/1971 | |
| FR | 2 236 478 A1 | 2/1975 | |
| FR | 2 277 569 A2 | 2/1976 | |
| GB | 151758 A | 10/1920 | |
| JP | S 64-015043 A | 1/1989 | |
| JP | H04-501682 A | 3/1992 | |
| JP | H5-51319 U | 7/1993 | |
| JP | H10-314198 A | 12/1998 | |
| JP | 2001-519197 A | 10/2001 | |
| JP | 2001-166676 A | 12/2002 | |
| JP | 2003-266357 A | 9/2003 | |
| JP | 2004-514006 A | 5/2004 | |
| JP | 2008-032140 A | 2/2008 | |
| JP | 2008-212652 A | 9/2008 | |
| JP | 2009-519794 A | 5/2009 | |
| JP | 2009-520525 A | 5/2009 | |
| JP | 2012-107360 A | 6/2012 | |
| JP | 2012-192496 A | 10/2012 | |
| JP | 2013-039656 A | 2/2013 | |
| JP | 2013-094891 A | 5/2013 | |
| JP | 2016-043425 A | 4/2016 | |
| JP | 2018-519868 A | 7/2018 | |
| KR | 101201455 B1 | 11/2012 | |
| RU | 1 811 823 C | 4/1993 | |
| SU | 1 616 650 A1 | 12/1990 | |
| WO | 90/02030 A1 | 3/1990 | |
| WO | 99/18875 A1 | 4/1999 | |
| WO | WO 02/49534 A2 * | 6/2002 | A61F 2/72 |
| WO | 02/058896 A1 | 8/2002 | |
| WO | WO 2009/015751 A1 | 2/2009 | |
| WO | 2010/018358 A2 | 2/2010 | |
| WO | 2010/051798 A1 | 5/2010 | |
| WO | 2011/036626 A2 | 3/2011 | |
| WO | 2012/039479 A1 | 3/2012 | |

(56)        References Cited

FOREIGN PATENT DOCUMENTS

| WO | | 2012/140400 | A1 | 10/2012 |
|----|----|----|----|----|
| WO | | 2013/012029 | A1 | 1/2013 |
| WO | WO | 2013/012542 | A1 | 1/2013 |
| WO | | 2013/038187 | A1 | 3/2013 |
| WO | | 2013/138912 | A1 | 9/2013 |
| WO | | 2014/027897 | A1 | 2/2014 |
| WO | WO | 2014/032802 | A1 | 3/2014 |
| WO | | 2014/111843 | A2 | 7/2014 |
| WO | WO | 2014/122455 | A1 | 8/2014 |
| WO | | 2015/110521 | A1 | 7/2015 |
| WO | | 2015/110522 | A1 | 7/2015 |
| WO | | 2024/184815 | A1 | 9/2024 |

OTHER PUBLICATIONS

International Search Report for PCT/NZ2016/050163 (Feb. 16, 2017).
Examination Report for Indian Patent Application No. 201817012348 (Oct. 20, 2021 ).
European Search Report for EP Application No. 1685397.2 (Apr. 3, 2019).
Search Report for European Patent Application No. 21202594.4 (Feb. 28, 2022).
Koslow, Tyler., "e-NABLE Volunteer Puts Light Gaming Right into our 3D Printed Hands," 3D Printing Industry, <URL=https://3dprintingindustry.com/news/e-nable-volunteer-puts-light-entertainment-right-into-our-3d-printed-hands-56450/> (Aug. 27, 2015), retrieved on Dec. 19, 2024, 3 pages.
Screenshot from Jury, Matthew., "Check out Brydens Latest Video At https://www.pledgeme.co.nz/697," Power-on indicator LED shown on back of hand at 2:06, <URL=https://www.youtube.com/watch?v=DIQ2eQhaB5w> (Apr. 9, 2011), retrieved on Dec. 19, 2024, 1 page.
Schmitz et al., "Touch Sensors for Humanoid Hands" IEEE Xplore, DOI: 10.1109/ROMAN.2010.5598609 (Oct. 2010), 7 pages.
Screenshot from movie "Iron Man,"—showing light on artificial glove/gauntlet, Marvel Studios (Apr. 14, 2008), 1 page.
MEC '11 Raising the Standard—University of New Brunswick's International Conference on Advanced Limb Prosthetics, Aug. 14-19, 2011, 317 pages.
Spadafora, F. et al., "Design and Construction of a Robot Hand Prototype for Underwater Applications", Science Direct, Design and Construction of a Robot Hand Prototype for Underwater Applications, IFAC-PapersOnLine 48-2: 294-299 (2015).
Communication of a Notice of Opposition for European Patent Application No. 21202594.4 from Vincent Ssystems GmbH with English translation 166 pages, Nov. 25, 2024.
Communication of a Notice of Opposition for European Patent Application No. 21202594.4 from Ossur Iceland ehf (Nov. 20, 2024) 32 pages.
Henson, Arm Dynamics, Introduction to the TASKA and the TASKA CX, available on the internet at https://www.armdynamics.com/upper-limblibrary/ introduction-to-the-taskaand-the-taska-cx (May 28, 2024) D27, 9 pages.
Screenshot from Engineering New Zealand, "The World's First Water-Resistant Prosthetic Hand", available on the internet at https://www.youtube.com/watch?v=ihGkVH09-4c (Feb. 11, 2020) D24, 1 page.
Kenny, Stuff, We got it made: World's first waterproof prosthetic hand, available on the internet at https://www.stuff.co.nz/business/118682971/weqot-it-made-worldsfirst-waterproof-prosthetic-hand (Jan. 21, 2020) D26, 5 pages.
Bhat et al., The compound Taguchi and grey relational analysis used to optimize the tribological parameters of worm gear under wet condition, Elsevier Journal, https://doi.org/10.1016/i.matpr.2021.05.248 (Jun. 3, 2021) D30, 4 pages.
Schweitzer, Car wash -what happens when one uses an ilimb Ultra Revolution *just* to assist holding the water tube [glove damage within minutes]—Technical Right Below Elbow Amputee Issues, https://www.swisswuff.ch/tech/?p=2965 (May 3, 2014) D15, 9 pages.
Cordelia et al, Literature Review on Needs of Upper Limb Prosthesis Users. Front Neuroscience 10:209. doi: 10.3389/fnins.2016.00209. PMID: 27242413; PMCID: PMC4864250 (May 12, 2016) D18, 47 pages.
Einfeldt et al, What do users and their aiding professionals want from future devices in upper limb prosthetics? A focus group study. PLoS One 18(12):e0295516, https://doi.org/10.1371/journal.pone.0295516 (Dec. 29, 2023) D17, 14 pages.
Ever-Power Industry, Are Stainless Steel Worm Gearboxes Suitable for Use in Wet Conditions?, available on the internet at https://www.ever-power.net/arestai nless-steel-wo (retreived Mar. 24, 2025) D31, 4 pages.
Fillauer, MC Standard Hand Prosthetist Manual (2021) D21, 8 pages.
Vincent Systems, VINCENTevolution4, available on the inter, Dnet at https://www.vincentsystems.de/en/_files/ugd/e71ff6_5cca9fcfad0941db9c9ceb252fe69277.pdf (retreived Apr. 3, 2025) D23, 2 pages.
Schweitzer, i-Limb glove self destructs (in-storage product suicide) [WTF], Technical Right Below Elbow Amputee Issues, https://www.swisswuff.ch/tech/?p=5651 (Feb. 15, 2016) D16, 9 pages.
Kerver, et al. "User-relevant factors determining prosthesis choice in persons with major unilateral upper limb defects: A meta-synthesis of qualitative literature and focus group results." PLoS ONE, vol. 15, No. 6, p. e0234342. Gale in Context: Opposing Viewpoints, dx.doi.org/10.1371/journal.pone.0234342 (Jun. 30, 2020) D19, 25 pages.
Stuff, Kiwis engineer the world's first waterproof prosthetic hand, available on the internet at https://www.stuff.co.nz/business/innovation/94370766/kiwisengineerthe-worlds-first-waterproof-prosthetic-hand (retreived Mar. 21, 2025) D25, 7 pages.
Ossur, i-limb hand user manual (Sep. 2018) D20, 28 pages.
SPS Hanger Store,TASKA CX Hand 7 1/4in, available on the internet at https://www.spshangerstore.com/taska-cx-hand-7-1-4in.html (retreived Mar. 21, 2025) D28, 4 pages.
Callaghan Innovation, Taska_ Hands across the water, available on the internet at https://www.callaghaninnovation.govt.nz/stories/hands-across-water/ (Apr. 2, 2019), 17 pages.
Waldera et al. Assessing the prosthetic needs of farmers and ranchers with amputations. Disability and Rehabilitation: Assistive Technology, 8(3), 204-212, https://doi.org/10.3109/17 4831072012699994 (Jul. 10, 2012) D14, 10 pages.
5th Element Limited, Reply to Notice of Opposition for European Patent Application No. 21202594.4 including Consolidated Citations List (Apr. 3, 2025) 30 pages.
Brief Communication—Letter from opponent 01 in European Appln. No.21202594.4, dated Jan. 15, 2026, 12 pages.
Brief Communication—Letter from opponent 02 in European Appln. No. 21202594.4, dated Jan. 21, 2026, 37 pages (with Machine Translation).
Reply to an examination report in opposition proceedings in European Appln. No. 21202594.4, dated Jan. 15, 2026, 180 pages.
Correction to the Jan. 15, 2026 reply to an examination report in opposition proceedings in European Appln. No. 21202594.4, dated Feb. 5, 2026, 161 pages.
Decision of Refusal in Japanese Appln. No. 2024-088883, dated Feb. 20, 2026, 8 pages (with English translation).
Office Action in Indian Appln. No. 202218040405, mailed on Apr. 7, 2026, 7 pages (with English translation).
Office Action in Indian Appln. No. 202218074304, mailed on Apr. 7, 2026, 7 pages (with English translation).
CIRS.UDG.edu [online], "ECA micro arm," Mar. 2026, retrieved from URL<https://cirs.udg.edu/infrastructure/robots/girona-500-auv/#eca>, 12 pages.
NGCUV IFAC Workshop, "4th International IFAC Workshop On Navigation, Guidance and Control of Underwater Vehicles," Program, 4th IFAC Workshop on Navigation, Guidance and Control of Underwater Vehicles, Apr. 28-30, 2015, 15 pages.
NGCUV IFAC Workshop, "Proceedings," 4th IFAC Workshop on Navigation, Guidance and Control of Underwater Vehicles, Apr. 28-30, 2015, 2 pages.

(56)  References Cited

OTHER PUBLICATIONS

Opposition, "Notice of Opposition," in European Appln. No. 23219504. 0, mailed on Apr. 10, 2026, 34 pages.
Opposition, "Notice of Opposition," in European Appln. No. 23219504. 0, mailed on Apr. 10, 2026, 44 pages.

* cited by examiner

100

550 510 200 100

520

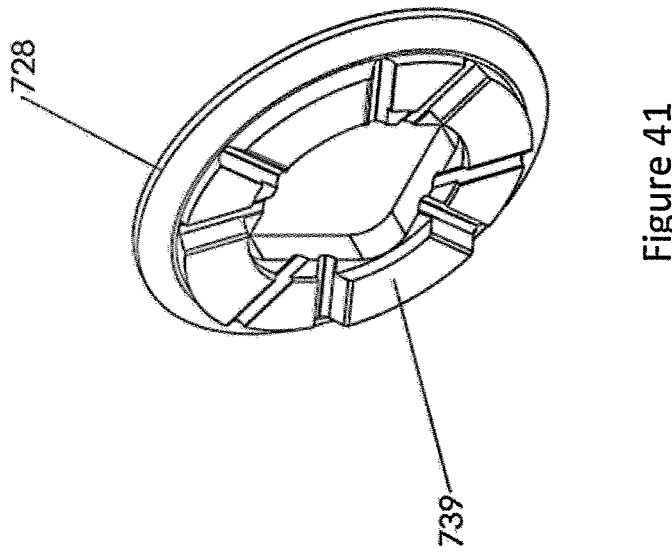
Figure 41
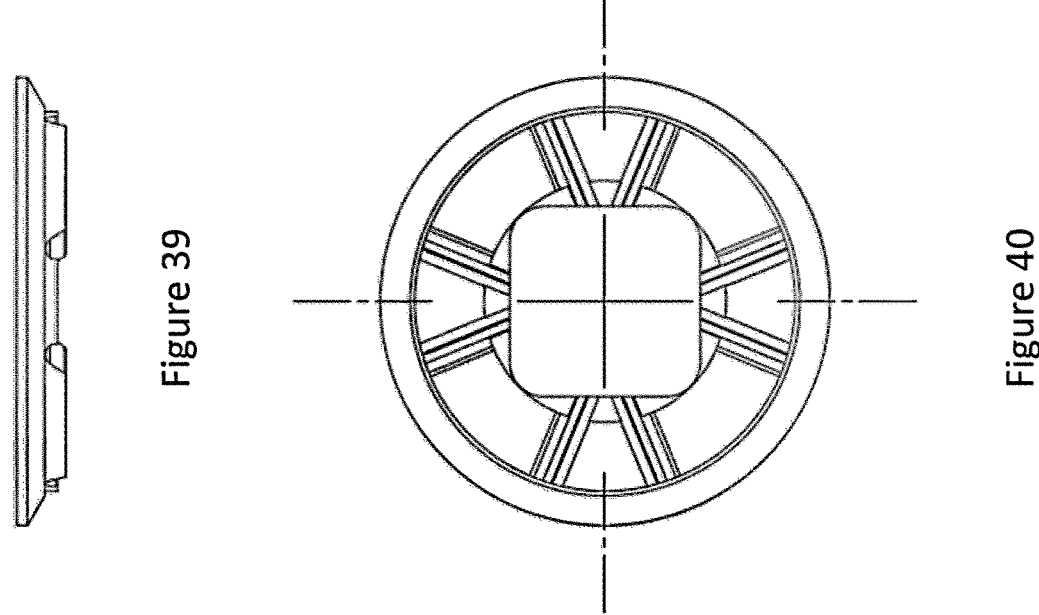
Figure 39
Figure 40

809

AUTOMATED HAND

RELATED APPLICATIONS

This application is a Continuation of U.S. patent application Ser. No. 18/802,703, filed 13 Aug. 2024, which is a Continuation of Ser. No. 17/719,605, filed 13 Apr. 2022, now U.S. Pat. No. 12,090,068, issued 17 Sep. 2024, which is a Continuation of U.S. patent application Ser. No. 15/783, 636, filed 13 Oct. 2017, now U.S. Pat. No. 11,351,042, issued 7 Jun. 2022, which is a Continuation-in-Part of PCT/NZ2016/050163, filed 5 Oct. 2016, which claims benefit of U.S. Provisional Application No. 62/237,089, filed 5 Oct. 2015 and New Zealand Patent Application No. 722088, filed 12 Jul. 2016, and which applications are incorporated herein by reference. U.S. patent application Ser. No. 15/783, 636 is also a Continuation-in-Part of U.S. patent application Ser. No. 14/420,706, filed 10 Feb. 2015, now U.S. Pat. No. 9,814,604, issued 14 Nov. 2017, which is a National Stage of PCT/NZ2013/000140, filed 12 Aug. 2013, which claims benefit of U.S. Provisional Application No. 61/682,291, filed 12 Aug. 2012, and which applications are incorporated herein by reference in their entirety.

To the extent appropriate, a claim of priority is made to each of the above disclosed applications.

TECHNICAL FIELD

The invention relates to an automated hand, such as a prosthetic hand, and components for an automated hand.

BACKGROUND OF THE INVENTION

Automated hands are commonly used as prosthetic hands, which may be used to grip objects, shake the hand of another person, and perform other tasks commonly carried out by human hands.

However, conventional automated hands have several disadvantages. Many of the hands are necessarily large and bulky to fit the working parts within the hand. This can result in the hand looking unnatural.

Conventional automated hands are typically unable to flex and curve around an object to grip the object reliably. This is particularly problematic where the object is curved or slippery, such as a drinking glass or bottle. The motors of known automated hands may also strain to provide an adequate grip and therefore wear quickly. Further, because these hands do not curve and flex, the hands can also feel unnatural in a handshake.

Because of the typically rigid nature of conventional automated hands, it is common for sensitive components of these hands, such as motors and electronics, to break under impact forces, particularly a lateral impact force where the side of the hand near the little finger is banged against a hard surface or where an outer edge of the thumb receives a lateral impact.

Another problem with known automated hands is that the hands themselves are not waterproof. Instead, a user must wear a waterproof glove over the hand to protect the sensitive working parts and electronic components of the hand.

Known automated hands commonly comprise complex finger actuation systems that comprise resistance springs to bias the fingers towards a particular position and absorb impact. When the motors of the hand drive the fingers to a non-biased position, the resistance from the springs causes the fingers to move more slowly than desired and may strain the drive motors and drain the battery power quickly. Some designs include one directional clutches to absorb impact forces but these do not protect against impacts in the opposite direction. Motors may also be provided within digits with a worm gear driving the digit relative to a stationary gear wheel. This arrangement increases the mass that must be moved when moving a digit, requires wiring along the digits and restricts the space available for linkages. Due to the confined space it is very difficult to accommodate clutch mechanisms.

The motors and working parts of known automated hands are also susceptible to damage when digits of the hands are subjected to too much tension or to an end impact. This is because the digits are typically directly connected to the motors and are unable to disengage from the motors when subjected to high forces.

Conventional automated hands may provide a wrist positioning system, but these systems are typically complex, large and cumbersome, which extends the palm away from the arm creating an extended, heavy, ungainly and unnatural looking wrist. In addition, there are limited ways in which the hand can move in relation to the wrist and the wrist is typically not fluid compatible.

Although it is known for automated hands to be used as training hands for new hand amputees, these hands do not provide an indication that EMG (electromyography) signals have been received by the user and/or which grip has been selected. Consequently, hand amputees may find it frustrating to become accustomed to the EMG algorithms needed to change the grip patterns of the hand, especially when they cannot tell which grip pattern has been selected or whether EMG signals are being received.

A significant disadvantage of known automated hands is that the working parts, especially the electronics, are sensitive to getting wet. Consequently, the naked hands cannot be used in a wet environment, such as in a bath, shower, or when washing dishes, without becoming damaged. It is only possible to use known hands in a wet environment by placing a waterproof glove over the hand. This can be frustrating for a user because it is difficult to place a glove over a prosthetic hand. The gloves may also wear and tear easily.

Grip surfaces on automated hands may also suffer from excessive wear if contact surfaces are formed of a material that is too soft and may not provide suitable grip if the material is hard wearing and formed of as hard material.

It is therefore an object of the invention to provide an automated hand that goes at least some way towards overcoming one or more of the disadvantages of the prior art, or that at least provides a useful alternative to existing automated hands.

SUMMARY OF THE INVENTION

In a first aspect there is provided an automated hand comprising a palm; one or more resiliently flexible and compressible mounts attached to the palm; and one or more connectors, each having a digit extending therefrom that is moveable relative to the palm, each connector mounted to a respective mount such that each connector may rotate about the mount when a lateral force is applied to a digit.

Each connector may rotate in the plane of the palm or in a plane normal to the plane of the palm. A single integral mount may be provided or a number of separate mounts may be provided. The mounts may suitably be formed of a material having a DMTA damping factor of between 0.05 to 0.8, preferably between 0.05 to 0.5, over a temperature range of −20° C. to 100° C. The material preferably has a resilience of between 20% to 60% and a Shore A hardness of between 10 to 90 (more preferably a Shore A hardness of between 30 to 60) or alternatively a Shore D hardness of between 40 to 90. A metacarpal brace comprising a number of mounts or a single mount with multiple apertures preferably has such resilience that at least two digits may be splayed apart by at least 5 degrees due to relative movement between the actuators and palm allowed by elastic deformation of the metacarpal brace, and preferably at least 10 degrees, and more preferably at least 20 degrees. The metacarpal brace preferably also provides impact absorbtion for forces applied to a digit in a direction normal to the palm such that each actuator may rotate by at least 2 degrees (preferably 5 degrees and more preferably 10 degrees) relative to the palm due to elastic deformation of the metacarpal brace. A force of between 2.5 and 20 Newtons applied laterally or normal to the tip of a digit preferably results in angular rotation with respect to the palm in the plane of the palm of at least 3 degrees, preferably at least 5 degrees, due to elastic deformation of the metacarpal brace.

The metacarpal brace may be formed of elastomers, rubber, silicone, compressible polymers or thermoplastics materials. Preferably the material is a thermoset elastomer (either hydrocarbon, fluorocarbon or silica-based), a thermoplastic elastomer, a thermoset rubber, an inherently soft thermoplastic. It may also be an alloy or blend or a foamed composition of any of the above polymers.

In another aspect there is provided an automated hand comprising: a palm; a resilient mount secured to the palm including a recess for receiving an actuator; and a first actuator having a proximal end and a distal end, the proximal end mounted within the recess and the distal end having a thumb extending therefrom in which the resilient mount permits relative angular displacement of the first actuator with respect to the palm of at least 2 degrees. The first actuator may rotate the thumb relative to the palm in a first plane of rotation, the hand including a first engagement surface mounted on the thumb and a second engagement surface mounted on the palm such that during a gripping movement of the thumb the actuator is displaced with respect to the palm so as to bring the engagement surfaces into contact to restrain movement in the first plane.

According to a further aspect there is provided an automated hand comprising: a palm; a first actuator having a proximal end and a distal end, the proximal end pivotally mounted to the palm and having a thumb extending therefrom, the actuator rotating the thumb relative to the palm in a first plane of rotation; and a first engagement surface mounted on the thumb and a second engagement surface mounted on the palm such that during a gripping movement of the thumb the actuator is displaced with respect to the palm so as to bring the engagement surfaces into contact to restrain movement in the first plane.

According to a further aspect there is provided an automated hand comprising: a palm; a digit extending from the palm; an actuator driving a gear wheel; and an overload protection clutch driven by the gear wheel at its input to cause the digit connected to its output to move and having bidirectional overload protection so that when the rotational force applied to the clutch exceeds a limit the clutch allows relative rotation between its input and output.

According to a further aspect there is provided an automated hand comprising: a palm; a gear wheel connected to the palm via a clutch; and a digit extending from the palm including an actuator driving a gear engaged with the gear wheel so as to cause rotation of the digit with respect to the palm, wherein the clutch is an overload protection clutch having bidirectional overload protection so that when the rotational force applied to the clutch by the gear wheel exceeds a limit the clutch allows relative rotation between the digit and the palm.

According to a further aspect there is provided an automated hand comprising: a palm; and two or more digits extending from the palm; one or more motors configured to cause at least one of the digits to move; and a wrist joint configured to connect the palm to an arm member, wherein the wrist joint comprises an axle having opposing ends that engage with the palm to allow the palm to rotate about the axle; and a locking mechanism located in the palm configured to lock the palm in a fixed position relative to an arm member.

According to a further aspect there is provided an automated hand comprising: a sealed palm region that is waterproof when submerged in fluid; two or more sealed knuckle joints mounted to the palm; two or more digits extending from respective sealed knuckle joints; and one or more actuators mounted within the sealed palm region which drive the sealed knuckle joints so as to cause the digits to move.

According to a further aspect the invention provides an automated hand comprising: a palm; two or more digits extending from the palm; and one or more drive motors configured to cause at least one of the digits to move. Each digit is attached to the palm by a connector comprising a knuckle joint and a connecting arm. The automated hand also comprises a resiliently flexible and compressible metacarpal brace extending between two or more connectors. The metacarpal brace comprises a first end, a second end, and one or more support apertures. Each support aperture is configured to hold at least a portion of a connecting arm therein.

One or more support apertures extend between the first end and second end of the metacarpal brace.

Optionally, each support aperture is substantially cylindrical and each connecting arm is substantially cylindrical and is configured to nest within a respective support aperture.

In one form, the hand comprises an anti-rotation system configured to prevent rotation of one or more digit supports within one or more support apertures of the metacarpal brace.

In one form, at least one support aperture comprises at least one stop configured to engage with a corresponding stop of the connecting arm to prevent rotation of the connecting arm within the support aperture. Preferably, the support aperture comprises at least one recess or opening configured to engage with at least one projection to hold the projection within the recess or opening.

In one form, at least one connector comprises a connecting arm, a motor housing and a knuckle joint located between the connecting arm and motor housing. The motor housing is located within one of the digits and the connecting arm is located within the palm.

Preferably, at least one connecting arm comprises a motor housing for housing a drive motor.

Optionally, the metacarpal brace is made of one or more materials of the group consisting of the following: an elastomer, rubber, silicone, a compressible polymer.

According to a further aspect, the invention provides a resiliently flexible and compressible metacarpal brace comprising a first end, a second end substantially opposite the first end, and further comprising one or more apertures extending between the first end and second end.

According to a further aspect, the invention provides an automated hand comprising: a palm; and two or more digits extending from the palm; wherein at least one digit forms a thumb mounted at or near a first side of the palm of the hand, wherein the thumb substantially opposes at least one other digit and wherein the hand comprises a compressible thumb cushion positioned in contact with a portion of the thumb. The compressible thumb cushion may be configured to dampen lateral movement of the thumb under a lateral impact and to provide grip compliance.

Preferably, the thumb is connected to a base member that extends to one side of the thumb, and the compressible thumb cushion is mounted on the base member.

Preferably, one side of the compressible thumb cushion is positioned in contact with one side of the thumb.

In one form, the thumb comprises a first motor configured to cause the thumb to curl and flex about a second axis. Preferably, the first motor is housed within the thumb.

In one form, the thumb comprises a second motor configured to cause the thumb to hinge toward and away from a second side of the palm about a first axis, the second side being substantially opposite the first side. Preferably, the second motor is housed within the base member.

The hand may also comprise a thumb support comprising a first surface, wherein the base member is configured to be located on the first surface of the thumb support. Preferably, the thumb support comprises a first surface comprising a sloping first recess configured to receive at least a portion of the base member therein and wherein the angle of the recess is inclined toward the thumb.

The first recess may comprise an opening at its deepest end.

The thumb support may further comprise a second recess and the thumb comprises a bottom surface comprising a projection extending from the bottom surface; wherein the projection is configured to be received within the second recess.

In one form, the projection and second recess are both elongate and extend in a direction substantially perpendicular to the length of the base member. Preferably, the projection and recess are both semi-cylindrical.

According to a further aspect, the invention provides an automated hand comprising: a palm; two or more digits extending from the palm; one or more motors configured to cause at least one of the digits to move; and at least one clutch device. The clutch device is configured to engage and disengage one of the motors from driving a first digit. The clutch device is also configured to engage with the first digit. The clutch device comprises a driven element comprising a contact surface and being configured to be caused to rotate by the motor. The clutch device also comprises a clamping member comprising a first surface configured to engage with the contact surface of the driven element; and a compression member configured to cause the first surface of the clamping member to press against the contact surface of the driven element.

Preferably, the contact surface of the driven element comprises one or more male engagement members and the clamping member comprises one or more female engagement members. Each male engagement member may be configured to be at least partially received in a respective female engagement member to engage the driven element and clamping member with each other.

In one form, each of the one or more female engagement members comprises a substantially concave recess. Preferably, each of the one or more male engagement members comprises a substantially convex or spherical projection.

Preferably, the contact surface of the driven element comprises one or more apertures. Each aperture comprises a closed end and is configured to receive a male engagement member at or near the contact surface, such that the male engagement member projects from the contact surface and wherein the compression member is held within the aperture between the male engagement member and the closed end of the aperture.

Preferably, the compression member is a spring held under compression.

In one form, the male engagement member is a ball, such as a ball bearing. In another form, the male engagement member may be a nib.

Preferably, the contact surface of the driven element comprises one or more female engagement members and the clamping member comprises one or more male engagement members. Each male engagement member may be configured to be at least partially received in a respective female engagement member to engage the driven element and clamping member with each other.

Preferably, each of the one or more female engagement members comprises a substantially concave recess. More preferably, each of the one or more male engagement members comprises a substantially convex or spherical projection.

In one form, the first surface of the clamping member comprises one or more apertures, wherein each aperture comprises a closed end and is configured to receive a male engagement member at or near the first surface, and wherein the compression member is held within the aperture between the male engagement member and the closed end of the aperture.

Preferably, the compression member is a spring held under compression.

In one form, the male engagement member is a ball, such as a ball bearing. In another form, the male engagement member may be a nib.

Preferably, the clamping member comprises a second surface configured to engage with the first digit.

In one form, the clamping member comprises a first element comprising the first surface of the clamping member. The clamping member also comprises a second element comprising a second surface of the clamping member. The compression member comprises a spring washer located between the first and second surfaces.

Preferably, one or more male engagement members project from the first surface of the clamping member and are configured to engage with one or more female engagement members provided on the contact surface of the driven element.

In one form, the second surface of the clamping member is configured to engage with the body of the first digit. The body of the first digit comprises an inner surface comprising a receiving element configured to receive the second surface of the clamping member therein.

Preferably, the receiving element comprises an aperture, recess, or area defined by at least one wall bordering the area or by a plurality of projecting arms.

In one form, the contact surface of the driven element is substantially circular and the clamping member comprises a body comprising two end portions and a substantially concave inner surface comprising the first surface of the clamping member and being configured to substantially surround at least half of the contact surface of the driven element. The compression member is configured to press at least one end portion of the clamping member toward the other end portion to clamp the first surface of the clamping member against the contact surface of the driven element.

In another form, the contact surface of the driven element is substantially circular and the clamping member comprises a substantially ring shaped body comprising two end portions extending from the ring shaped body. The substantially ring shaped body comprises an inner surface comprising the first surface of the clamping member and configured to substantially surround the contact surface of the driven element. The compression member is configured to press at least one end portion of the clamping member toward the other end portion to clamp the first surface of the clamping member against the contact surface of the driven element.

Preferably, the clamping member is configured to engage with the body of the first digit.

In one form, an inner surface of the body of the first digit comprises a receiving element configured to receive at least a portion of the clamping member therein. The receiving element comprises a recess shaped to key with the clamping member.

Preferably, the driven element and clamping element are supported by a common axle passing through an axle receiving aperture formed in the driven element and clamping element.

According to a further aspect, the invention provides an automated hand comprising: a palm; and two or more digits extending from the palm; one or more motors configured to cause at least one of the digits to move; and a wrist joint configured to connect the palm to an arm member. The wrist joint comprises an axle having opposing ends that engage with the palm to allow the palm to rotate about the axle.

Preferably, the positioning system further comprises a positioning member that engages with the axle and a lock configured to lock the palm in a fixed position relative to the positioning member. The lock and at least a portion of the positioning member are located within the palm of the hand.

In one form, the positioning system comprises an axle located within the palm of the hand; a positioning member comprising a locking arm located with the palm; and a locking member located within the palm. The locking member is configured to engage with the positioning member to lock the palm in a neutral position, a flexion position, or an extension position.

Preferably, the locking arm comprises a plurality of openings and the locking member comprises a locking pin configured to be received within any of the openings.

Preferably, the axle is supported within the palm by a pair of substantially compressible axle mounts.

Preferably, the wrist joint further comprises a connector configured to attach to the positioning member and to attach to the arm member.

Preferably, the positioning member is configured to rotate relative to the connector.

In one form, the positioning member comprises at least one locking finger and the connector comprises a series of indexing nodules configured to engage with the locking finger(s) to lock the positioning member in position relative to the connector. The at least one locking finger is configured to disengage from the indexing nodules when the positioning member is caused to rotate relative to the connector.

Preferably, the wrist joint further comprises a watertight seal located between the positioning member and the connector.

According to a further aspect, the invention provides a wrist joint for an electric terminal device, wherein the wrist joint is configured to attach to the electric terminal device and to an arm member and wherein the wrist joint comprises a body comprising a first end and a second end, the second end being configured to face toward the arm member and comprising an aperture extending into a substantially hollow region of the wrist joint body to allow a portion of a user's stump to extend through at least a portion of the wrist joint.

Preferably, the aperture extends between the first and second ends of the wrist joint.

In one form, the wrist joint further comprises an axle that is rotatably attached to the palm to allow the palm to hinge relative to the wrist joint.

Preferably, the electric terminal device comprises a powered hook.

Alternatively, the electric terminal device comprises an automated hand.

According to a further aspect, the invention provides an automated hand comprising: a palm; two or more digits extending from the palm; one or more motors configured to cause the digits to move; and a control system connected to the one or more motors and configured to receive: one or more EMG signals from a user; one or more electronic signals from a user interface; or one or more EMG signals from a user and one or more electronic signals from a user interface, and to cause the digits to assume a predetermined grip pattern depending on the signal(s) received, wherein the control system is programmable to cause the hand to assume a predetermined grip pattern based on the signals received. A selected grip pattern may be displayed on a display.

The hand may further comprise one or more indicators that a signal has been received by the control system. At least one of the indicators may be a visual indicator. In one form, the hand may comprise at least one visual indicator that a signal has been received by the control system.

The hand preferably comprises a user interface comprising one or more input members through which a user may cause the hand to assume a predetermined grip pattern.

The one or more input members may comprise one or more buttons. Preferably, the user interface comprises a panel comprising one or more input members and one or more visual indicators.

According to a further aspect, the invention provides an automated hand comprising: a palm; two or more digits extending from the palm; and one or more motors configured to cause at least one of the digits to move; wherein the automated hand is configured to operate when submerged in a fluid.

Preferably, the hand comprises a wrist joint configured to attach the palm to a lower arm member comprising a sleeve and also configured to form a watertight attachment to the sleeve.

Preferably, the wrist joint comprises an axle about which the palm can curl and flex and/or rotate laterally.

In one form, the wrist joint is configured to hold electrical connectors that connect electronics in the sleeve with electronics in the palm and/or digits of the hand.

In yet another aspect, the invention provides an automated hand substantially as described herein and with reference to the accompanying drawings, either individually or in combination with any feature, and in any configuration.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

BRIEF DESCRIPTION OF THE FIGURES

The invention is further described with reference to the following drawings, in which:

FIG. 39 is a side view of the clutch plate of the clutch of FIG. 33;

FIG. 40 is a plan view of the clutch plate of the clutch of FIG. 33;

FIG. 41 is a perspective view of the clutch plate of the clutch of FIG. 33;

DETAILED DESCRIPTION

Figure 1:
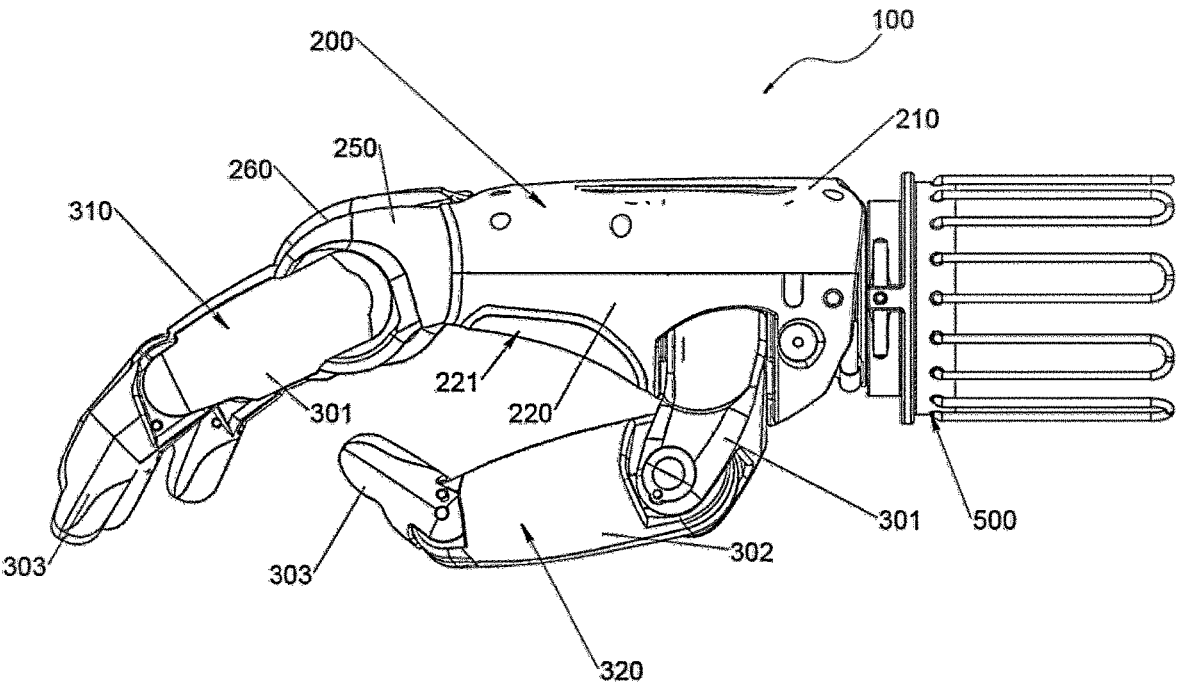
FIG. 1 is a side view of one form of automated hand of the invention.
Figure 2:
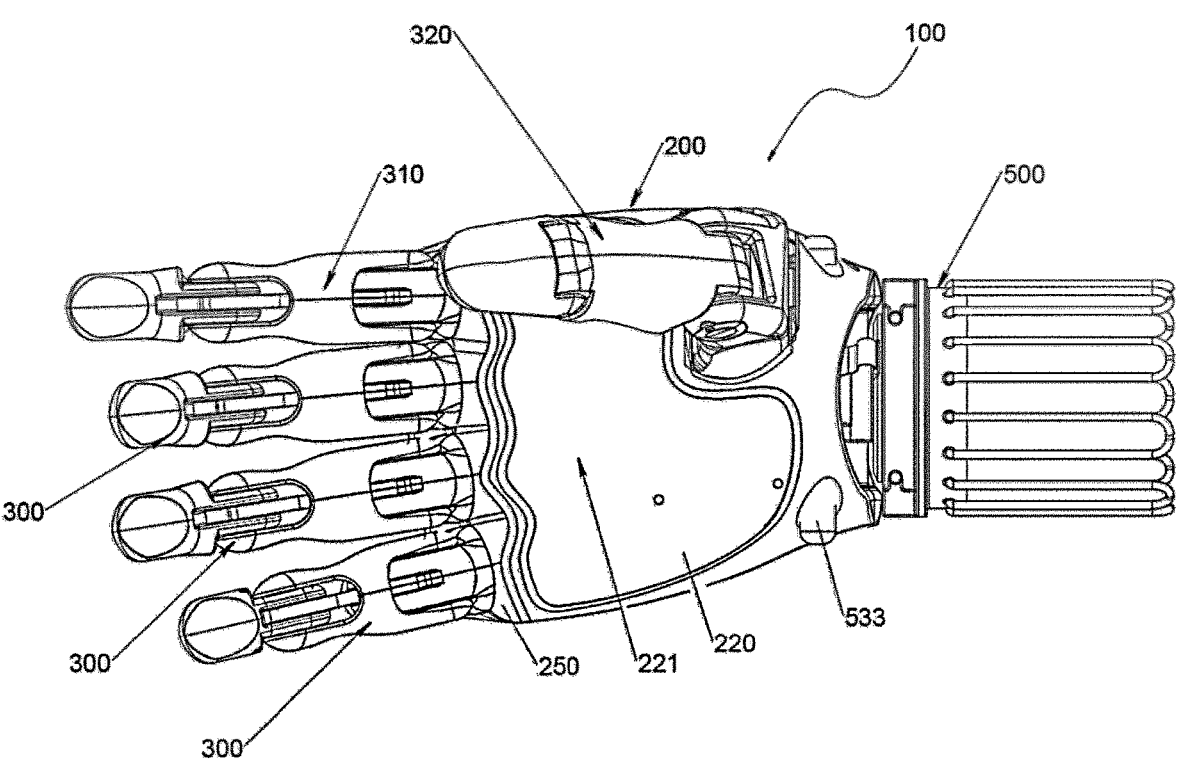
FIG. 2 is a perspective view from below of the automated hand of FIG. 1.

The invention relates to an automated hand, such as a prosthetic hand or training hand for a prosthetic. Whilst the description is given by way of example with respect to electric motors it will be appreciated that a range of suitable actuators may be employed.

First Exemplary Embodiment

The automated hand 100 of the first exemplary embodiment is shown in FIGS. 1 to 25 and comprises a palm 200 and two or more digits 300 extending from the palm 200. Each digit may be attached to the palm by a knuckle joint. The digits are configured to move between an open, substantially flexed (extended) position, and a substantially closed, gripping position. A digit 300 may be in the form of a finger 310 or thumb 320. In one example, the hand 100 may comprise two digits 300, one being a finger 310 and the other being a substantially opposing thumb 320. In another form, the hand 100 may comprise four or more fingers 310 and a substantially opposing thumb 320. In yet another form, the hand 100 may comprise only two or more fingers 310. It is envisaged that in yet another form, the hand 100 may comprise one or more fingers 310 and two or more thumbs 320, although this is not a preferred embodiment because it is an unnatural looking hand.

The hand 100 of the invention also comprises one or more drive motors 230. Each motor 230 may be configured to drive movement of just one digit 300, or of more than one digit. For example, where the hand 100 comprises four fingers and a thumb, a single motor 230 may be used to drive movement of the thumb from one position to another. Two motors 230 may be used to drive movement of the fingers, each of the finger motors being configured to move two fingers. In another form, each digit 300 may be driven by an independent motor 230 configured to drive movement of that digit 300 only. In one form, the thumb may comprise two motors, where the first motor is configured to cause the thumb to curl and flex and the second motor is configured to cause the thumb to move from one side of the palm toward the other.

Each digit 300 comprises a body that may be formed as a single part or as two or more parts. A human finger, for example, comprises a proximal phalanx, a middle phalanx, and a distal phalanx. The automated hand 100 of the invention may also comprise one or more digits 300 comprising proximal 301, middle 302, and distal phalanges 303, as shown in the thumb of FIG. 1. Alternatively, one or more digits of the hand may be configured to comprise only proximal 301 and distal phalanges 303, as shown in the fingers of FIG. 1. In this configuration, the proximal 301 or distal phalanx 303 may optionally be angled or curved. In some forms, the point of the angle or curve may resemble the appearance of a joint between a middle phalanx 302 and the proximal phalanx 301 or between the middle phalanx and distal phalanx 303, as the case may be. In the embodiment shown in FIG. 1, the distal phalanx 303 of the finger 300 is angled to resemble a jointed middle phalanx and distal phalanx in a substantially relaxed, slightly curled position. In yet another form, the digit may comprise a proximal phalanx only. Again, the digit may comprise one or more curves or angles so that the digit substantially resembles a bent/curled human finger.

In one form, the body of the digit 300 may be a substantially hollow shell, which may comprise working components within the hollow interior. The working components are configured to transfer rotational movement of the motor to the digit. In another form, the body of the finger may be substantially solid.

The automated hand 100 of the invention also comprises a power supply configured to operate the one of more drive motors 10 and other electronic components of the hand. The power supply may be a battery or other power storage device, such as a slow release capacitor. Optionally, the power supply is rechargeable.

Preferably, the hand 100 comprises an indicator that provides an indication of when the power supply is running low. For example, the indicator may be a visual indicator in the form of a flashing light or a light of a particular colour. Additionally, or alternatively, the indicator may be a sound indicator that beeps or makes a particular sound to indicate that the power supply is running low.

The hand 100 of the invention may also comprise a control system configured to control operation of the motors of the hand. The control system may also be configured to control operation of other electronic components of the hand. The control system may be programmable to suit the needs and skills of the user. The control system may optionally be reprogrammable also to suit the changing needs and skills of the user over time.

Metacarpal Brace

In one form, as shown in FIGS. 1 to 6, the palm 200 of the hand 100 comprises a body in the form of an outer shell. The outer shell defines an interior of the palm in which working components and electronics may be held. The outer shell may be formed as one piece. In another form, the outer shell of the palm comprises a first part 210 and a second part 220 configured to be attached together. The first part of the outer shell of the palm is configured to form the upper part 210 of the hand, i.e. the back of the hand. The second part 220 of the outer shell is configured to form the lower part 220 of the hand, i.e. the gripping part of the palm. In the interests of clarity, the first and second parts 210, 220 will now be referred to as upper and lower parts 210, 220 respectively. However, this terminology should not be interpreted so that the first part is always in an upper position and the second part is always in a lower position. As will be appreciated, the hand may rotate so that the upper part (the back of the hand) faces toward the ground and is therefore lower than the lower part of the palm.

The palm 200 of the hand 100 may also comprise a resiliently flexible and compressible metacarpal brace 250. The metacarpal brace 250 may be configured to support the knuckle joints and therefore also the digits of the hand.

In one form, one or more knuckle joints are directly or indirectly attached to a connector, which is configured to attach to the metacarpal brace. The connector 260 may comprise a knuckle joint 261 and a connecting arm 20. The knuckle joint 261 may be located at a first end of the connecting arm 20. The connecting arm 20 may be configured to attach to or at least be supported by the metacarpal brace 250. The connecting arm 20 is thus mounted to the metacarpal brace 250 in a "free floating" manner such that each connecting arm 20 may rotate about the metacarpal brace 250 when a lateral force is applied to a digit. The resilience of the metacarpal brace 250 allows the digits to splay (rotate apart in the plane of the palm) and provide impact absorbtion for forces applied to a digit in a direction normal to the palm. This avoids the need for any internal frame with the digits being attached to the palm only by the metacarpal brace secured to the top and bottom palm halves.

The metacarpal brace 250 is configured to substantially extend across the knuckle region of the hand. For example, the metacarpal brace 250 may extend between two or more connectors and may be configured to allow the connectors (and therefore the knuckle joints 261 and distal portion of the palm 200) to splay apart slightly, to squish together slightly, and to move slightly up and down relative to each other to simulate (at least in part) the natural movement of the knuckles of a human hand. The connectors 260 are configured to connect the finger(s) 300 to the palm 200. Therefore, by allowing the connectors 260 to splay, due to the resilience of the metacarpal brace, the fingers 300 are also able to move laterally and splay to some extent, such as when an article such as a brush handle is placed between fingers. The metacarpal brace preferably has such resilience that at least two digits may be splayed by at least 5 degrees (more preferably at least 10 degrees and even more preferably at least 20 degrees) due to relative movement between the connector and palm allowed by elastic deformation of the metacarpal brace. The word "splay" in this context refers to digits that are generally parallel in their neutral position and the extent to which they are "splayed" represents the angle between the centrelines of the adjacent digits. Where the digits are not parallel "splay" refers to the additional angular rotation between adjacent digits. The resilience of the metacarpal brace also provides impact absorbtion from lateral forces (i.e. forces from either side of the hand such as an impact to the little finger forcing it towards the 3$^{rd}$ finger) and normal forces (i.e. forces acting against a digit in a direction normal to the plane of the palm). This is due to a connector 260 being able to move with respect to the palm due to elastic deformation of the metacarpal brace 250. The metacarpal brace may provide elastic deformation such that a lateral force of between 2.5 and 20 Newtons applied to the tip of a digit results in angular rotation with respect to the palm in the plane of the palm (digit splay) of at least 3 (preferably at least 5) degrees.

The metacarpal brace preferably provides impact absorbtion for forces applied to a digit in a direction normal to the palm such that each connector may rotate by at least 2 (preferably at least 5 degrees) relative to the palm in the plane of driven movement of a digit (digit rotation) due to elastic deformation of the metacarpal brace. The metacarpal brace may provide elastic deformation such that a force of between 2.5 and 20 Newtons applied to the tip of a digit in a direction normal to the plane of the palm results in angular rotation of the digit relative to the palm of at least 3 degrees.

Similarly, by allowing the connectors 260 (and therefore the knuckle joints 261) at either side of the hand 100 to move downwardly, for example, the fingers 300 are able to more readily conform around and grip a small or round object, such as a tennis ball. The compliant nature of the automated hand means that the hand is also able to provide a more natural grip in a handshake.

Metacarpal Brace Material Properties

The material selected for use as the metacarpal brace should be capable of retaining a high degree of flexibility when exposed to the normal cold and hot ambient temperatures in end-use. The hand might be exposed to icy water (0° C.) or very hot water (60° C.).

Dynamic mechanical thermal analysis (DMTA) is a laboratory test which accurately describes the actual behaviour of a polymeric material during its end-use, such as use as a 'metacarpal brace'. This is an ASTM protocol selected from either D 2236, D 4065, D 4440, or D 5279. It incorporates 'temperature' as a parameter for material selection The DTMA test measures the ability of a material to absorb and/or retain energy during a mechanical operation such as bending.

It describes flexibility and resilience (rebound) in terms of the ratio of absorbed energy/retained energy. This unitless ratio is called "damping coefficient" or "tangent delta" for that material, and it can be generated over a wide range of temperatures.

In analytical terminology the material used for a metacarpal brace would require a flexibility (damping factor/tangent delta) of less than 1.0, preferably between 0.05 and 0.8 when measured over a temperature range of minus 20° C. to plus 100° C.

To provide the flexible, semi-compressible and resilient characteristics, the metacarpal brace may be made from any suitable material or combination of materials, including but not limited to: elastomers, rubber, silicone, compressible polymers and thermoplastics materials. Thermoset elastomers (either hydrocarbon, fluorocarbon or silica-based), thermoplastic elastomers, thermoset rubbers, inherently soft thermoplastics or foamed compositions based on any of these polymers are suitable for this application.

Some typical polymeric materials which qualify against these criteria are shown below in Table 1. These 'families' of polymers can be described as:

Crosslinked thermoset elastomers (such as ethylene/acrylate or butyl rubber), crosslinked thermoset polyurethanes (Sorbothane®), crosslinked thermoset polysiloxanes, thermoplastic polyurethanes (Huntsman, Bayer), thermoplastic elastomers (DuPont Hytrel®, DSM Arnital® copolyester, Arkema Pebax® copolyamide). Alloys and blends of these polymers (with other polymers as well as inorganic fillers), and foamed versions of these families of elastomeric materials would also be candidate materials. Composite materials such as carbon fibre reinforced polymers may also be used.

TABLE 1

| Criteria for Metacarpal Brace Polymer Flexibility | | | | |
|---|---|---|---|---|
| THERMOSET POLYMER POLY- | THERMOPLASTIC POLYMER POLY- | RESILIENCE (2632) (%) | HARDNESS (2240) | DAMPING FACTOR (2236, 4065) |
| SILOXANE | — | 20-40 | A 10-30 | 0.4 |
| ETHYLENE/ACRYLATE | — | 20 40 | A 50-90 | 0.5 |
| ISOBUTYLENE/ISOPRENE [BUTYL] RUBBER | — | 20-40- | A 50-90 | 0.8 |
| URETHANE* | — | 30-60 | A 30-90 | >0.1 |
| URETHANE ** | — | 20-38 | A 30-70 | 0.2-0.5 |
| — | URETHANE*** | 40-60 | A 58-71 | 0.5 |
| — | URETHANE **** | 40-60 | A 70-95 | 0.35-0.6 |
| — | COPOLYESTER | 30-50 | D 63-72 | 0.08-0.1 |
| — | COPOLYAMIDE | 30-50 | D 40-90 | <0.14 |

Notes
*based on the methodology disclosed in U.S. Pat. No. 4,605,681
** Sorbothane ®
***based on data provided by Huntsman Advanced Materials
**** based on Army Research Lab TR 4296 data Data in Table 1 shows that a broad range of thermoset and thermoplastic polymers meet the criteria for selection as a material from which to manufacture the metacarpal brace. The damping factor is preferably in the range of 0.05-0.80 between minus 20° C. and plus 100° C., and more preferably in the range 0.05 to 0.5. Resilience is preferably between 20 to 60%. Hardness is preferably between Shore A hardness 10 to 90 (more preferably 30 to 60) or Shore D hardness 40 to 90. A metacarpal brace formed of a material having a Shore A hardness of about 30 has been found to be particularly suitable.

It is to be appreciated that the required functionality of the metacarpal block may be achieved in ways other than using a solid metacarpal block as per the examples above. For example, cuts could be provided in a solid block or it may otherwise be formed so that a smaller section of material is exposed to the rotational forces applied by the digits. Foamed materials may have a different structure, for example the metacarpal brace may extend further along the actuators where the foamed materials are easily deformed.

As shown in FIGS. 1 to 5, the metacarpal brace 250 comprises a body 251 having a first end 252. The first end 252 may face substantially in the direction of the wrist. The support 250 also comprises a second end 253. The second end 253 may be positioned substantially opposite the first end and may face substantially in the direction of the finger(s) 300 of the hand 100. The metacarpal brace 250 also comprises an upper surface 254, which may be configured to form part of an upper surface 211 of the upper part 210 of the palm of the hand. Preferably, the upper surface of the metacarpal brace 250 is configured to be substantially flush with the upper surface of the upper part 210 of the palm 200. The brace 250 also comprises a substantially opposing lower surface 255, which may be configured to form part of a contact surface 221 of the palm of the hand. The contact surface is the outer surface of the lower part of the hand which typically comes into contact with an item that is gripped within the palm of the hand. The lower surface of the metacarpal brace 250 may be substantially flush with the contact surface of the lower part 220 of the palm 200.

The metacarpal brace 250 is positioned between the knuckle joints 261 and the body of the palm 200. The upper 210 and lower 220 parts of the palm 200 may be configured to connect together and to hold at least a portion of the metacarpal brace 250 between the upper and lower parts 210, 220. For example, in one form, the first end 252 of the metacarpal brace is configured to be held between the upper and lower parts 210, 220 of the palm 200 and to be substantially flush with the upper and lower surfaces of the palm so that the metacarpal brace 250 acts as an extension to the upper and lower parts 210, 220.

Figure 3:
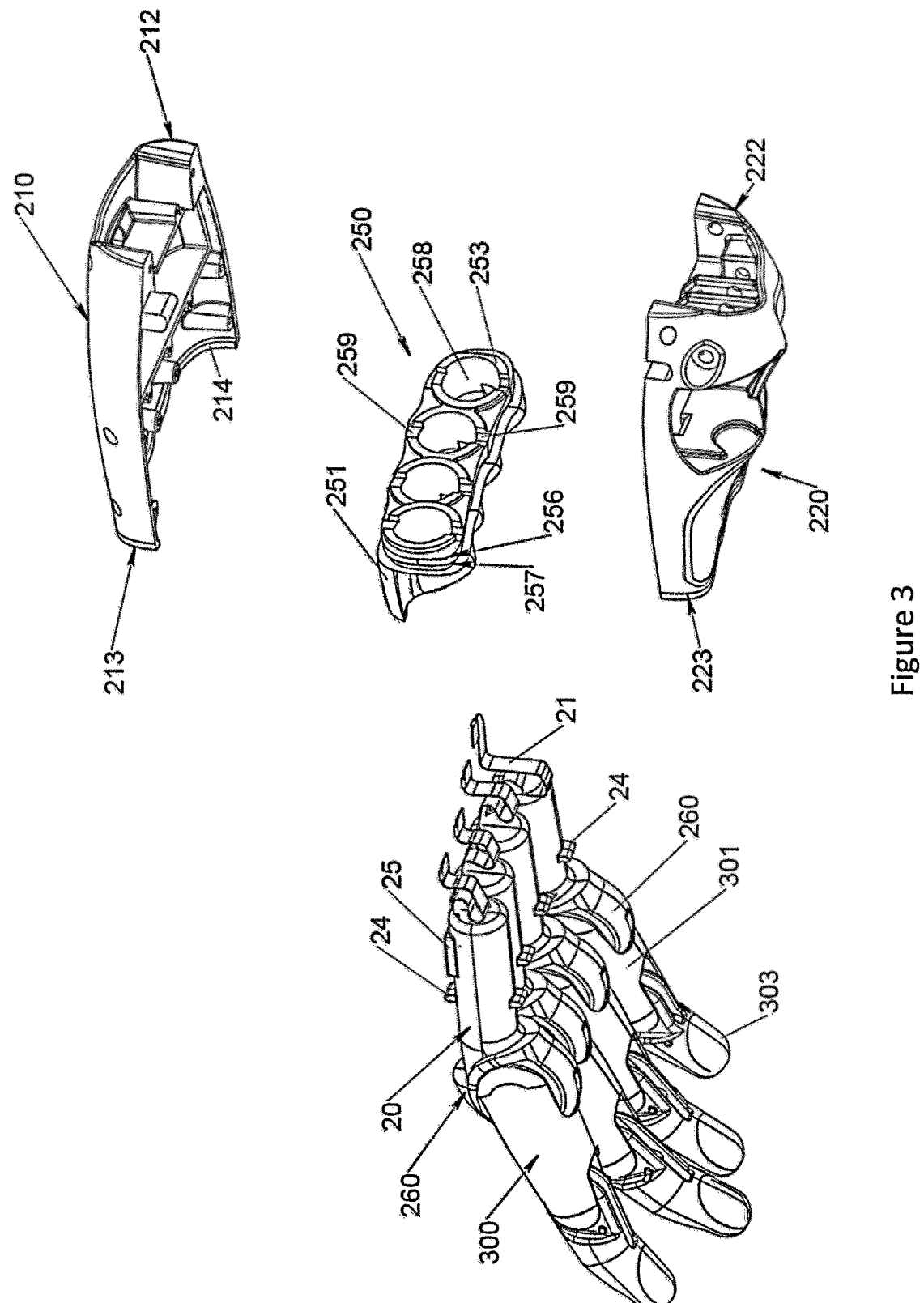
FIG. 3 is an exploded view of one form of automated hand of the invention.

In one form, the palm 200, including the metacarpal brace 250, may comprise an attachment system to attach the metacarpal brace 250 to the upper 210 and lower 220 parts of the palm. In one embodiment, as illustrated, the upper part 210 of the palm comprises a first end 212 and a second end 213. The lower part 220 of the palm also comprises a first end 222 and a second end 223. The second end of both the upper and lower parts 210, 220 may comprise a lip 214 extending around all, or substantially all, of the second end, as shown in FIG. 3. The first end 252 of the metacarpal brace 250 may comprise a flange 256 that substantially extends around the first side 252. A channel 257 may be located between the flange 256 and the rest of the body of the metacarpal brace 250, as shown best in FIGS. 3, 4c and 4d. The walls of the channel 257 are formed by an inside edge of the flange 256 and the rest of the body 251 of the metacarpal brace 250. The lip 214 of each of the upper and lower parts 210, 220 of the palm 200 may be configured to project into the channel 257 and to abut the inside edge of the flange 256. By connecting the first and second parts 210, 220 of the palm together, the lip 214 projects into the channel 257 and the flange 256 prevents the lip 214 from pulling out of the channel 257, even if the metacarpal brace is flexed or pulled away from the first and second parts of the palm 200.

It is envisaged that in other forms, the channel 257 and flange 256 may not extend around the whole, or substantially the whole, of the metacarpal brace 250 and may instead extend around a part or parts of the metacarpal brace 250. For example, the flange 256 may be formed of a series of projections provided around the first end of the metacarpal brace 250 so that a channel 257 is formed between each projection and the rest of the support 250. In another form, the flange 256 may be provided at opposing sides of the first end of the metacarpal brace 250.

It should be appreciated that this is just one form of attachment system to attach the metacarpal brace to the upper and lower parts of the palm. Any other suitable attachment system may otherwise be used. For example, the metacarpal brace and the upper and lower parts of the palm may comprise complementary male and female attachment members that mate with each other to attach the metacarpal brace to the palm. A clip connection system may be another form of attachment system that could be used. In yet another form, at least a portion of the metacarpal brace may be adhered to or integrally moulded with one of or both of the upper and lower parts of the palm.

As mentioned above, the metacarpal brace 250 is configured to support one or more connectors 260 to indirectly support the knuckles 261 and digits 300 of the hand.

In one form, the body of each connector 260 may be configured to provide a motor housing. For example, the connecting arm 20 may comprise a motor housing. In another example, the connector may comprise a connecting arm, a motor housing, and a knuckle joint located between the connecting arm and motor housing. In this arrangement, the motor housing may be located within the body of the digit and the connecting arm may be located within the palm. The motor housing may house a drive motor and may optionally house one or more encoders and/or sensors.

The metacarpal brace may be configured to hold the connecting arm of each connector. For example, one or more support apertures 258 may extend through the metacarpal brace 250 from the first end 252 to the second end 253. In one form, as shown in FIG. 2a, four support apertures 258 are provided. Each support aperture 258 is preferably configured to receive a connecting arm 20 of a connector 260 within it.

In another form, the metacarpal brace 250 may be configured to support the one or more drive motors 10 of the hand 100 so that each support aperture 258 is configured to receive a drive motor within it. In effect, each support aperture 258 may be configured to form a motor bay.

In a preferred form, each support aperture 258 is substantially cylindrical and is dimensioned to snugly hold a substantially cylindrical motor 10 or connecting arm 20. In one form, substantially the whole of the curved walls of a motor 10 or connecting arm 20 may be held within a support aperture 258. Alternatively, only a portion of the motor 10 or connecting arm 20 may be held within a support aperture 258 so that the metacarpal brace 250 suspends the motor/connecting arm in space within the palm of the hand, as indicated in FIG. 3 and shown in FIGS. 5 and 6.

The hand 100 may be assembled so that the second end 253 of the metacarpal brace 250 abuts the knuckle joint 261 of each connector and so that the connecting arm 20 of each connector is held within a respective support aperture 258.

Figure 5:
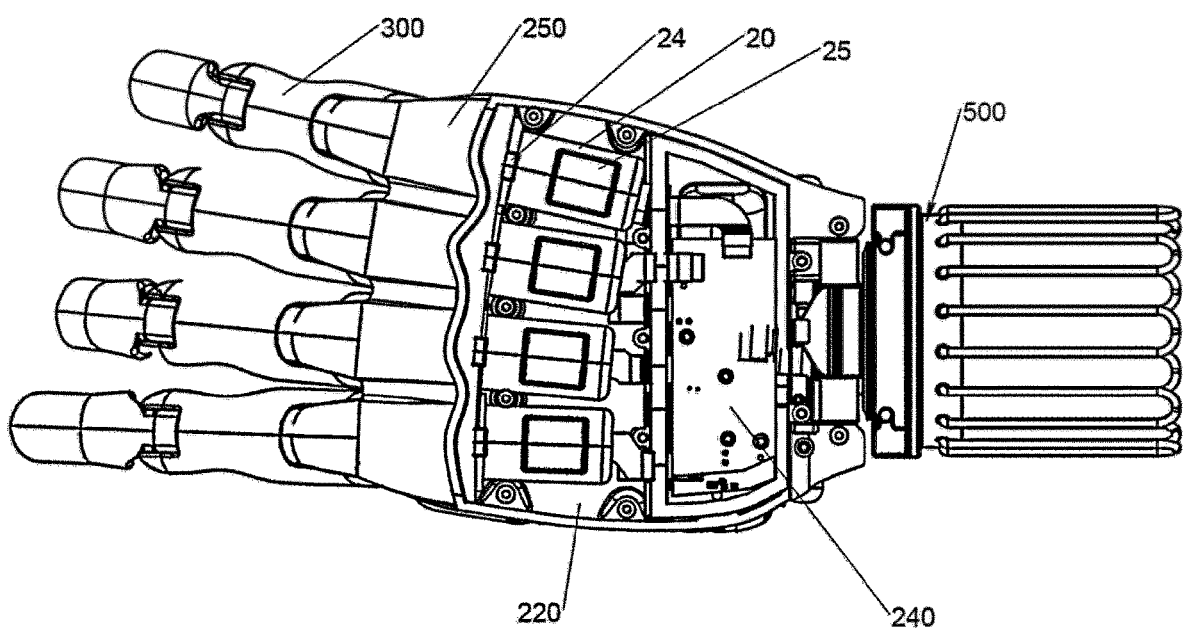
FIG. 5 is a partially cut away plan view of one form of automated hand of the invention.
Figure 6:
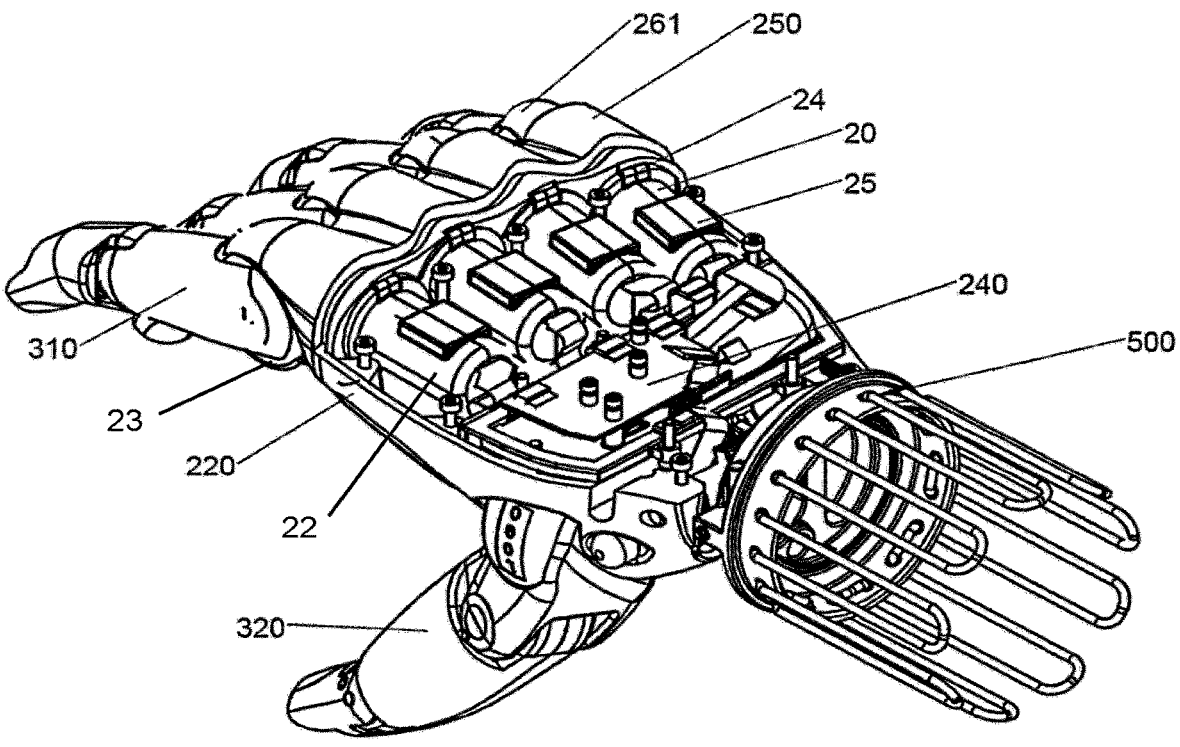
FIG. 6 is a perspective view of the automated hand of FIG. 5.

In one form, the hand may be configured so that a first end of each connecting arm 20 is suspended within the palm 200 of the hand. For example, a portion of a connecting arm 20 at or near a second end 23 of the connecting arm is held within a support aperture 258. The remaining portion of the connecting arm 20, near the first end 22 of the connecting arm may extend from the support aperture 258 so as to be suspended within the interior of the body of the palm 200 of the hand, as shown in FIGS. 5 and 6.

In another form, the metacarpal brace is longer so that substantially the whole of the connecting arm(s) is/are held within the support aperture(s).

In one form, the hand 100 comprises four fingers 300 and four drive motors 10, each drive motor 10 being configured to drive movement of an individual finger 300. The metacarpal brace 250 of the hand 100 comprises four support apertures 258, each support aperture extending between the first 252 and second ends 253 of the metacarpal brace 250. The connecting arms are configured to fit snugly within a respective support aperture 258 of the metacarpal brace 250.

In one form each drive motor 10 is housed within a connecting arm 20 of a respective connector 260. Preferably, the connecting arms 20 are configured to provide watertight housings for the drive motors 10.

Typically, a first end 22 of each motor and of each motor housing comprises an electrical connector 21 that is connected to the respective motor 10 and is configured to directly or indirectly connect to the power supply and/or a control system. The control system may be configured to determine when and how quickly a motor 10 should drive movement of a finger 300 and in what direction the finger should move. The second end of each drive motor 10 is located at or near a second end 23 of the respective motor housing (if the drive motor 10 is placed within a motor housing). A second end of each motor may comprise an output shaft that is directly or indirectly connected to an actuation system for a respective finger 300 and is configured so that an output of the motor 10 directly or indirectly engages with the finger 300 to drive movement of the finger 300.

Figure 4A:
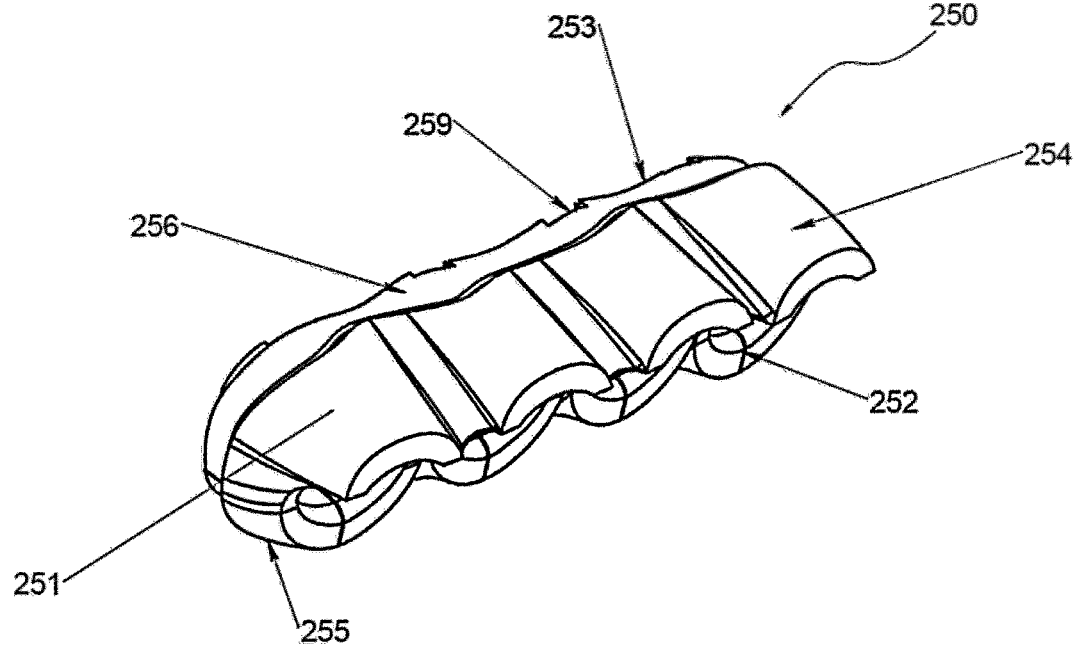
FIG. 4A is a side perspective view of one form of metacarpal brace of the invention.
Figures 4B, 4C, 4D:
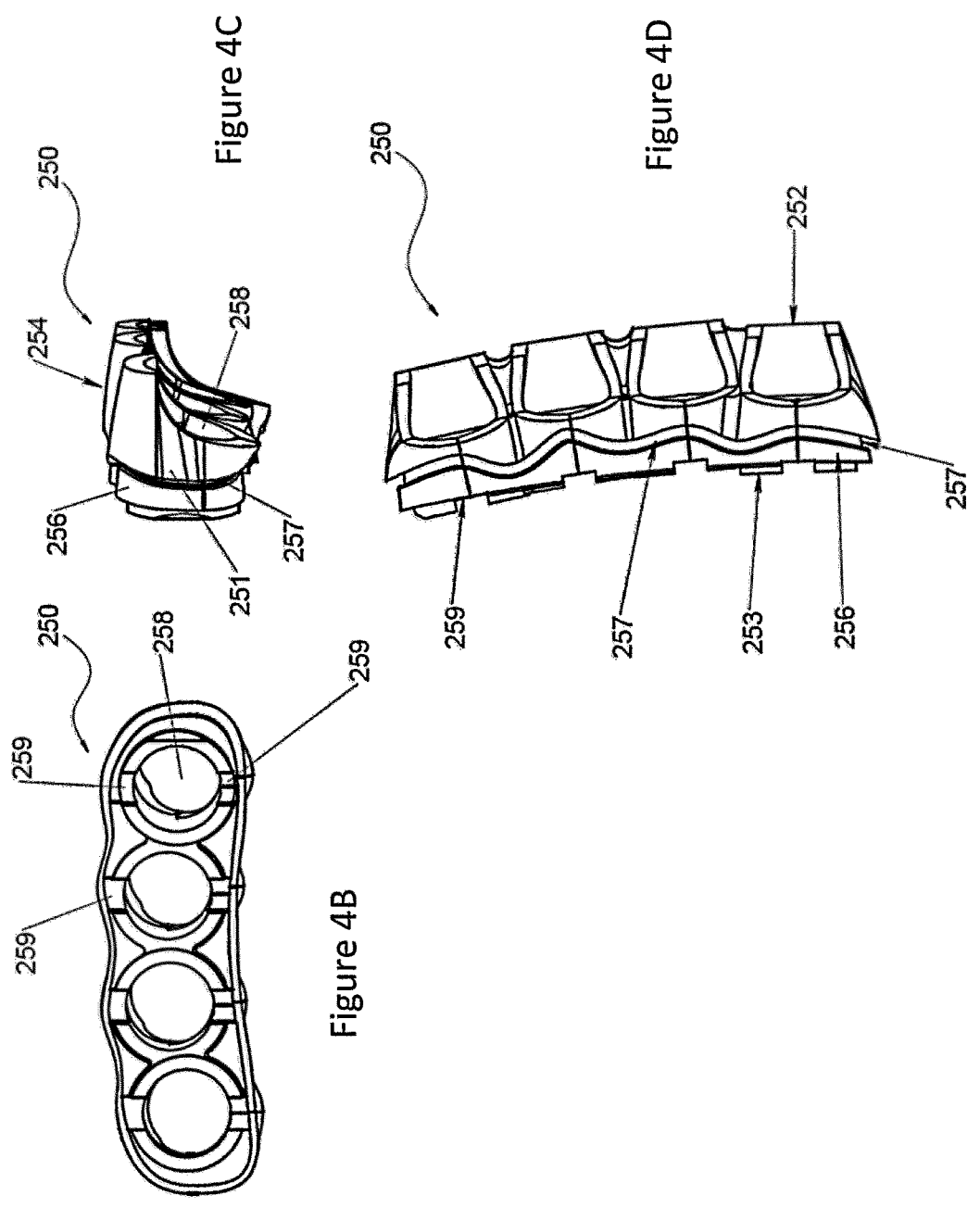
FIG. 4B is a front perspective view of the metacarpal brace of FIG. 4A.
FIG. 4C is another side perspective view of the metacarpal brace of FIG. 4A.
FIG. 4D is a bottom perspective view of the metacarpal brace of FIG. 4A.

In one form, the metacarpal brace 250 and connecting arms 20 comprise an anti-rotation system in which the two parts 250, 20 engage with each other to prevent the connecting arms 20 from rotating within the support apertures 258 as the drive motors cause the digits to move. In one form, as shown in FIGS. 3 to 4d, one or more support apertures 258 may comprise at least one stop, which may comprise an opening 259, such as a recess or notch, configured to engage with at least one corresponding stop, such as a projection 24, formed on one or more respective connecting arms 20. In this arrangement, each connecting arm 20 is held within a support aperture 258 so that a projection 24 of the motor housing is held within a respective opening 259 formed in the metacarpal brace 250. Alternatively, the motor bays of the metacarpal brace may be provided with one or more stops in the form of projections configured to mate with one or more stops in the form of openings/recesses provided on the respective connecting arms. When the fingers are moving, any torque transferred from the fingers 310 to the connecting arms 20 is prevented from causing the connecting arms 20 to rotate within the support apertures 258. The anti-rotation system may also prevent the connecting arms 20 from rotating within the support apertures 258 when the hand 100 receives an impact force. Alternatively, rotation may be prevented by providing an aperture of non-circular cross section, such as a keyhole, with the actuator having a corresponding interengaging profile.

Optionally, one or more of the connecting arms 20 are configured to comprise one or more end stops 25 for pressing against the shell of the palm to prevent the respective fingers from bending back on the upper part of the palm and/or to prevent the finger from being pulled down too far. In other words, the end stops 25 are configured to provide maximum points of movement for the fingers in order to prevent extreme movement of the fingers 300. In one form, an end stop 25 may be provided on an upper portion of the motor housing (the upper portion being the part that faces toward the upper part of the palm). Additionally or alternatively, an end stop 25 may be provided on a lower portion of the motor housing (the lower portion being the part that faces the lower part 220 of the palm). Optionally, one or more electronics housings located on or within the connecting arm may also form end stops 25.

Typically, the metacarpal brace 250 is semi-flexible and semi-compressible to provide the palm 200 and knuckle joints 261 with sufficient structural integrity as well as the ability to flex somewhat. The amount of flexibility and compressibility provided at various areas of the metacarpal brace 250 effects the extent of movement of the hand 100 and fingers 300.

In one form, the metacarpal brace 250 may be configured to provide different compressibility and/or flexibility characteristics at different areas of the metacarpal brace 250. For example, the areas of the metacarpal brace 250 that align with gaps between the fingers 300 may be more flexible than other areas of the support 250. The greater flexibility may be achieved by making these areas of the metacarpal brace 250 thinner and/or by making these areas of the metacarpal brace 250 from a more flexible material than other areas of the support 250.

The metacarpal brace may also be substantially resilient, so that after compressing or flexing, the metacarpal brace substantially returns to its original state.

The flexible and semi-compressible nature of the metacarpal brace 250 provides significant advantages to the automated hand 100. For example, when fingers 300 of the hand 100 form a gripping position, the metacarpal brace 250 can flex and curve to allow the fingers 300 to substantially splay around the gripped object and at least partially mould the hand 100 around the object. In this way, the movement of the metacarpal brace 250 is much like the palm of a human hand, which will curve slightly (particularly at the sides) to grip an object, such as a tennis ball. By curving slightly around an object, the hand 100 is provided with an increased number of contact points at which the hand 100 contacts the object. The more contact points that the hand 100 has, the better the grip of the hand. Typically, for a conventional automated hand to achieve a good grip, the motors of the hand drive the digits of the hand to clamp onto the surface of the object being gripped. The stronger the clamping force, the less likely the object will slip out of the hand. But this requires the motors to work hard, which strains the motors. Even when a strong clamping force is used, it can be difficult for conventional automated hands to grip some objects. For example, a slippery and curved object, such as a glass bottle, may still be difficult for a conventional hand to grip reliably. However, because an automated hand comprising a metacarpal brace of the present invention is able to substantially curve around an object to provide more contact points, the motors of the hand do not need to work as hard to achieve the required gripping force. As a result, the longevity of the motors and batteries is enhanced and a better grip is obtained.

Another advantage offered by the substantially flexible and compressible metacarpal brace is that when the automated hand of the invention receives an impact force, particularly side impacts to the little of index fingers, the hand is able to absorb some of the force to minimise damage to the working parts of the hand. In particular, the cushioning effect created by the compressible metacarpal brace helps to diffuse the impact force, which could otherwise damage sensitive components of the hand, such as the motor gearboxes. In this way, the metacarpal brace helps to improve the longevity of the motors and other components of the hand.

A hand comprising the flexible and compressible metacarpal brace of the invention may also be quieter where the drive motors are housed within the connecting arms because the metacarpal brace substantially absorbs the vibrations of the drive motors.

Another advantage provided by the metacarpal brace is that a hand comprising the support may feel more natural in a hand shake. This is due to the ability of the hand to compress slightly under pressure from the hand shake and to curve slightly to grip the other person's hand.

Furthermore, because the metacarpal brace extends across the knuckle region of the hand, the brace supports the knuckles and the fingers, which provides better control and accuracy of movement of the fingers.

Whilst the metacarpal brace is shown as an integrally formed block it is to be appreciated that a separate mount could be provided for each actuator—either individually mounted to the palm or secured together after formation.

Thumb

Figure 7:
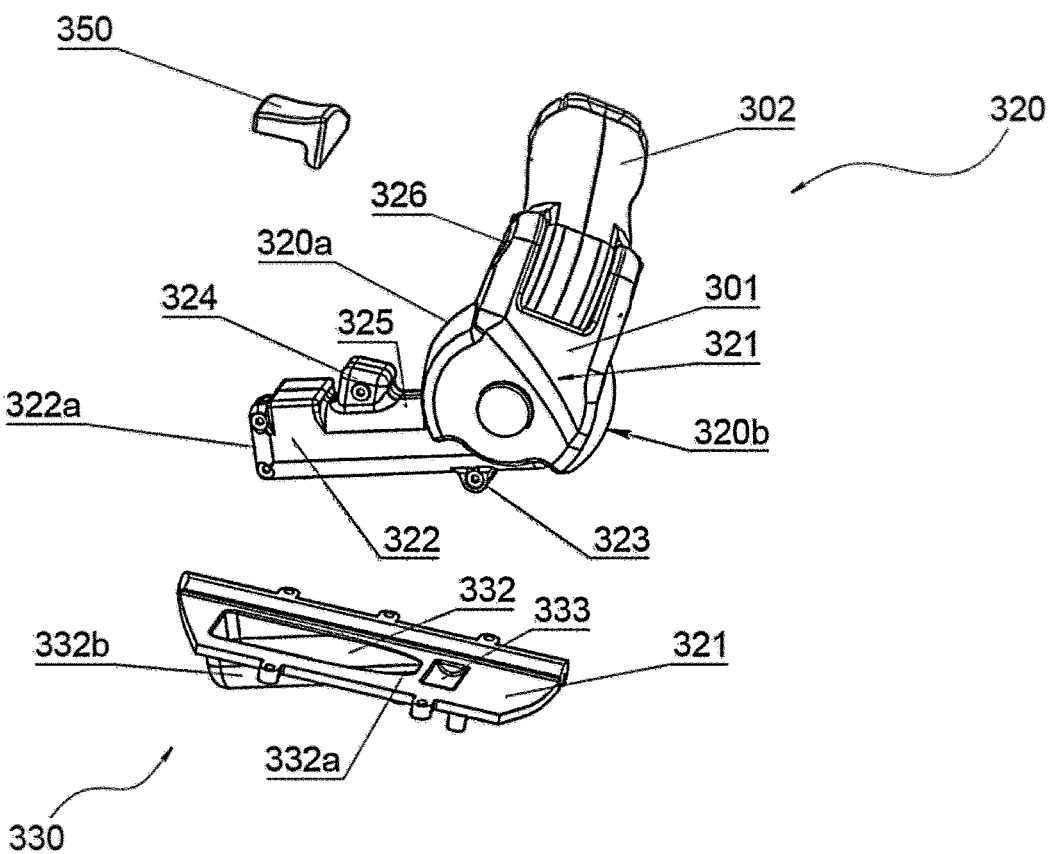
FIG. 7 is an exploded view of one form of thumb, thumb support and thumb cushion of the invention.
Figure 8:
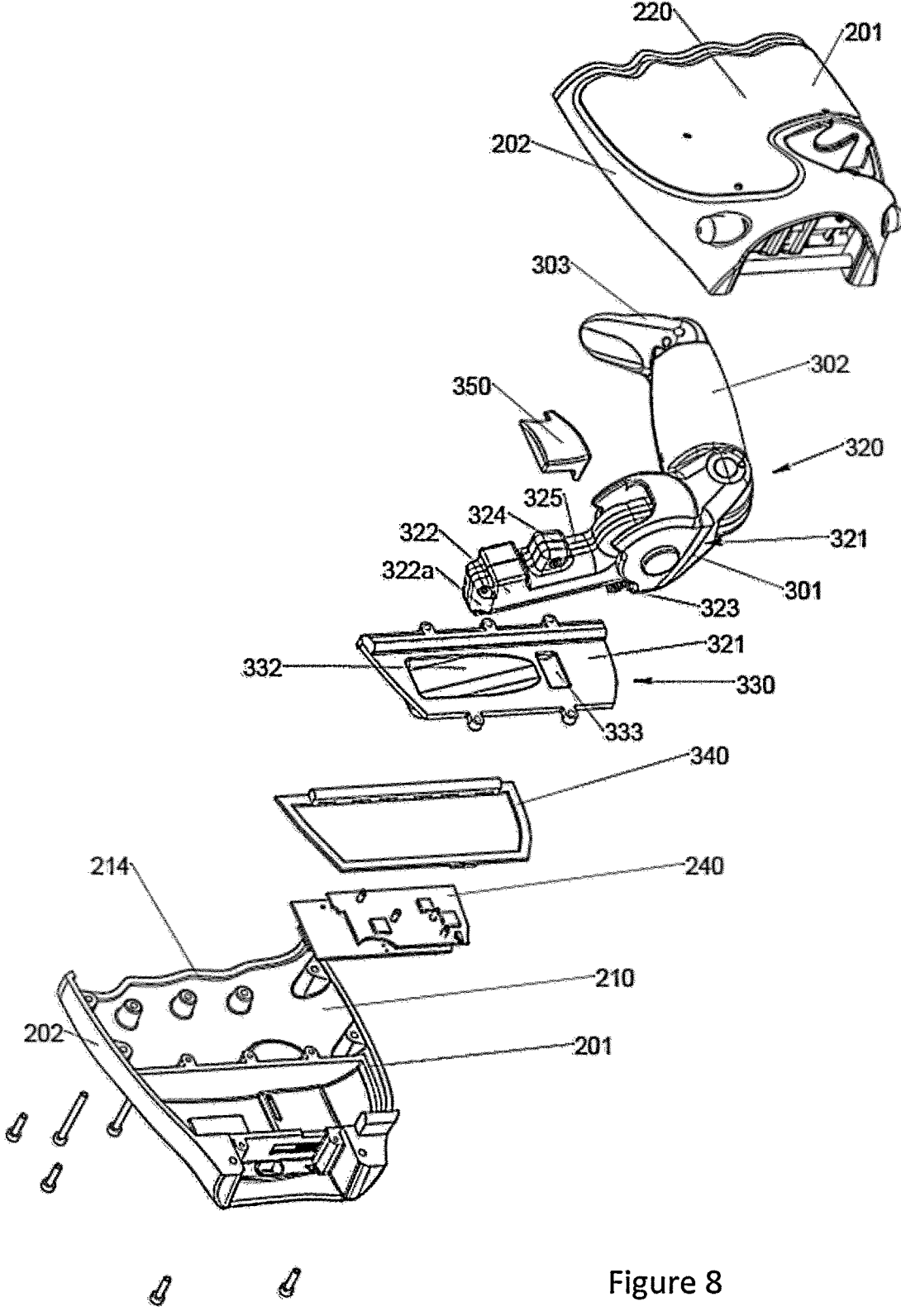
FIG. 8 is an exploded view of one form of palm and thumb configuration of the invention.

In one form, as shown in FIGS. 7 and 8, the automated hand 100 of the invention comprises a digit 300 in the form of a thumb 320, configured to substantially oppose at least one finger 310 of the hand. Preferably, the automated hand 100 comprises four fingers 310 and a substantially opposing thumb 320 in an arrangement the same as or similar to that of a human hand.

The thumb 320 is mounted at or near a first side 201 of the palm 200 of the hand so that the thumb body 321, which may be configured to curl and flex, substantially opposes at least one other digit 300, such as a forefinger for example. The thumb 320 is configured to extend from the contact surface of the palm to substantially resemble a human thumb and palm arrangement.

In one form, the thumb body 321 comprises a proximal phalanx 301, a middle phalanx 302, and a distal phalanx 303, as illustrated in FIG. 8. In other forms, the thumb body may comprise a proximal phalanx only or a proximal and distal phalanx, as described above in relation to the various embodiments that digits of the hand may take.

In one form, the thumb 320 is configured to be mounted on the upper part 210 of the palm 200 of the hand 100. The thumb 320 may be mounted directly on an inner surface of the shell of the upper part 210 of the palm or the thumb 320 may be mounted on an intermediate member, such as a thumb support 330, which is itself mounted on an inner surface of the upper part 210 of the palm. For example, the hand 100 may comprise a thumb support 330 configured to position the thumb 320 in a desired location and orientation with respect to the palm 200. In one form, the thumb support 330 is configured to attach to or rest within or on the upper part 210 of the palm shell.

The thumb 320 may be configured to be mounted on the thumb support 330. For example, in one form, the thumb 320 comprises a body 321 and a base member 322 that extends from one side of the thumb body 321 to form a substantially L-shaped thumb 320. The thumb 320 is positioned on the palm 200 so that when the hand 100 is in an open position, the thumb body 321 extends from the contact surface of the palm 200 at or near a first side 201 of the palm and the base member 322 extends across the palm 200 toward the second side 202 of the palm. The second side 202 of the palm is substantially opposite to the first side 201 of the palm. In this arrangement, a distal end 322*a* of the base member 322 substantially faces toward the second side 202 of the palm. The thumb 320 may be configured to rotate toward and away from the distal end 322*a* of the base member 322, so as to rotate toward and away from the second side 202 of the palm, as described below.

In one form, the thumb support 330 comprises a first surface 321 having a sloping first recess 332. In the form illustrated, the first recess 332 slopes along the length of the thumb support 330. The angle of the first recess 332 is preferably inclined toward the thumb body 321. The first recess 332 comprises a first end 332a, which is the shallowest end of the recess 332, and a substantially opposing second end 332b, being the deepest end of the recess 332. Optionally, the first recess 332 comprises an opening. In one form, the opening may be provided at the second end 332a of the first recess 332.

The first recess 332 may be configured to receive at least a portion of the base member 322 of the thumb 320, so that the base member 322 is substantially held in position within the first recess 332. The angle of the first recess 332 not only helps the thumb 320 to be held in position on the thumb support 330, but also allows the body 321 of the thumb 320 to be located and angled on the palm 200 in a substantially natural looking position to provide a substantially natural looking hand 100.

The thumb support 330 may also comprise a second recess 333 located on the first surface 321. In the form illustrated, the second recess 333 is located near the first end 332a of the first recess 332. The second recess 333 may be configured to receive a positioning element 323 that projects from the base member 322 to help ensure that the base member 322 maintains its position on the thumb support 330 without slewing from side to side. The second recess 333 and positioning element 323 may be of any suitable complementary shape, such as a rectangular shape, a star shape, a hexagonal shape, or square shape.

In one form, as shown in FIGS. 7 and 8, the positioning element 323 forms a hinge about which the thumb 320 may rotate toward and away from the distal end 322a of the base member 322. In this form, the projecting hinge 323 may be substantially semi-cylindrical and the second recess 333 may also be substantially semi-cylindrical so that the hinge 323 can nest within and rotate within the second recess 333. The hinge/positioning element 323 and second recess 333 may extend substantially perpendicularly to the length of the base member 322.

Optionally, the thumb support 330 comprises a compressible material, such as rubber, silicon, or an elastomer to provide impact resistance to the thumb 320.

The thumb 320 is typically assembled so that the base member 322 is located on the thumb support 330, which is itself located on an inner surface of the upper part 210 of the palm 200. Optionally, the thumb support 330 is located on and/or surrounded by a seal 340 that seals the join between the thumb support 330 and the upper part 210 of the palm 200. The upper part 210 of the palm 200 may comprise a substantially hollow housing between the thumb support 330 and the upper part 210, so that the thumb support 330 forms a lid for the housing. Electronics 240 for the hand 100 may optionally be housed within this housing 230 of the upper part 220 of the palm. For example, the control system and other electronic components may be held within the housing. Typically, the electronics housing 230 is provided at or near the base of the upper part 210 of the palm, i.e. near the join between the palm 200 and the wrist 500. By sealing the housing 230 for the electronics, the electronics 240 may be kept watertight.

When the contact surface of the palm of the hand is facing upwards, as illustrated in FIG. 8, the lower part 220 of the palm 200 sits above the upper part 210, the thumb support 330, and base member 322 of the thumb. The lower part 220 of the palm comprises an opening 216 through which the body 321 of the thumb 320 projects. In this way, the base member 322 of the thumb 320 is substantially held within the interior of the shell of the palm 200 and the body 321 of the thumb projects from the contact surface 221 of the palm 200.

The thumb 320 may be configured to be a substantially stationary digit 300 projecting from the palm 200 of the hand 100 or the thumb 320 may be configured to make controlled movements.

In one form, the thumb 320 comprises a first motor that may be configured to cause the thumb body 321 to curl toward the contact surface 221 of the palm and uncurl or flex away from the contact surface. The phalanges of the thumb may curl about joints between the phalanges, such as a first joint 326 between the proximal and middle phalanges, and a second joint 327 between the middle and distal phalanges for example.

The thumb 320 may also comprise a second motor that is configured to cause the thumb body 321 to move toward and away from the distal end of the base member 322 (i.e. to move the thumb towards and away from the second side 202 of the palm, proximate to the little finger location if the hand comprises a little finger).

In effect, the thumb 320 may be configured to simultaneously hinge toward the second side 202 of the palm 200 and to curl toward the contact surface 221 of the palm 200 to grip an object. Similarly, the thumb 320 may uncurl and hinge away from the second side of the palm to release an object.

The motor(s) may be located in any suitable position on the hand 100, such as in the palm 200, in the base member 322 of the thumb, or within the body 321 of the thumb. For example, the first motor may be housed within the body 321 of the thumb. In one form, the second motor is housed within the base member 322.

Preferably, the motor(s) is/are held within a motor housing. For example, the first motor may be held within a first motor housing and the second motor may be held within a second motor housing. One or more encoders and/or sensors may also be held within the first and/or second motor housings.

The automated hand 100 optionally comprises a compressible thumb cushion 350 configured to be placed between the base member 322 and the shell of the palm 200 to help absorb impact forces and prevent damage to the thumb 320 and its components, particularly the motor(s).

In one form, the thumb cushion 350 is located between the base member 322 and the lower part 220 of the palm. In this form, the thumb cushion 350 may be attached to an inner surface of the lower part 220 of the palm; an upper surface of the base member 322 (the upper surface being that surface that faces toward the lower part of the palm); or the thumb cushion 350 may simply be sandwiched between the base member 322 and lower part 220 of the palm.

In one form the thumb cushion 350 is configured to be mounted on the base member 322, as shown in FIGS. 7 and 8, so as to be located between the base member 322 and the lower part 220 of the palm. The base member 322 may comprise a cushion mount 324 by which the thumb cushion 350 may be mounted on the base member 322. For example, the cushion mount 324 may be in the form of an opening, such as an aperture or recess, and the thumb cushion 350 may comprise a mounting surface having a projection configured to be received within the opening. Preferably, the projection is snugly received within the opening or the projection and opening may be keyed or otherwise configured to hold the projection of the thumb cushion within the opening so that the thumb cushion is held in place on the base member. In another form, as illustrated, the base member 322 comprises a cushion mount in the form of a projection 324 and the thumb cushion 350 is configured to fit over the projection 324 to be held in place on the base member 322.

In one form, the projecting cushion mount comprises a housing, or at least part of a housing, for the second thumb motor. For example, a first surface of the base member 322 may comprise a cushion mount in the form of a projection 324 within which the second motor is located, as shown in FIGS. 7 and 8. If the hand 100 is oriented so that its contact surface 221 is facing upwards, the first surface of the base member 322 is its upwardly facing surface, which also faces toward the inner surface of the lower part 220 of the palm.

The compressible thumb cushion 350 may be configured to be located at the projecting free end of the projecting motor housing/cushion mount 324 or the thumb cushion 250 may be configured to substantially surround the cushion mount 324.

In one form, as illustrated in FIGS. 7 and 8, the base member 322 is configured to provide a cradle 325 in which the projecting cushion mount 324 is located. The thumb cushion 350 is configured to be positioned substantially within the cradle 325 and to substantially surround the projecting cushion mount 324.

As the thumb body 321 rotates toward and away from the second side 202 of the palm, the thumb may pivot slightly within the thumb support so that the base member 322 is caused to move up and down slightly. For example, if the thumb body 321 moves toward the second side 202 of the palm 200, the distal end 322a of the base member 322 is pushed into the first recess 332 of the thumb support 330. Conversely, if the thumb body 321 moves away from the second side 202 of the palm, the distal end 322a of the base member pushes against the inner surface of the lower part 220 of the palm 200. Therefore, if the end of the thumb 320 receives an impact force that pushes the base of the thumb body 321 toward the upper part 210 of the palm 200, the positioning element 323 of the base member 322 will be pushed against the second recess 333 of the thumb support 330 and the distal end 322a of the base member 322 will be pushed toward the lower part 220 of the palm in a see-saw arrangement. To prevent an impact force causing damage as the substantially rigid structure of the base member 322 impacts against the substantially rigid lower part 220 of the palm, the thumb cushion 350 is located between these two parts 322, 220. In this arrangement, the base member 322 presses against the compressible thumb cushion 350, which absorbs at least some of the impact. Therefore, the compressible nature of the thumb cushion 350 helps to dampen the force being transferred between the thumb 320 and the palm 200. Consequently, the thumb, thumb motor(s) and other components of the thumb are less likely to be damaged by an impact force to the end of the thumb.

In one form, the thumb cushion 350 may be configured to be mounted on the base member and to abut an inner side 320a of the thumb 320. The inner side of the thumb is that side from which the base member 322 extends. In this arrangement, the thumb cushion 350 is able to substantially dampen the lateral movement of the thumb 320 when the thumb receives an impact force from the first side 201 of the palm. The thumb and its sensitive components are therefore less likely to be damaged as a result of a lateral impact.

The thumb cushion 350 may be made from any suitable cushioning material, such as rubber, an elastomer, silicone, or the like. Preferably, the material of the thumb cushion is substantially resilient to allow the thumb cushion to substantially return to its original shape after deformation.

Independent Digit Speed, Position and/or Force

In one form, the control system of the hand 100 of the invention comprises one or more motor controllers configured to control the movement of digits 300 of the hand independently. In one form, the motor controller(s) may be configured to control the speed of one or more drive motors, which drive movement of the digits, independently. In particular, the motor controller(s) may be configured to control the motor speed and pulse width modulation of one or more of the drive motor(s). Each motor controller is directly or indirectly connected to a power supply and to one or more drive motors of the hand 100.

By controlling the movement of one or more digits independently, it is possible to independently and deliberately control the speed at which the controlled digits move; the force at which controlled digits grip an item; and the position of the controlled digits.

The hand 100 may comprise one or more drive motors, each drive motor being configured to cause movement of at least one of the digits. In one form, the hand may comprise five digits and at least five motors. For example, a first motor may be connected to a first digit, such as the forefinger, to drive movement of the first digit, a second motor may be connected to a second digit, such as the middle finger to drive movement of the second digit, and so on, as shown in FIGS. 3, 5, and 6. As described above, each motor may be held within a housing, which is preferably watertight.

The motor controller(s) may be configured to cause one or more of the digits 300 to move at any desired speed. For example, the motor controller(s) may be configured to cause two or more digits 300 to move at the same speed or a different speed, or to cause each digit 300 to move at the same speed or a different speed.

In one form, each motor controller comprises a PID controller.

One motor controller may be used to control the speed of a single digit 300, such as a finger 310. For example, each digit 300 of the hand 100 may be connected to a motor controller configured to control the speed of movement of that digit 300 only. In one form, the hand may comprise five motor controllers, five motors, and five digits. For example, a first motor controller may be connected to a first motor to control the speed of movement of a first digit, such as the forefinger; a second motor controller may be connected to a second motor to control the speed of movement of a second digit, such as the middle finger, and so on so that the speed of movement of each digit may be independently determined by the respective controller.

Alternatively, a single motor controller may be used to control the speed of two or more digits 300. For example, the hand 100 may comprise a thumb and four fingers 310 corresponding to a forefinger, middle finger, ring finger, and little finger. At least one motor controller may be used to control the speed of movement of the thumb and at least one other controller may be used to control the speed of movement of the forefinger. Yet another motor controller may be used to control the speed of the middle finger, ring finger, and little finger. In this arrangement, the speed of both the thumb and forefinger is controlled independently, whereas the middle finger, ring finger, and little finger move at the same speed because these fingers are governed by a single motor controller.

In one form, the thumb may comprise two drive motors: a first drive motor to cause the thumb to curl and flex toward and away from the contact surface of the palm; and a second drive motor to cause the thumb to pivot from the first side of the palm to the second side and back. The speed of each drive motor may be controlled by an independent motor controller, so that the speed at which the thumb curls and flexes may be the same as or different to the speed at which the thumb moves between the first and second sides of the palm.

The control system may be configured to determine the speed of the digits suitable for the user. For example, if the hand comprises four fingers and will be used to grip small objects or rounded objects one or more motor controllers may be configured to cause the ring finger to move faster than the middle finger. The motor controller(s) may be configured to cause the middle finger to move at the same speed as the forefinger or faster. Additionally or alternatively, the motor controller(s) may be configured to cause the little finger (or finger closest to the outside edge of the hand if the hand does not comprise four fingers) to move at the same speed as the ring finger or faster.

In another form, the hand 100 comprises five digits 300 corresponding to a forefinger, middle finger, ring finger, little finger, and a thumb. One or more motor controllers are configured to cause the ring finger and little finger to move at a faster speed than the forefinger and middle finger.

The motor controllers may be positioned in any suitable location on the hand. Preferably, the control system and motor controllers are located on a printed circuit board within the electronics housing in the palm of the hand.

One or more of the motor controller(s) may be pre-programmed before being built into the hand 100. Alternatively, the user or a therapist may program one or more of the motor controller(s) according to the user's needs and after manufacture of the hand. Optionally, the one or more of the motor controllers are reprogrammable.

By providing a control system for independent digit speed and/or digit position and/or digit force, precise gripping tasks can be performed. For example, the controller(s) may be programmed to define the before and after grip positions for a handshake grip, to provide a higher little finger and ring finger force compared to the other fingers of the hand, and to provide particular finger speeds in order to provide a substantially realistic, natural handshake grip.

Another advantage provided by a hand with independent digit speed is that the control system of the hand may be configured to provide a precision utensil grip.

Yet another advantage is that the force applied to grip an object can be varied between digits. For example, by causing the drive motor for the little finger to move that finger faster than an index finger, the grip force for the little finger will be stronger than the grip force for the index finger once the fingers are used to grip an object.

Yet another advantage is that the positions of the digits can be independently controlled and deliberately determined. For example, the controller(s) may be configured to cause the digits to move to a particular grip pattern, such as a handshake grip.

Clutch Device

In one form, as shown in FIGS. 9 to 14, the automated hand of the invention may comprise one or more clutch devices 400. Each clutch device may be configured to engage with and to disengage from a drive motor 10, so that the drive motor can be stopped from driving a digit where the digit receives an end impact force or is under a significant pulling force. For example, if a curled digit 300 lifts a heavy weight, the drive motor of that digit strains to keep the digits in a curled configuration. Too much strain on the motor can damage the motor and otherwise wear the motor over time. The clutch device 400 of the invention is configured to help avoid this damage by disengaging the digit 300 from the drive force of the drive motor 10 when the digit is overly strained by an end impact or significant pulling force.

The drive motor is configured to operate in a first direction, which causes the digit to curl toward the contact surface of the palm 200 of the hand 100 in a gripping position, and to operate in an opposing second direction, which causes the digit to uncurl to form an open position. An output shaft of the drive motor is configured to directly or indirectly engage with at least one clutch device of the invention.

The hand may comprise one or more clutch devices 400 for use with one or more digits of the hand. For example, only the forefinger and thumb may comprise a clutch device 400. In another form, as illustrated, each digit 300 of the hand, whether a finger or thumb, may comprise at least one clutch device 400. In one form, a digit may comprise two clutch devices 400, one on each side of the body of the digit. For simplicity, the configuration of a single clutch device 400 will be described in relation to a single digit, in particular, a finger. However, it should be appreciated that the clutch device 400 of the invention may otherwise be used for a thumb. Because the thumb may comprise two drive motors, the thumb may comprise one or more clutch devices to engage with each of the drive motors of the thumb. For example, in one embodiment, if the thumb comprises two drive motors, the thumb may comprise four clutch devices (two clutch devices for each drive motor).

In one form, the clutch device may comprise a first portion configured to directly or indirectly engage with a drive motor and a second portion configured to directly or indirectly engage with a finger. For example, a first end of the clutch device may engage with a drive motor of a finger, as described above, and a second end of the clutch may be configured to engage with the finger.

The finger 310 is connected to a knuckle joint 261, which is connected to the palm 200 of the hand. The knuckle joint 261 is configured to allow the finger to hinge about the knuckle joint 261 so that the finger can curl and flex.

The finger 310 may be formed as separate, jointed parts (such as separate phalanges), or the finger may be formed as a single part (such as a proximal phalanx), as described above.

The clutch device 400 may be configured to be located within a joint between two adjoining phalanges 301, 302, 303 or within the knuckle joint 261 between the palm 200 and the digit 300. In a preferred form, the clutch device 400 is located within the knuckle joint 261 between the palm 200 and proximal phalanx 301 of the digit 300.

Figure 9:
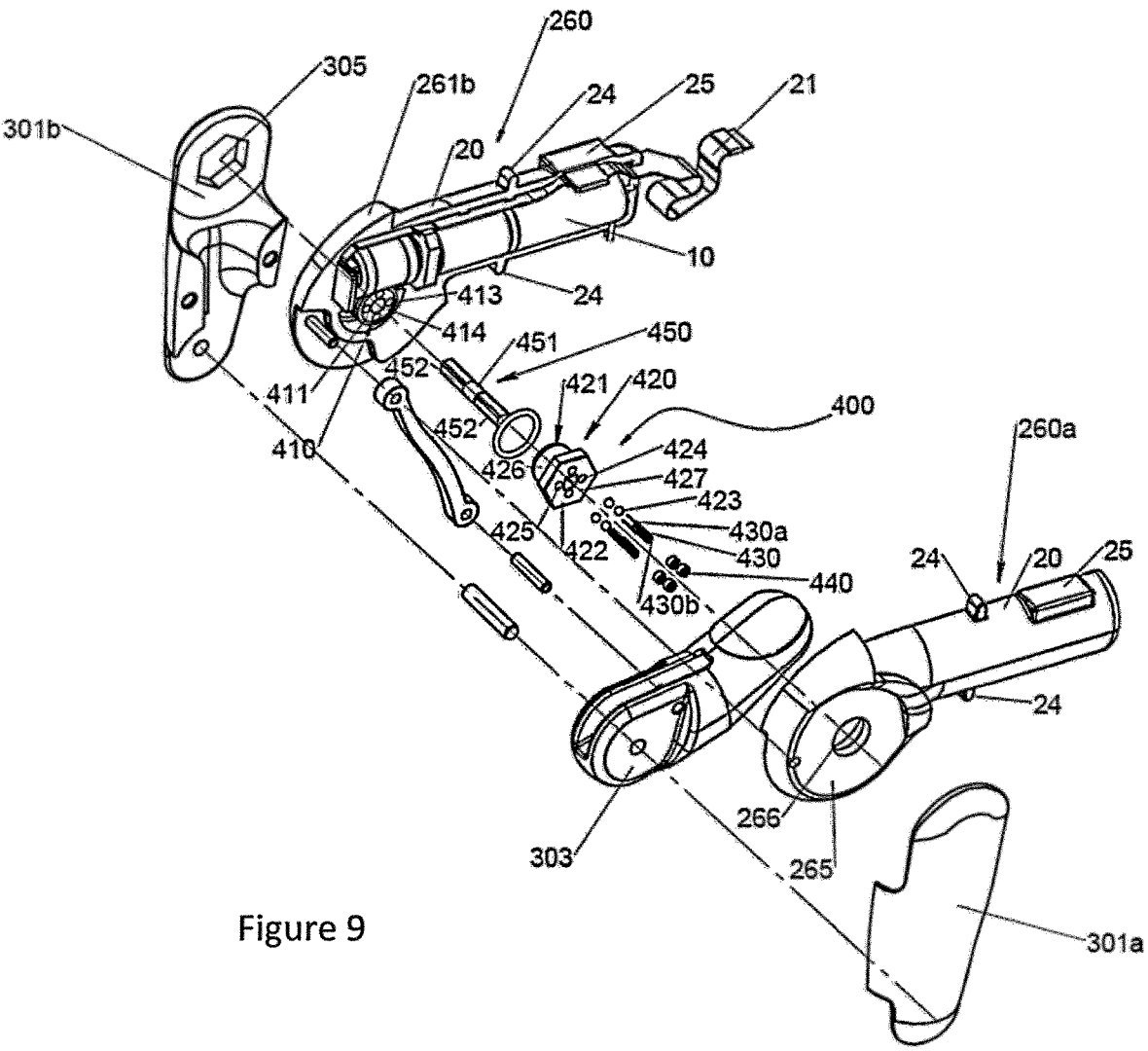
FIG. 9 is an exploded view of one form of digit and clutch device of the invention.

The knuckle joint 261 may be formed from one or more parts. In one form, the knuckle 261 is formed from two parts; a first part 261a and a second part 261b that may be joined together, as shown in FIG. 9.

The knuckle joint 261 may comprise a body having at least a partially curved outer surface to resemble the curves of a human knuckle. In one form, the knuckle joint 261 forms part of a digit support member 260. The digit support member 260 may also comprise a connecting arm 20. In one form, the knuckle joint 261 is located at or near a first end of the digit support member 260 and a connecting arm 20 is located at or near a second end of the digit support member. The connecting arm 20 may be configured to extend from the knuckle joint 261, so that the knuckle joint 261 forms one end of the digit support member 260 and the connecting arm 20 forms the other end.

The drive motor of one or more fingers may be held within the connecting arm 20. Optionally, one or more encoders and/or sensors may also be held within the motor housing. The connecting arm 20 may be substantially elongate and may be configured to be located within the palm 200 of the hand 100. In one form, the connecting arm 20 and/or motor 10 may be configured to be held within a motor bay of a metacarpal brace 250, as described above. In another form, the connecting arm 20 and/or motor 10 may be held within a digit 300, such as within the proximal phalanx for example.

The body of the knuckle joint 261 may be of any suitable shape. In one form, the body 261 comprises a substantially circular disc having opposing mounting surfaces 265a, 265b.

In one form, the clutch device comprises a driven element 410, a clamping member 420, and a compression member 430.

The driven element 410 may be directly or indirectly engaged with a drive motor 10 and is caused to rotate by the drive motor 10. For example, the driven element 410 may be a worm wheel that engages with a worm gear driven by an output shaft of the drive motor 10. In another form, the driven element 410 may be a bevelled gear wheel, or any other suitable wheel or rotating element, so that as an output shaft of the drive motor rotates, the driven element 410 is also caused to rotate.

The driven element 410 may be located within the body of the knuckle joint 261. The driven element 410 may comprise at least one contact surface 411 configured to engage with the clamping member 420. In one form, the driven element comprises substantially opposing contact surfaces 411a, 411b.

The clamping member 420 may comprise a first surface 421, configured to engage with the contact surface 411 of the driven element 410. For example, the first surface 421 of the clamping member 420 may be configured to press against the contact surface 411 of the driven element.

The compression member 430 may be configured to cause the first surface of the clamping to engage with the contact surface 411 of the driven element 410, such as by pressing against the contact surface 411. The compression member 430 may therefore be configured to cause the clamping member 420 to engage with the contact surface 411 of the driven element 410 using a compression force. In one form, the compression member 430 may also be configured to cause the first surface 421 of the clamping member to disengage with the contact surface 411 of the driven element.

Where a digit 300 comprises a single clutch device 400, the clamping member 420 and compression member 430 are located on one side of the driven element 410. However, where the digit 300 comprises two clutch devices 400, a clamping member 420 and compression member 430 will be located on each side of the driven element 410.

In one form, the clamping member(s) 420 may be located adjacent to the contact surface(s) 411a, 411b of the driven element 410.

The driven element 410 and clamping member 420 may be held in a position adjacent each other by a common axle 450 configured to extend through an axle receiving aperture

414 formed in the driven element 410 and an axle receiving aperture 425 formed in clamping element 420.

In one form, the axle receiving aperture 414 of the driven element is substantially centrally located on the contact surface 411 of the driven element. The axle receiving aperture 414 may extend through the body of the driven element from the first contact surface 411a to the second contact surface 411b.

The axle receiving aperture 425 of the clamping member 420 may be substantially centrally located on the clamping member 420. In one form, the axle receiving aperture 425 may extend through the body of the clamping member from the first surface 421 to a second surface 422 of the clamping member.

In one form, the axle may be substantially cylindrical and may extend through substantially circular axle receiving apertures of the driven element and clamping member.

In another form, the axle comprises a substantially cylindrical central region 451 and non-cylindrical ends 452. The central region 451 of the axle 450 may be configured to project through an axle receiving aperture 414 of the driven element 410 comprising a substantially circular cross-section. In this form, the driven element 410 may rotate freely about the axle 450.

The non-cylindrical ends 452 of the axle 450 may be a square shape, hexagonal shape, or any other suitable shape that is configured to key into a correspondingly shaped axle receiving aperture 425 of the clamping member 420. In this form, as the clamping member 420 rotates, the axle 450 is caused to rotate also. The driven element 410 is able to rotate freely around the axle 430 whereas the axle 430 and clamping member 420 are locked in position relative to each other.

The axle helps to ensure that the driven element and clamping member remain substantially aligned with each other.

The knuckle joint 261 may comprise a clutch receiving aperture 266 to house at least a portion of the clutch device and to help to align the driven element and clamping member. The clutch receiving aperture 266 may extend through the body of the knuckle joint from the first outer surface 265a to the second outer surface 265b. The clutch receiving aperture 266 is preferably substantially centrally located on the outer mounting surfaces 265a, 265b of the knuckle joint 261. In one form, the clutch receiving aperture 266 has a circular cross section to form a cylindrical aperture that extends through either one of the first 261a and second 261b parts of the knuckle joint 261 or through both the first 261a and second 261b parts. The driven element 410 may be located within the clutch receiving aperture 266. In one form, at least a portion of the clamping member 420 may also be received within the clutch receiving aperture 266.

In one form, the clutch device 400 may comprise an engagement system to engage the contact surface of the driven element 410 with the first surface of the clamping member 420 so that the clamping member 420 is caused to rotate when the driven element 410 rotates. The engagement system may also be configured to disengage the clamping member 420 from the driven element 410 when the digit 300 is subjected to a significant force.

In one form, the engagement system comprises one or more male engagement members configured to engage with the one or more female engagement members. The male engagement members may comprise projections configured to engage with female engagement members comprising recesses. The male projections may be substantially convex or may be substantially spherical projections, such as projecting balls. The male projections may be integral with, attached to, or otherwise connected to the clamping member or driven element from which the projections project, as the case may be. In one embodiment, at least one female engagement member may comprise a substantially concave recess, such as a dimple. The recessed area may comprise one or more openings. For example, the recess may comprise a centrally located aperture with curved and tapered edges to form a semi-circular recess. In another form, a female engagement member may comprise a concave recess comprising a plurality of apertures within the recessed surface. The recess(es) may also be substantially shallow. In other words, the depth of the recesses may be substantially shallow or may comprise tapered edges having substantially shallow angles of taper.

The contact surface of the driven element may comprise one or more male engagement members or female engagement members configured to engage with corresponding female engagement members or male engagement members on the first surface of the clamping member. In one form, the contact surface may comprise both male and female engagement members configured to engage with corresponding female and male engagement members on the first surface of the clamping member.

Optionally, the engagement system comprises four male engagement members configured to engage with four female engagement members. The male and female engagement members are configured to be equally spaced from and around a central point of the contact surface 411 of the driven element 410 or a central point of the first surface 421 of the clamping member 420, as the case may be.

In one form, the contact surface 411 of the driven element 410 may comprise one or more male engagement members and the clamping member may comprise one or more female engagement members. Each male engagement member may be configured to be at least partially received in a respective female engagement member to engage the driven element 410 and clamping member 420 together.

In one form, the contact surface 411 of the driven element 410 comprises one or more apertures. Each aperture comprises a closed end and an open end. The open end is located at the contact surface 421.

A compression member may be held within each aperture. A male engagement member may be located at the open end of the aperture to project, at least in part, from the contact surface. In this arrangement, the compression member is held within the aperture between the male engagement member and the closed end of the aperture. The projecting male engagement member presses against the first surface of the clamping member and against one end of the compression member. The compression member is therefore held under compression within the aperture and is configured to push the male engagement member(s) against the first surface 421 of the clamping member 420.

Optionally, the compression member is a spring, but in other forms, the compression member may be formed from any substantially compressible, resilient material that is able to compress and then spring back to its original form.

In one form, the male engagement member may comprise a ball, such as a ball bearing, which is held under compression between the clamping member 420 and driven element 410.

The compression force of the compression member 430 presses the male engagement member, such as a ball bearing, against the first surface 421 of the clamping member 420.

As described above, the female engagement members on the first surface of the clamping member 420 may comprise one or more recesses within which respective male engagement members may nest when the driven element 410 and clamping member 420 are engaged. In this arrangement, the clamping member 420 is caused to rotate when the driven element 410 rotates. Where the male engagement member(s) comprise(s) a ball bearing, the one or more recesses may be configured to allow a ball bearing to rotate somewhat within a respective recess. In this configuration, the invention provides a spring-loaded ball bearing clutch device 400 that causes the clamping member 420 to rotate as the driven element 410 rotates.

Figure 10A:
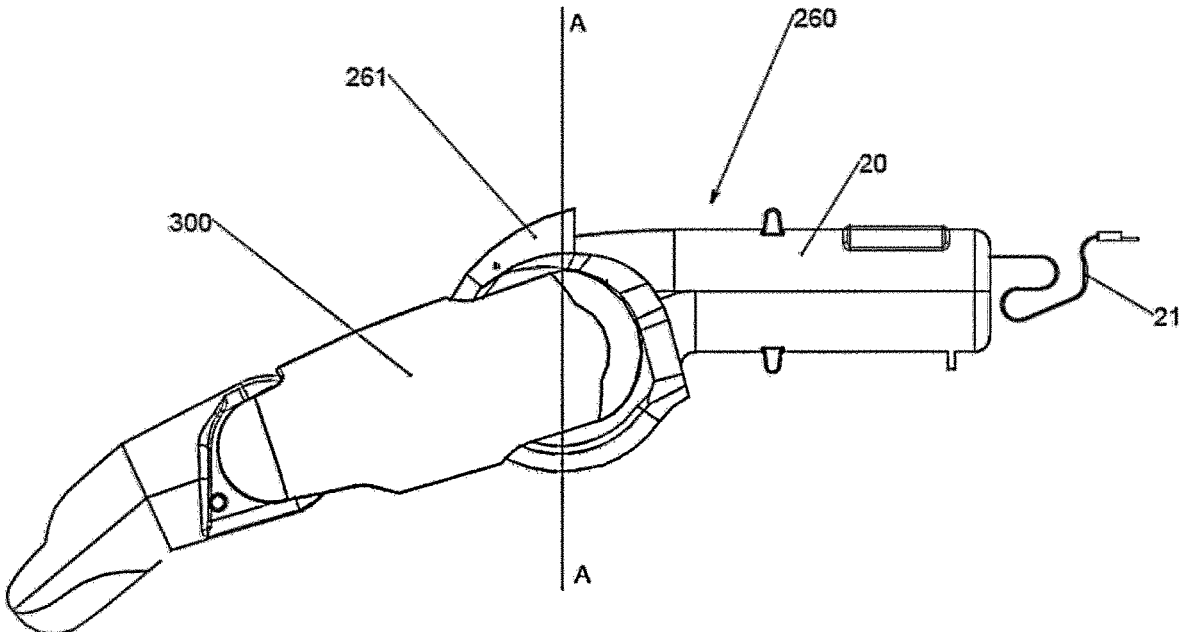
FIG. 10A is a side view of part of a digit and knuckle of the invention.
Figure 10B:
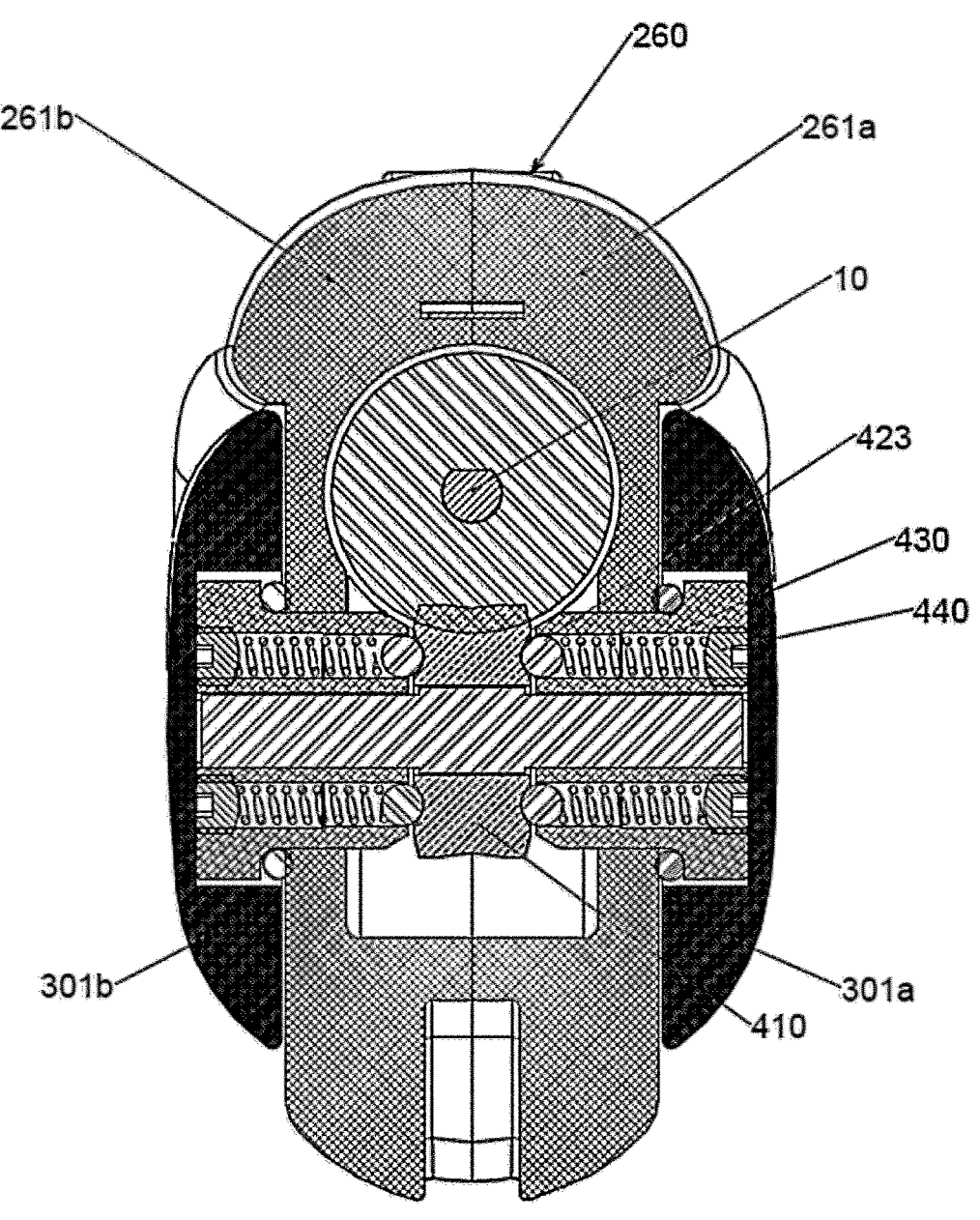
FIG. 10B is a cross-sectional view of one form of digit and clutch device taken along line A-A of FIG. 10A.
Figures 11A, 11B:
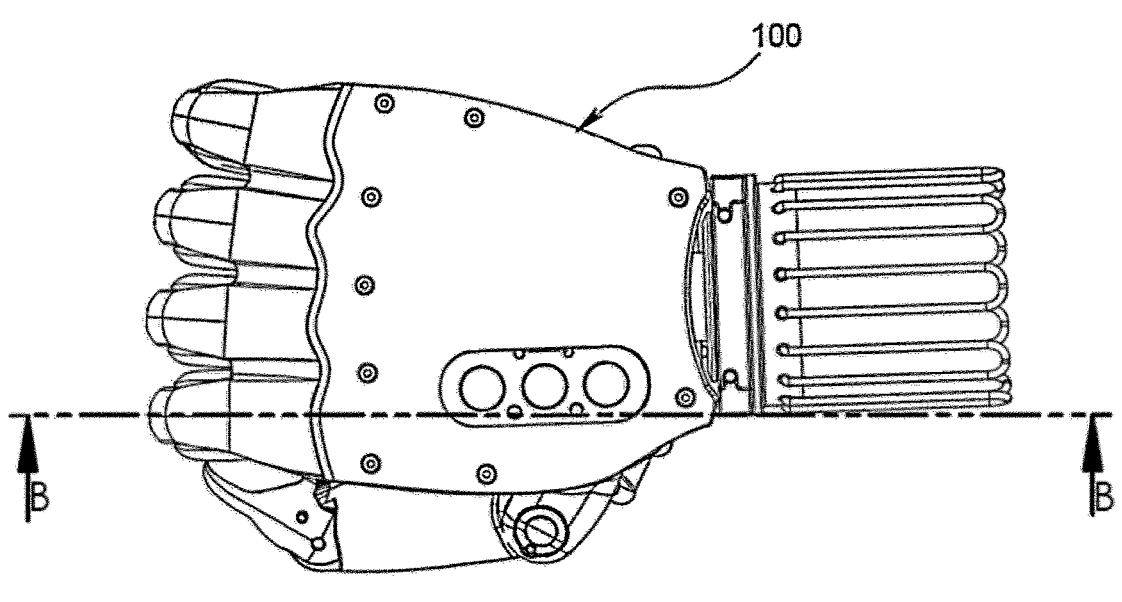
FIG. 11A is a plan view of one form of automated hand in a gripping position.
FIG. 11B is a cross-sectional side view of the hand taken along line B-B of FIG. 11A.

In another form, as shown in FIGS. 9, 10A, and 10B, the contact surface 411 of the driven element 410 comprises one or more female engagement members 413 and the clamping member 420 comprises one or more male engagement members 423. Each male engagement member 423 may be configured to be at least partially received in a respective female engagement member 413 to engage the driven element 410 and clamping member 420 with each other.

In one form, the first surface 421 of the clamping member 420 comprises one or more apertures 424. Each aperture 424 comprises a closed end and an open end. The open end is located at the first surface 421. The aperture 424 may be formed with a closed end. Alternatively, the aperture may extend between the first and second surfaces of the clamping member and a stop 440, such as a grub screw, may be placed in the aperture at the second surface to close the end of the aperture 424.

A compression member may be held within each aperture 424. A male engagement member 423 may be located at the open end of the aperture 424 to project, at least in part, from the first surface 421. In this arrangement, the compression member 430 is held within the aperture 424 between the male engagement member 423 and the closed end of the aperture 424. The projecting male engagement member 423 presses against the contact surface 411 of the driven element 410 and against the compression member 430. The compression member 430 is therefore held under compression within the aperture 424 and is configured to push the male engagement member(s) against the contact surface 411 of the driven element 410.

Optionally, the compression member 430 is a spring, but in other forms, the compression member may be formed from any substantially compressible, resilient material that is able to compress and then spring back to its original form.

In one form, the male engagement member 423 may comprise a ball, such as a ball bearing which is held under compression between the clamping member 420 and driven element 410.

The compression force of the compression member 430 presses the male engagement member, such as a ball bearing 423, against the contact surface 411 of the driven element 410.

As described above, the female engagement members 413 on the contact surface 411 of the driven element 410 may comprise one or more recesses 413 within which respective male engagement members 423 may nest when the driven element 410 and clamping member 420 are engaged. In this arrangement, the clamping member 420 is caused to rotate when the driven element 410 rotates. Where the male engagement member(s) comprise(s) a ball bearing, the one or more recesses 413 may be configured to allow a ball bearing 423 to rotate somewhat within a respective recess 413. In this configuration, the invention provides a spring-loaded ball bearing clutch device 400 that causes the clamping member 420 to rotate as the driven element 410 rotates.

The clamping member 420 also comprises a second surface 422, which may be configured to directly or indirectly engage with the finger 310. For example, the second surface 422 of the clamping member 420 may be configured to engage with a corresponding receiving element 305 formed in the body of the digit 300. In another embodiment, the distal end of the axle 450 may be configured to engage with a corresponding receiving element formed in the body of the finger. The second surface 422 of the clamping member 420 and/or the distal end of the axle 450 may form the second end of the clutch device 400. The receiving element 305 may be an opening such as an aperture, recess, or a non-recessed area defined by at least one wall that borders the non-recessed area or by a plurality of projecting arms that define the border of the non-recessed area. In one form, as illustrated, the clamping member 420 is configured to engage with the proximal phalanx 301 of a finger 310. In one form, the clamping member engages with the finger by being attached to or integral with the finger.

In one form, as shown in FIG. 9, the clamping member 420 may comprise a shaft 426 that comprises the first surface 421 of the clamping member 420. A flange 427 may be located at or near one end of the shaft 426. The flange 427 may comprise the second surface 422 of the clamping member 420. The shaft 426 may be configured to be held within the clutch receiving aperture 266 of the knuckle 261. In one form, the flange 427 of the clamping member 420 is configured to abut an outer mounting surface 265 of the knuckle body 261 so that the flange 427 is located on the outer surface 265 of the knuckle joint 261. In this arrangement, the shaft 426 of the clamping member 400 extends through at least part of the knuckle 261, such as the first part 261a, toward the driven element 410. The flange 427 of the clamping member 420 may be configured to engage with the finger 310, such as with the body of the proximal phalanx 301, as described above. For example, the flange 427 may be square shaped, hexagonal shaped, or irregularly shaped to key with a corresponding receiving element 305, such as a recess, aperture, or surround of the proximal phalanx.

In this configuration, when the clamping member is engaged with the driven element and the driven element is caused to rotate by the drive motor, the finger will be caused to rotate substantially simultaneously. The drive force between the drive motor and finger may be disconnected by disengaging the clamping member and driven element, as described later in this specification.

Figure 13:
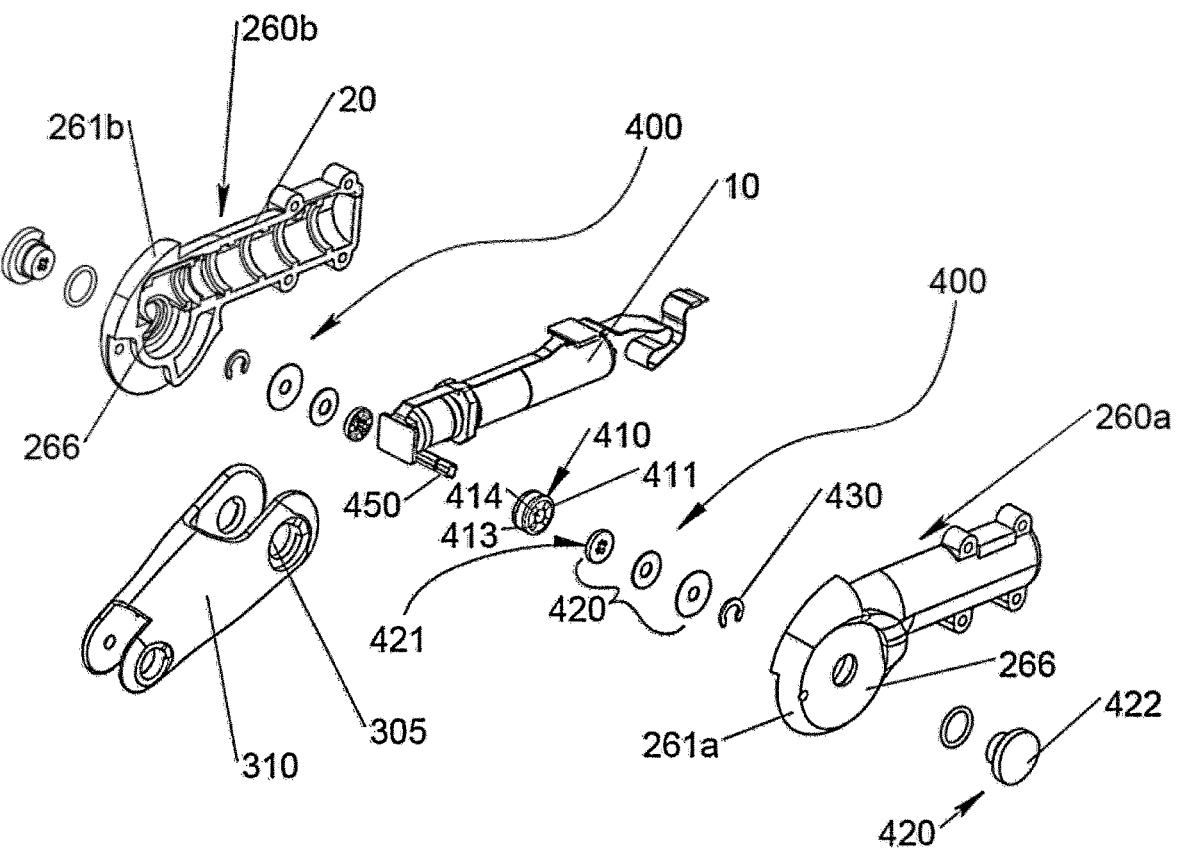
FIG. 13 is an exploded view of another form of clutch device of the invention.

In yet another form of clutch device, as shown in FIG. 13, the clamping member 420 comprises multiple parts, comprising a first element 420a comprising the first surface 421 of the clamping member 420 and a second element 420b comprising the second surface 422 of the clamping member. The compression member 430 may comprise a spring washer or the like and is configured to be located between the first and second elements 420a, 420b.

As above, the contact surface of the driven element 410 and the first surface 421 of the clamping member 420 may comprise one or more engagement members to engage the driven element with the clamping member. Again, the engagement members may be male engagement members comprising projections and female engagement members comprising openings, such as recesses, as described above. The contact surface of the driven element may comprise one or more male engagement members, female engagement members, or both, configured to engagement with corresponding female engagement members, male engagement members, or both located on the first surface of the clamping member.

In one form, one or more male engagement members 423 may project from the first surface 421 of the clamping member 420 to engage with one or more recesses 413 formed on the contact surface of the driven element 410. In another form, the driven element 410 comprises one or more male engagement members that project from the contact surface of the driven element and that are configured to engage with one or more recesses on the first surface of the clamping member 420.

The compression member 430 is configured to press the first surface 421 of the clamping member 420 against the driven element 410. The corresponding engagement members may therefore nest together to engage the driven element and clamping member with each other.

The second element 420b of the clamping member comprises the second end of the clutch. The second element 420b may be configured to engage with the finger 310. In this arrangement, when the driven element and clamping member are engaged, the clamping member and finger will rotate as the driven element rotates.

In one form, the second element 420b comprises a first end configured to extend between the clutch receiving aperture 266 of the first part of the knuckle joint 260a and to push against the compression member 430. A second end of the second element 420b is configured to abut the mounting surface 265a of the first part of the knuckle joint 260a and to engage with the finger 310, such as the proximal phalanx of the finger. Preferably, the finger 310 comprises a receiving element 305 that is configured to key with the second element of the clamping member 420, such as with the second surface 422 of the clamping member provided on the second element. The receiving element 305 may be located on an inner surface of the body of the finger 310. The receiving element 305 may comprise an aperture, recess, or area defined by at least one wall bordering the area or by a plurality of projecting arms.

Therefore, the clamping member 420 may be configured to engage with the driven element 410 and the respective digit 300 to transfer rotational movement of the drive motor 10 to the digit 300. As the drive motor 10 causes the driven element 410 to rotate, the engagement between the clamping member 420 and the driven element 410 causes the clamping member 420 to rotate and the finger is caused to rotate (curl or flex) also.

The clutch device 400 may be disengaged under certain conditions by disengaging the clamping member 420 from the driven element 410 to disconnect the drive motor 10 from the digit 300. This can be achieved by disengaging the first surface of the clamping member from the contact surface of the driven element. In one form, the male and female engagement members of the driven element 410 and clamping member 420 may be disengaged from each other to disengage these two parts 410, 420. For example, when the digit is in a curled or slightly curled configuration and is under tension from lifting a heavy weight or when the digit receives an end impact force, as shown by arrow "A" in FIG. 11B, the tension or impact force may cause the male engagement member(s) to be pulled or pushed out of the substantially shallow recesses to disengage the driven element 410 from the clamping member 420.

When disengaged, the driven element 410 may continue to rotate freely, but the disengaged clamping member 420 is no longer caused to rotate. Consequently, the finger 300 is also disengaged from the drive force of the motor 10. If the finger 300 was curled and lifting a heavy object at the time of disengagement, the finger may release its grip and extend to a substantially flexed position because the drive motor is no longer able to pull the finger into the curled position. Similarly, if the finger receives an end impact, the impact force will immediately allow the clutch to disengage so that the finger can buckle under the impact to at least partially absorb the impact force without damaging the drive motor.

Figure 12A:
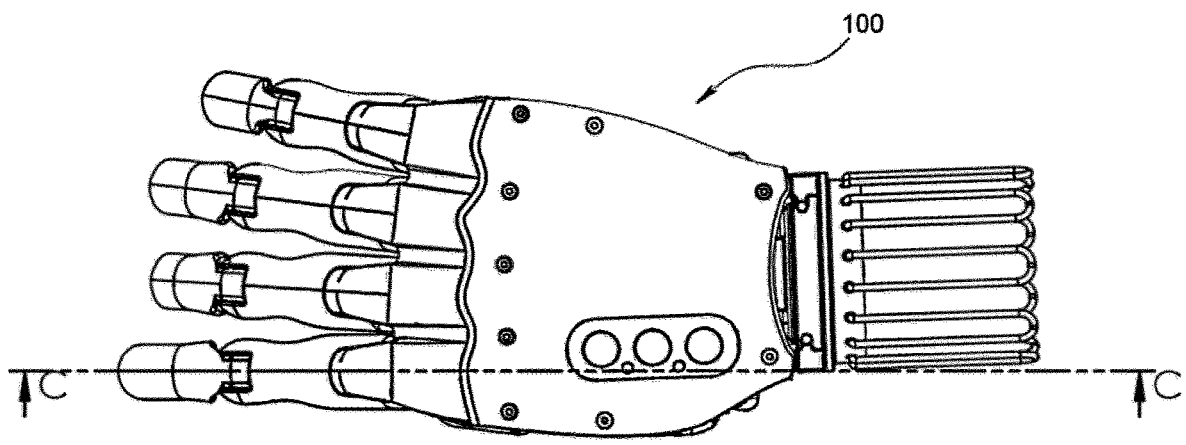
FIG. 12A is a plan view of one form of automated hand of the invention in an open position.
Figure 12B:
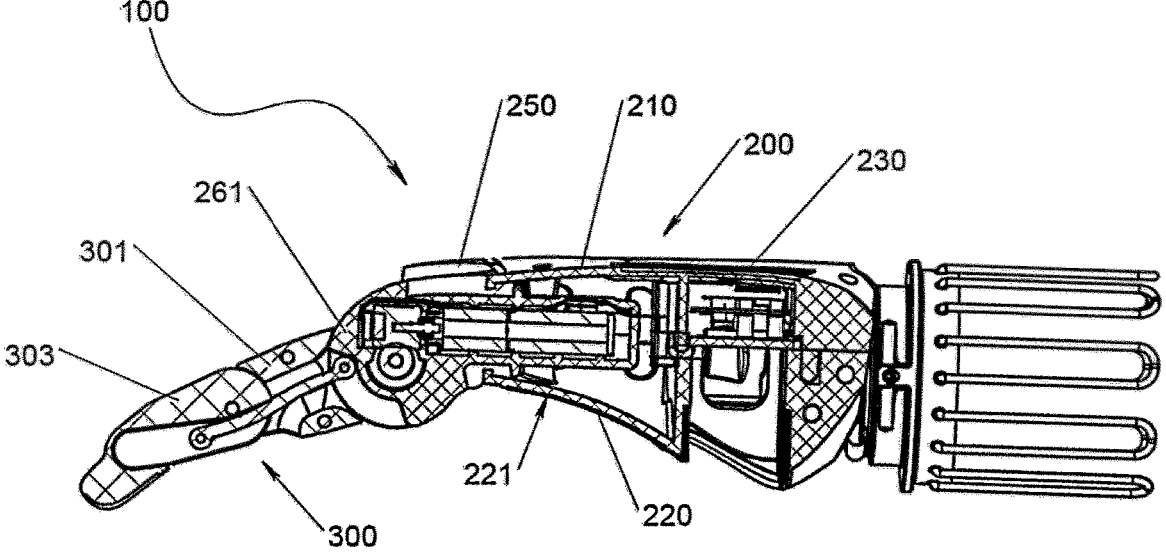
FIG. 12B is a cross-sectional side view of the hand taken along line C-C of FIG. 12A.

The disengaged digit 300 will become slack, as shown in FIG. 12A and 12B, and will need to be manipulated into an engaged position to re-engage with the drive motor 10.

The compression member continues to press the male engagement member(s) against the non-recessed area of the contact surface 411 of the driven element or the first surface of the clamping member, as the case may be.

Therefore, a user can realign the male engagement member(s) with respective female engagement member(s) by manually manipulating the digit 300 about the knuckle joint 261. The compression member 430 will automatically push the male engagement member(s) into the aligned female engagement member(s) to re-engage the clutch device 400 and finger 300 with the drive motor 10.

Figure 14A:
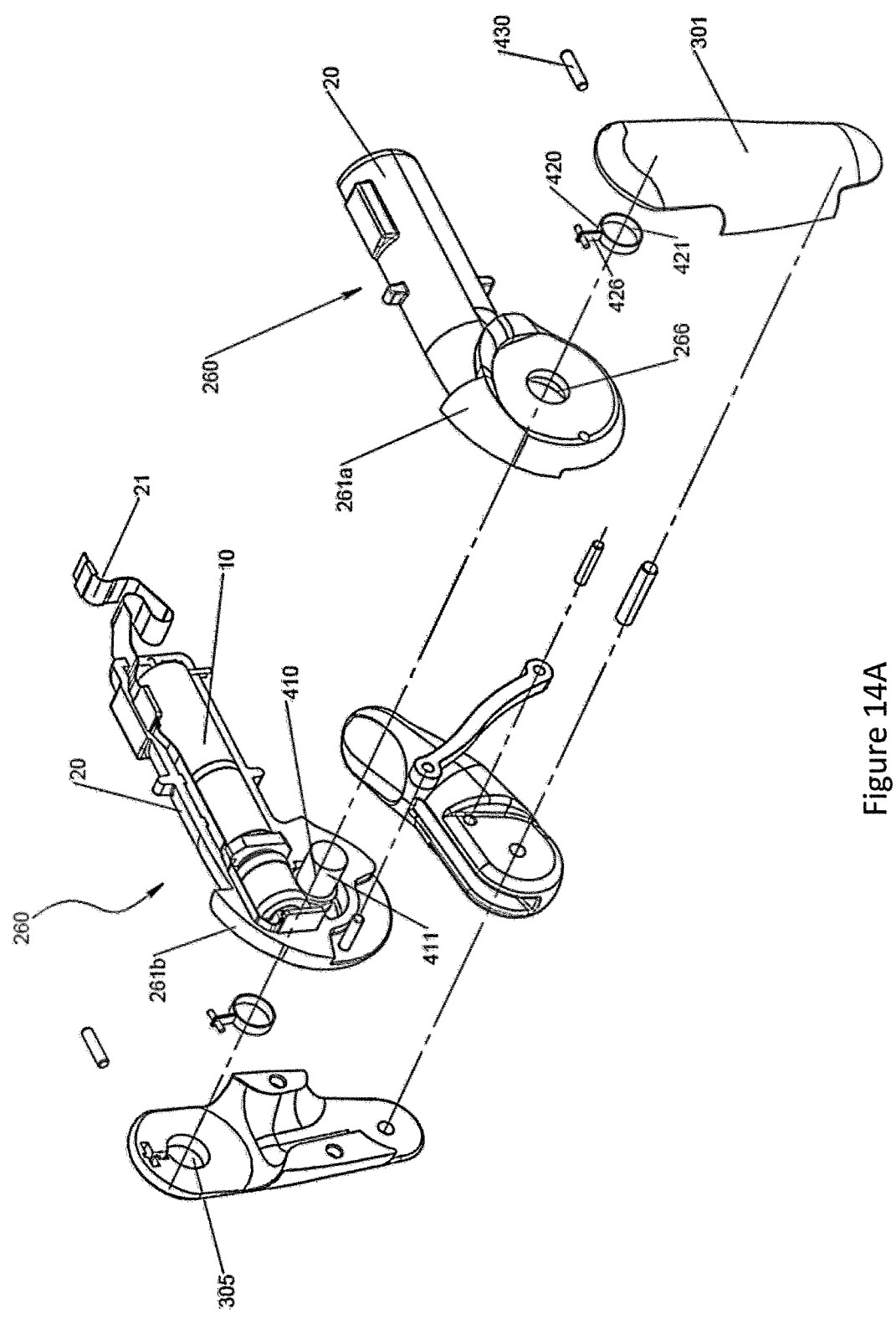
FIG. 14A is an exploded view of yet another form of clutch device of the invention.
Figure 14B:
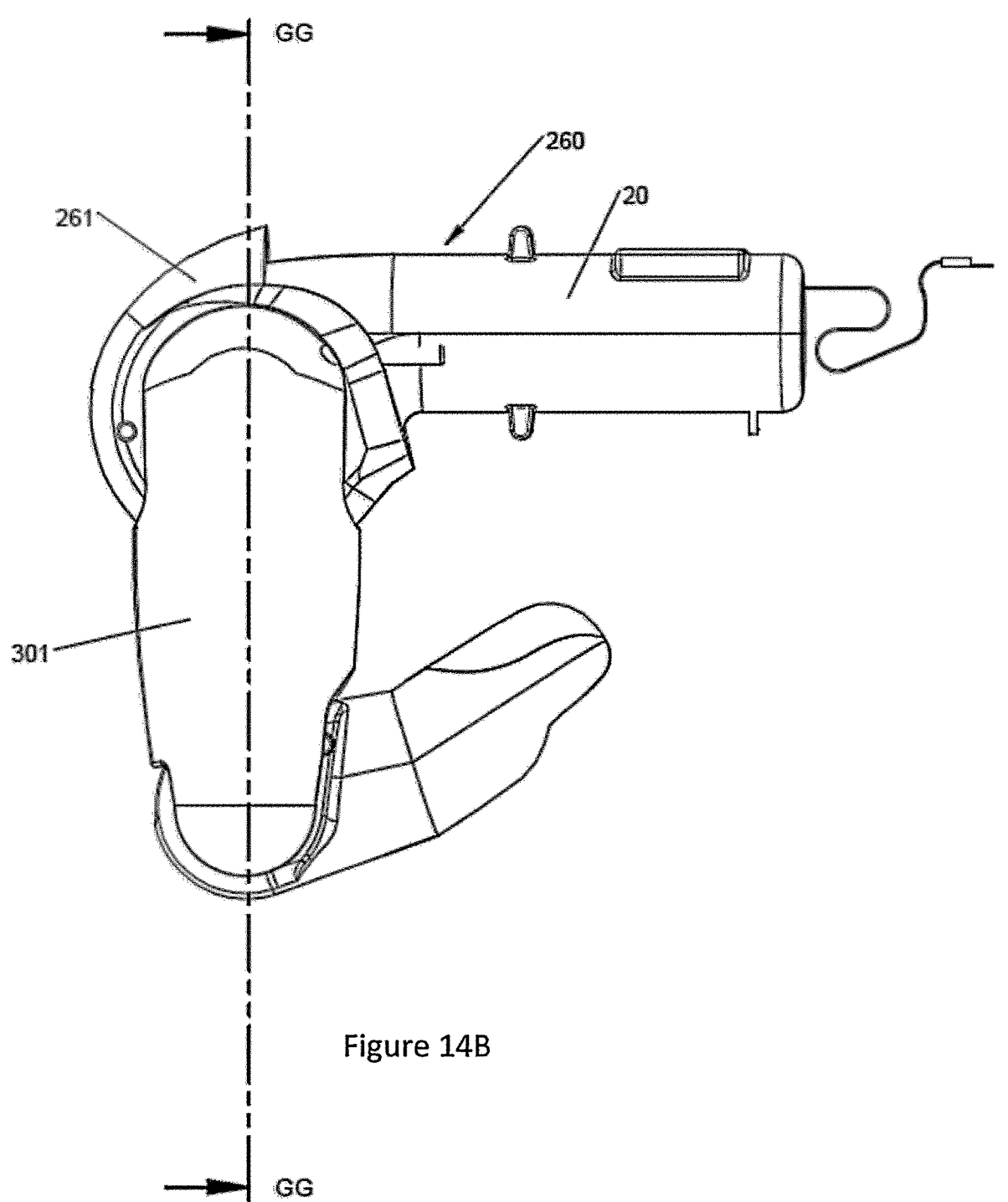
FIG. 14B is a side view of part of a finger bearing the clutch device of FIG. 14A.
Figure 14C:
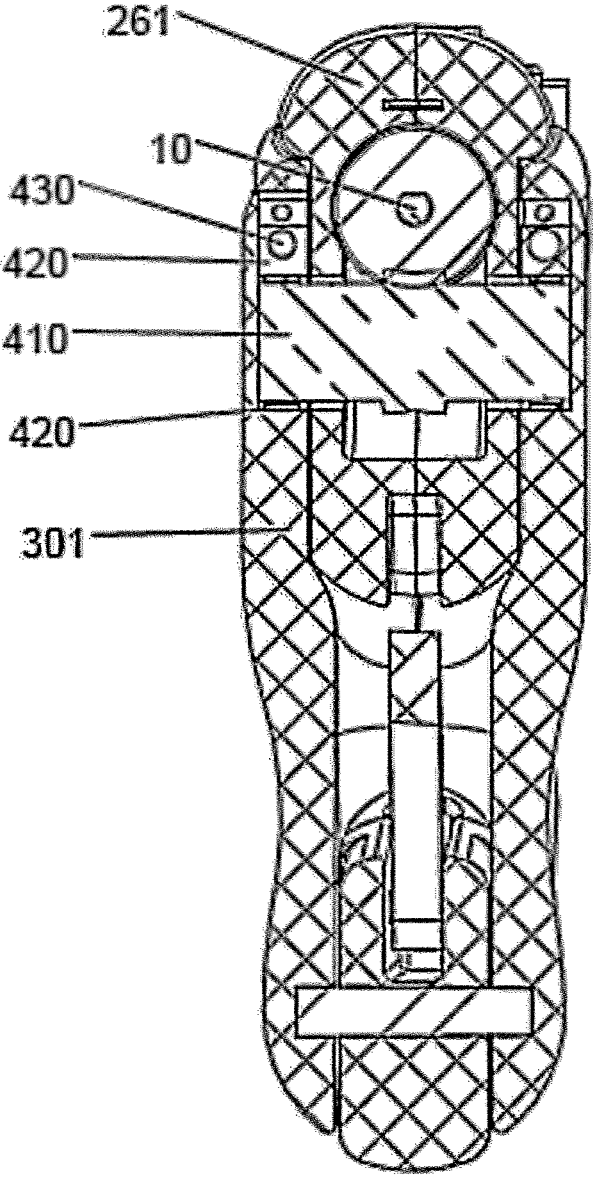
FIG. 14C is a cross-sectional view through line G-G of FIG. 14B.

In another form, as shown in FIGS. 14A to 14C, the contact surface 411 of the driven element 410 is substantially circular. For example, the driven element may be a disc shape or a cylindrical shape and the contact surface 411 may be the outer circumferential surface of the driven element 410. The clamping member 420 may comprise a body having two end portions 426 and a substantially concave inner surface 421 configured to wrap around at least a portion of the contact surface 411 of the driven element 410. Preferably, the inner surface 421 is configured to substantially surround at least half of the contact surface 411 of the driven element. The inner surface comprises the first surface 421 of the clamping member 420. In one form, the outer surface of the clamping member may form the second surface of the clamping member. In one form, the clamping member body is substantially u-shaped where the two end portions 426 of the clamping member 420 extend from the arms of the u-shaped body. In another form, the clamping member body is substantially circular to form a ring having two end portions 426 extending from the ring-shaped region of the body, as shown in FIG. 14A. Preferably, the two end portions 426 extend substantially perpendicularly from the clamping member body 420.

A compression member 430 is configured to press at least one of the end portions 426 against the other end portion 426 to tighten the clamping member body around the driven element so that the first surface 421 of the clamping member clamps against the contact surface 411 of the driven element.

The clamping member 420 may comprise the second end of the clutch device 400. The clamping member 420 may be configured to directly or indirectly engage with the finger 310, such as a receiving element located on the body of the finger. In one form, the clamping member may be configured to engage with the proximal phalanx of the finger.

The receiving element 305 may be located on an inner surface of the body of the finger 310. The receiving element 305 may comprise an aperture, recess, or area defined by at least one wall bordering the area or by a plurality of projecting arms. In one form, the receiving element 305 is configured to also receive at least a portion of the compression member therein so that the compression member can press against one or both of the end portions 426 of the clamping member 420. The receiving element 305 may be configured to key with the second surface of the clamping member 420.

In one form, the compression member 430 may comprise a screw that is screwed into the body of the finger 310 and against a first end portion 426a to push the first end portion toward the second end portion 426b. Optionally, the compression member 430 may comprise a pair of screws that are screwed into the body of the finger 310 from opposite sides so that both the first and second end portions 426 of the clamping member 420 are pushed toward each other within the receiving element 305.

By clamping the first surface of the clamping member against the contact surface of the driven element, the clamping member is caused to rotate as the drive motor rotates the driven element. Because the clamping member is engaged with the finger, the finger is also caused to rotate.

The clamping member may be disengaged from the driven element when a sufficiently large impact force impacts the end of the finger, when curled, or when the finger lifts a heavy object so that the finger is subjected to a sufficiently large pulling force. For example, a sufficiently large pushing or pulling force will overcome the friction forces between the clamping member and driven element so that the clamping member begins to slip around the driven element and therefore disengages from the driven element. In this way, the finger is disengaged from the drive motor to protect the drive motor from the large pushing/pulling force.

The above describes just some forms of clutch device that may be used to engage and disengage a digit from a drive motor. It should be appreciated that other forms of clutch device may alternatively be used.

The clutch device of the invention provides the automated hand with a safety feature that reduces the strain placed on the drive motors from excessively high forces.

Another advantage provided by the clutch device of the invention is that the digits of the hand are able to curl and flex according to the direction of the motor with minimal friction between the fingers, the clutch device, and the drive motor. Unlike conventional automated hands, the digits of the hand do not require springs to bias the digits to an open position. The springs of conventional automated hands are typically stiff, which slows the finger speed and wears the drive motors. Conversely, the clutch device of the invention allows the digits of the hand to move relatively quickly. Another beneficial effect is that the clutch device may allow the hand to obtain an improved gain from the drive motors. The clutch device also provides controlled opening of the hand through controlled movement of the fingers as the fingers flex. This is because the fingers are not subjected to a biasing force that pulls the fingers to a flexed position.

Wrist

In one form, the invention comprises a wrist joint configured to provide for compact flexion of the hand at the wrist joint. In another form, the invention comprises a wrist joint configured to provide for compact rotation of the hand at the wrist joint. Optionally, the wrist joint may be configured to attach to a conventional quick disconnect system that attaches the wrist of an electric terminal device (such as a powered hook or automated hand) to an arm member. In yet another form, the invention comprises a wrist joint configured to provide compact flexion of the hand and compact rotation of the hand.

In one form, as shown in FIGS. 15 to 24, the automated hand 100 of the invention comprises a wrist joint 500 attached to the palm of the hand and configured to attach to an arm member. The arm member may be a sleeve in which a user's stump is located when the automated hand is in use. Alternatively, the arm member may be a mechanical arm for example.

The wrist joint may comprise a positioning system configured so that the position of the palm may be adjusted relative to the arm member. For example, the wrist joint may be configured to provide vertical rotation of the hand.

In one form, the positioning system may comprise an axle, which may be attached to the palm and directly or indirectly attached to an arm member. The palm 200 is configured to rotate about the axle 520 so that the palm can curl and flex relative to the arm member. The axle is held within the shell of the palm to allow the arm member to reach as close as possible to the palm, which allows the wrist joint to be substantially compact.

Figure 15:
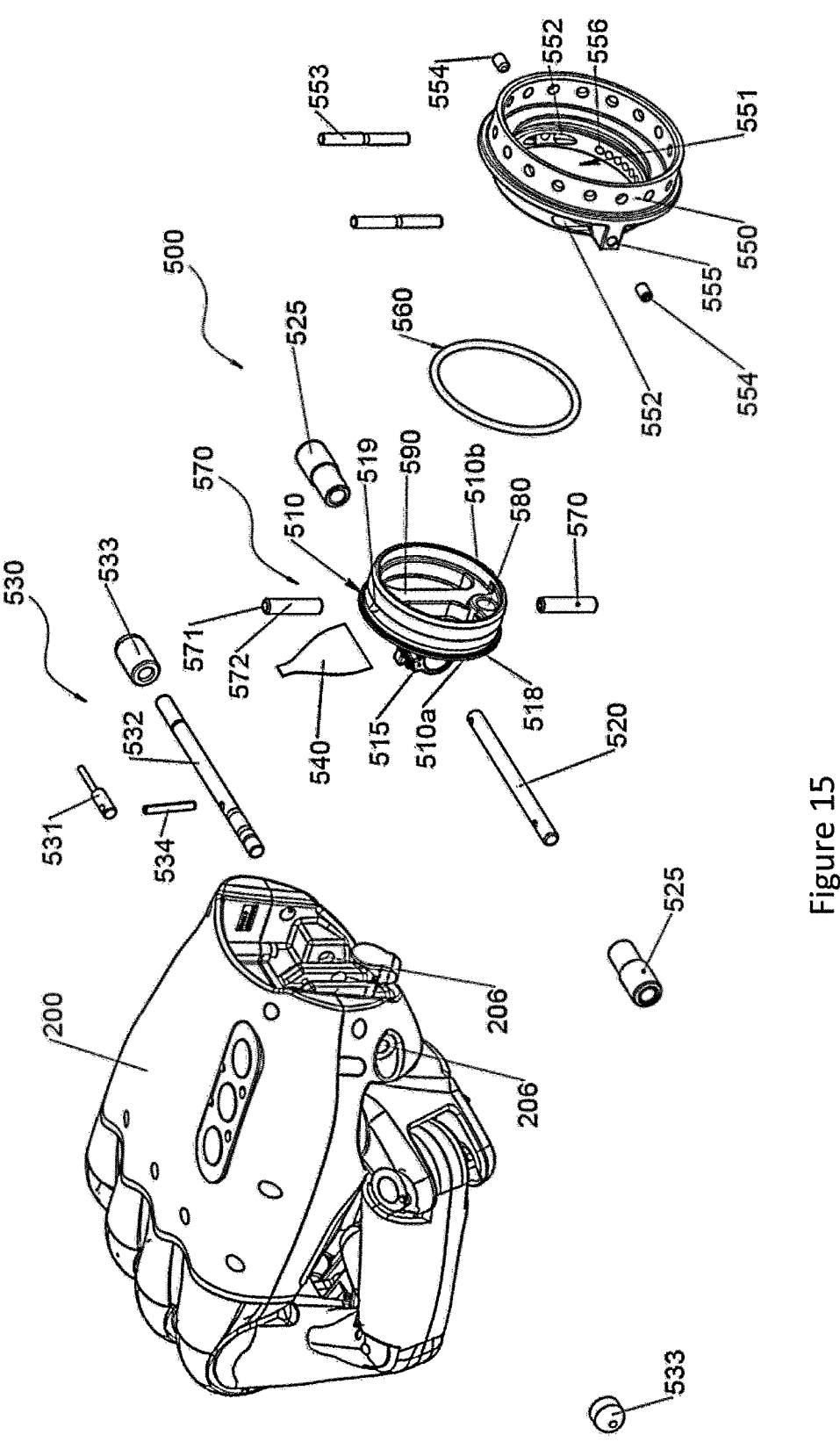
FIG. 15 is an exploded view of one form of wrist positioning system of the invention.

In another form, as shown in FIG. 15, the positioning system may comprise a positioning member 510, an axle 520, and a locking member 530. Preferably, the positioning system is substantially located within the palm. For example, the axle, locking member, and at least a portion of the positioning member may be located within the palm.

The axle 520 is connected to the palm 200. The palm 200 is configured to rotate about the axle 520 so that the palm can curl and flex relative to the arm member. For example, where the arm member extends horizontally to the ground and the contact surface 221 of the palm 200 faces the ground, the palm 200 is able to hinge upwardly (flex) and downwardly (curl) relative to the arm member.

In one form, the axle is configured to be held within the body of the palm of the hand. The axle 520 may substantially extend across the palm from the first side 201 of the palm to the second side 202. Each end 520a, 520b of the axle 520 may be rotatably attached to the palm 200. In one form, the base portion of the palm 200 may comprise a pair of substantially opposing openings 205a, 205b, which may be apertures, recesses, or the like, configured to receive the axle 520. The axle receiving openings may be provided in the interior of the palm or within the palm shell. In one embodiment, each axle receiving opening 205a, 205b is formed in the lower part 220 of the palm shell.

In one form, each end 520a, 520b of the axle may be supported by a substantially compressible axle mount 525. The substantially compressible axle mounts 525 provide the wrist joint with lateral impact cushioning, so that the hand may better withstand lateral impact forces.

In one form, each axle receiving opening may be formed in a substantially compressible material or may be lined by a substantially compressible material to form an axle mount. In another form, as shown in FIG. 15, substantially compressible axle mounts 525 are attached to each end of the axle 510 and may be supported within axle receiving openings 205a, 205b formed in the palm of the hand.

The positioning member 510 may be mounted on the axle 520 so that at least a portion of the positioning member is located within the palm.

The positioning member 510 may be configured to engage with the locking member 530 to lock the palm 200 in a desired position relative to the arm member.

Figure 16:
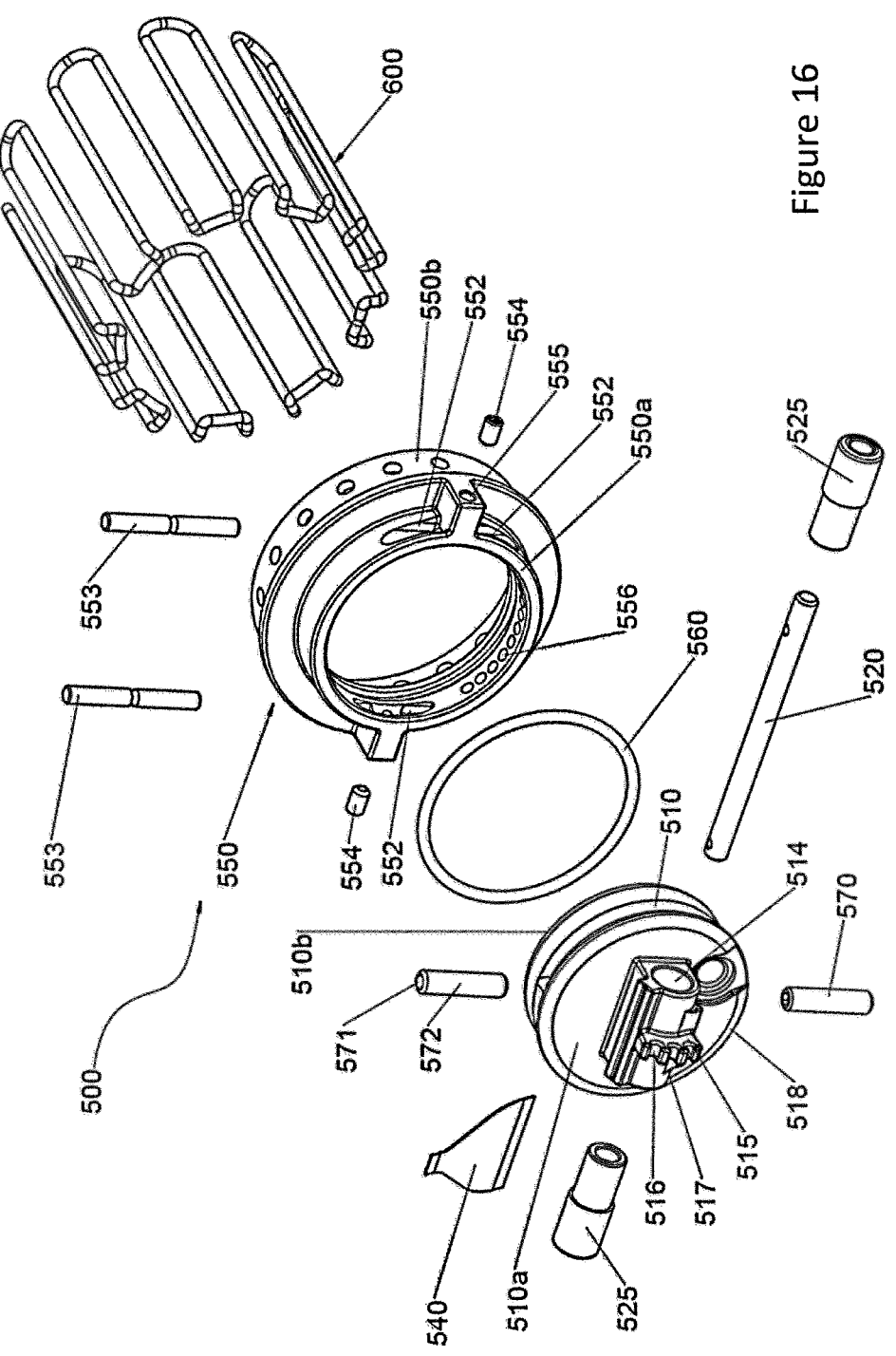
FIG. 16 is an exploded view of the wrist positioning system of FIG. 15 from another angle.

As shown in FIGS. 15 and 16, the positioning member 510 may comprise a body having a first end 510a that faces toward the palm and a second end 510b configured to face toward the arm member.

In one form, the positioning member 510 comprises an axle receiving aperture 514 for receiving the axle 520 therein. The axle receiving aperture may be formed at any suitable location on the body of the positioning member. In one embodiment, as shown best in FIG. 16, the axle receiving aperture 514 comprises a substantially hollow shaft located at or near the first end 510a of the positioning member. The axle 520 passes through the shaft 514 so that each end 520a, 520b of the axle extends beyond the shaft 514 and is supported within the palm by axle mounts 525, as described above.

The positioning member 510 may comprise one or more engagement elements configured to engage with the locking member 530.

In one form, the engagement element(s) may comprise at least one locking pin or opening configured to engage with one or more corresponding openings or locking pins of the locking member.

In one form, the positioning member 510 comprises a locking arm 515 on which one or more engagement elements 516 are located. The locking arm 515 may project from the first end 510a of the positioning member. In one form, the locking arm 515 is attached to or integral with the axle receiving shaft 514 and projects from the shaft 514. The locking arm 515 may project in a direction substantially perpendicular to the longitudinal direction of the axle 520. In this arrangement, the locking arm projects into the body of the palm of the hand.

In one form, the locking arm 515 comprises engagement elements in the form of one or more openings 516, which may be apertures, recesses, notches, or the like. In one form, the locking arm 515 comprises a first side 515a comprising a series of openings 516 formed in a curve so that each opening is equally spaced from the axle 520. In one form, the locking arm 515 comprises a convex edge 517 comprising a plurality of notches 516. The notches 516 are located substantially equidistant from the axle 520 to form a substantially curved line of openings/notches.

The openings 516 of the locking arm 515 are configured to be accessible to the locking member 530 so that the locking member may engage with the openings 516.

Figure 17A:
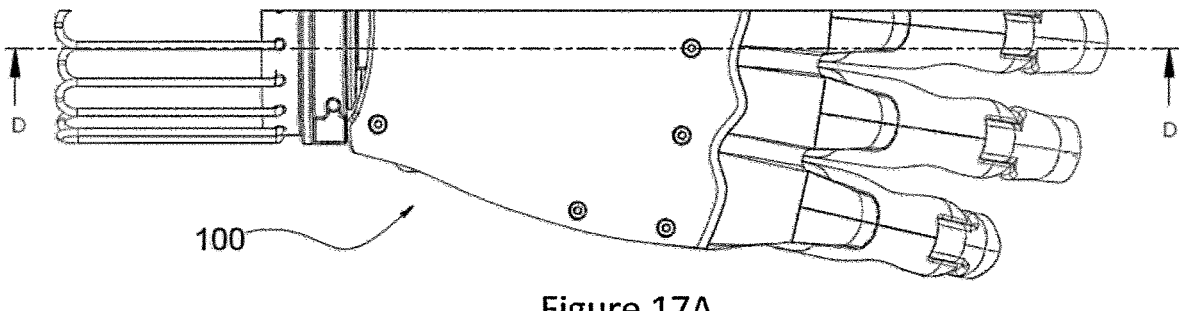
FIG. 17A is a partial plan view of one form of automated hand of the invention with a wrist in a neutral position.
Figure 17B:
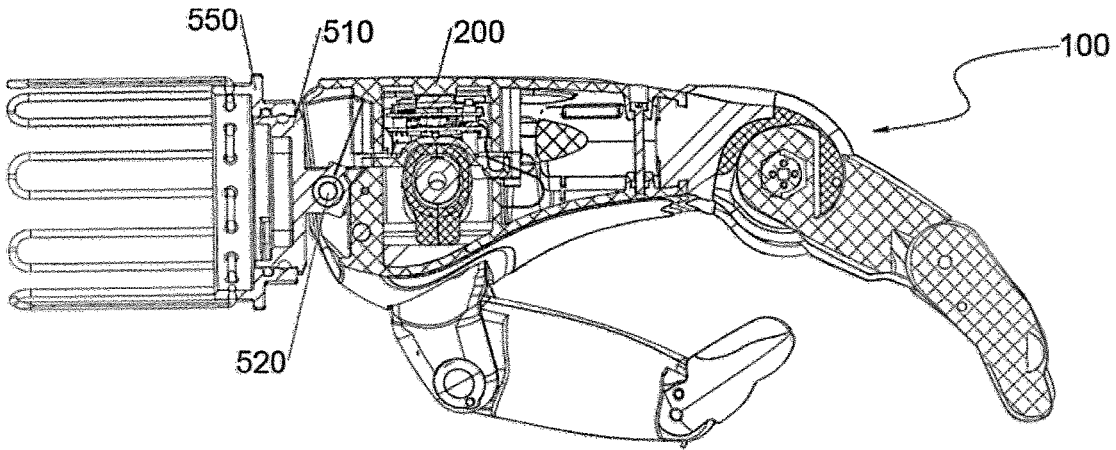
FIG. 17B is a cross-sectional side view of the hand taken along line D-D of FIG. 17A.
Figure 17C:
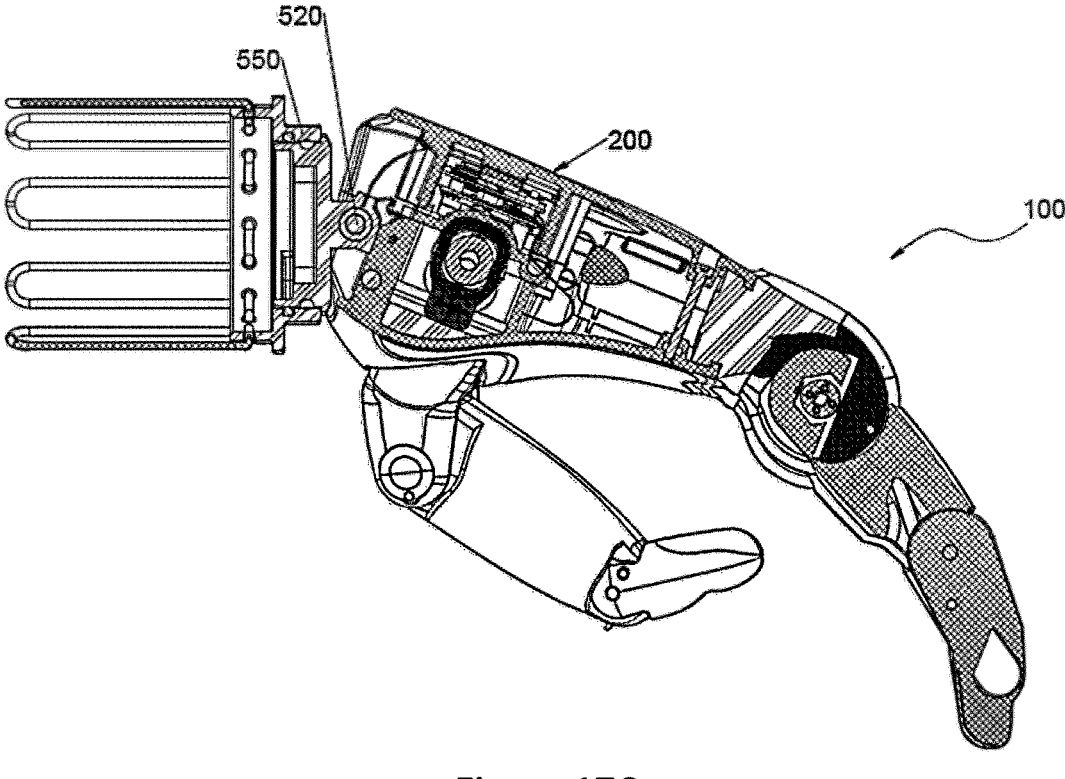
FIG. 17C is a cross-sectional side view of the hand taken along line D-D of FIG. 17A but in a curled position.
Figure 17D:
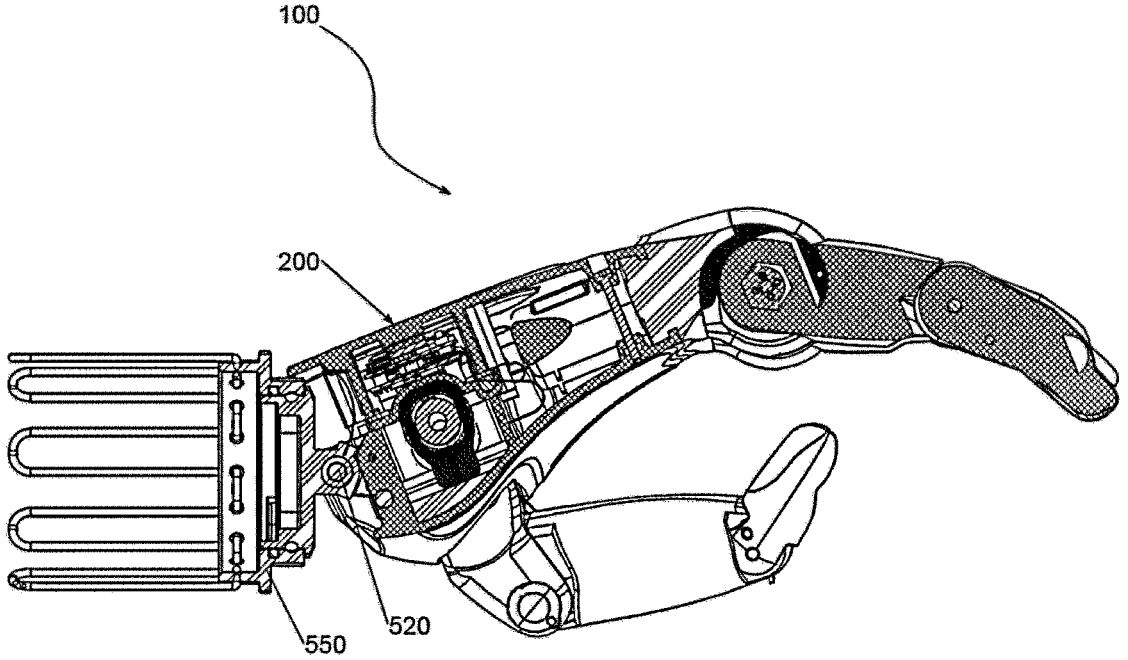
FIG. 17D is a cross-sectional side view of the hand taken along line D-D of FIG. 17A but in a flexed position.

The positioning member and locking member are configured to engage with each other to lock the palm in a particular position relative to the arm member. For example, the positioning system may lock the hand in: a neutral position in which the palm and arm member may be substantially aligned, as shown in FIGS. 17A and 17B; a curled position, in which the palm angles downwardly in relation to the arm member, as shown in FIG. 17C; and a flexed position, in which the palm flexes upwardly in relation to the arm member, as shown in FIG. 17D. These positions are described as if the user is holding the arm member substantially horizontally in front of his or her body with the palm of the hand facing down. However, the terminology is used for ease of understanding only and is not intended to limit the scope of the invention.

Figure 18:
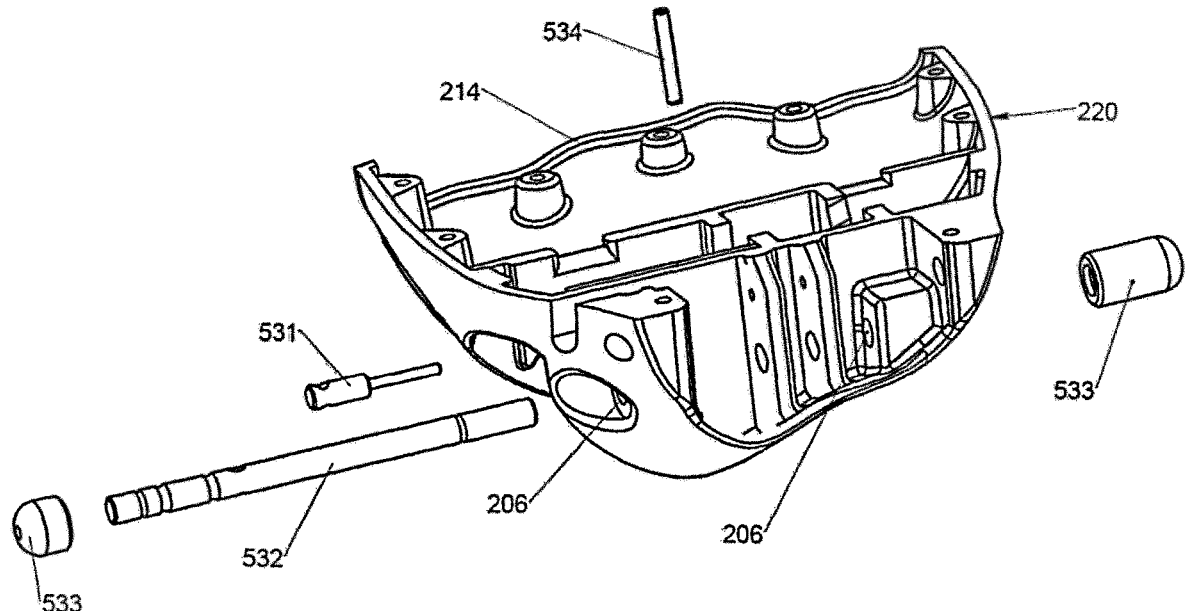
FIG. 18 is an exploded view of the lower part of the palm and switch of one form of the invention.
Figure 19:
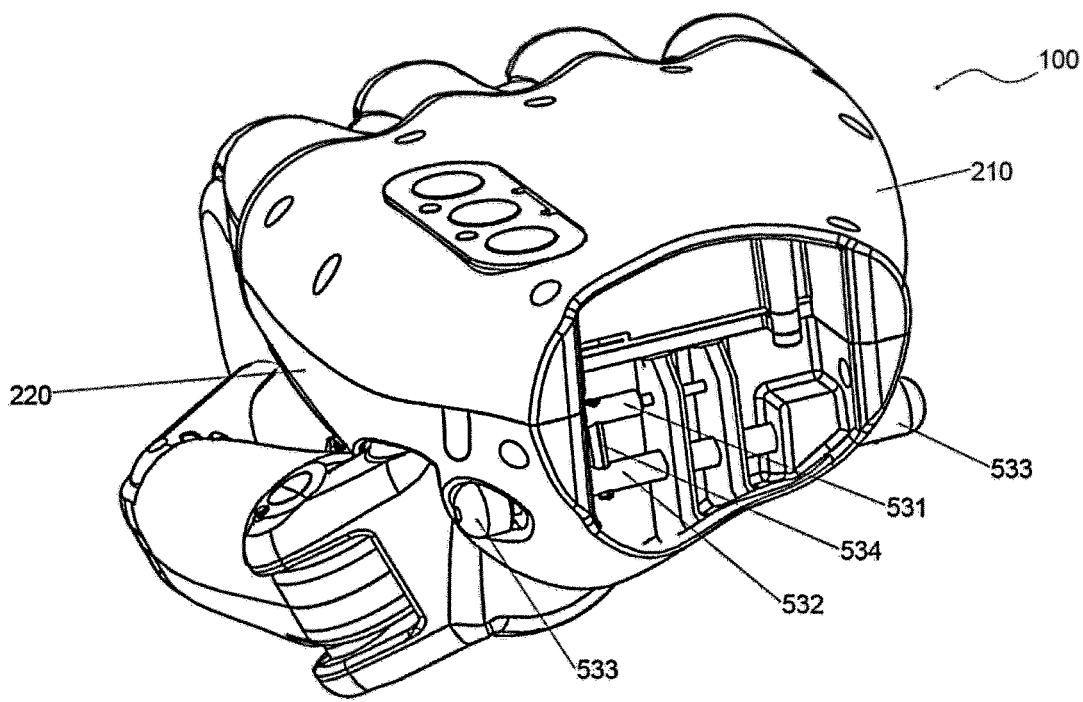
FIG. 19 is a perspective view of part of one form of automated hand of the invention.

In one form, as shown in FIGS. 18 and 19, the locking member 530 is attached to and located within the palm 200 of the hand. The locking member comprises a locking pin 531 configured to engage with any one of the openings 516 of the locking arm 515. The locking pin 531 may project toward the openings 516 of the locking arm. The locking pin may be configured to move toward the locking arm 515 so that the locking pin is received in one of the openings 516 to lock the locking member 530 and positioning member 520 together. In this arrangement, the locking pin 531 locks the palm 200 in a fixed position. The palm may be locked in any one of a number of desired positions by engaging the locking member 530 with any one of the engagement elements 516 of the positioning member 510. The locking pin 531 may also be configured to move away from the locking arm 515 so that the locking pin is retracted from the respective opening 516 to disengage the locking member 530 and positioning member 520 and allow the palm to curl and flex freely.

The positioning system may comprise a switch configured to switch the positioning system between a first mode and a second mode. In the first mode, the positioning system is configured to lock the palm in any one of a variety of positions in relation to the wrist joint, as described above. In the second mode, the positioning system is configured to allow the palm to hinge freely from the wrist joint between two points of maximum movement; one point being a position of maximum flex and the other point being a position of maximum curl.

In one form, the locking member 530 comprises the switch.

The switch is configured to move the locking pin 531 toward the positioning member (to engage with the positioning member) and away from the positioning member (to disengage from the positioning member).

In one form, as shown in FIGS. 18 and 19, the switch comprises a sliding arm 532 that extends across the interior of the palm shell from the first side 201 of the palm to the second side 202.

The shell of the palm 200 may comprise substantially opposing apertures in which the sliding arm may be located. In one embodiment, the lower part of the palm comprises a pair of substantially opposing apertures 206 located on each side 201, 202 of the palm. The apertures 206 may be configured to form channels in which the ends of the sliding arm 532 are located. The sliding arm may be configured to slide back and forth within the channels.

A stopper 533 may be provided at each end of the sliding arm 532. The apertures 206 may be configured to allow the sliding arm 532 to slide freely within the apertures 206 but to prevent the stoppers 533 from pulling out of the apertures 206 and into the interior of the palm 200. For example, the diameter of the apertures 206 facing the interior of the palm 200 may be larger than the diameter of the sliding arm 532 but smaller than the diameter of the stoppers 533, as shown in FIG. 19.

The locking pin 531 is attached to the sliding arm 532. For example, the locking pin 531 may be attached to or integral with the sliding arm 532. The locking pin 531 may extend substantially in the longitudinal direction of the sliding arm 532 and may be spaced from the sliding arm 532 by a spacer 534. Preferably, the locking pin 531 is configured to lie substantially parallel to the sliding arm 532.

To lock the hand 100 in a desired position relative to the arm member, the palm 200 is rotated about the axle 520 until it reaches the desired position. The stoppers 533 may serve as buttons of the switch so that the first button 533a may be pushed in a first direction to cause the sliding arm 532 to slide toward the other side of the palm 200. The locking pin 531 is simultaneously caused to move toward the positioning member 510 to engage with an opening 516 of the locking arm 515. The palm 200 of the hand is now locked in position relative to the positioning member 510 and arm member. The palm 200 is unable to rotate about the axle 520 in this locked position.

To unlock the hand 100 from a fixed position, the second button 533b is pushed in a second direction, opposite the first direction, to cause the sliding arm 532 to move toward the other side of the palm 200. The locking pin 531 is therefore caused to move away from and disengage from the respective opening 516 in the locking arm 515. In the unlocked/disengaged position, the palm 200 is able to hinge freely about the axle 520 between a position of maximum flex and a position of maximum curl. The maximum limits of movement may be provided by stops within the palm 200 that abut the positioning member 510 or axle to prevent the palm 200 from curling or flexing further in relation to the positioning member 510.

Figure 20A:
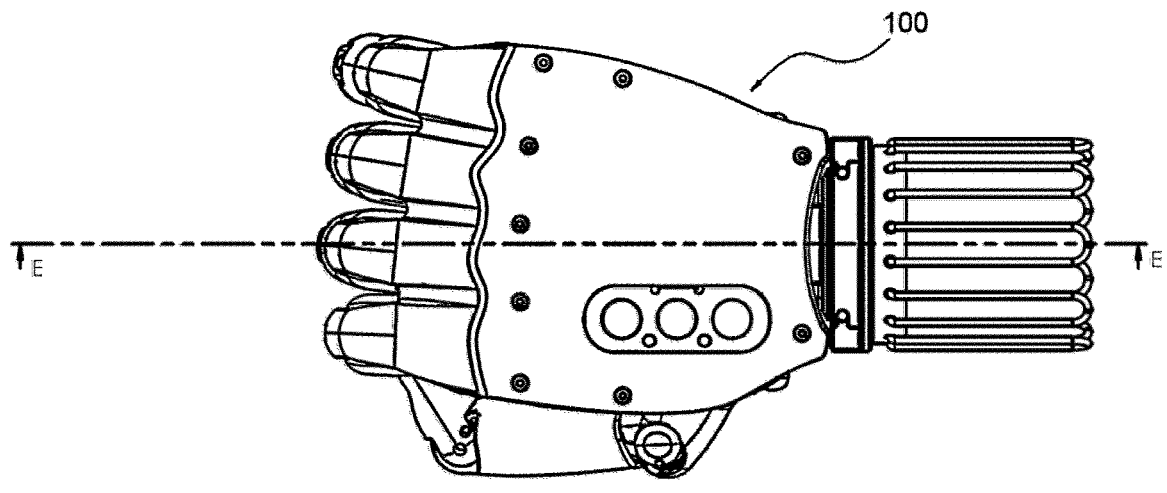
FIG. 20A is a plan view of one form of hand of the invention with the palm in a neutral position.
Figure 20B:
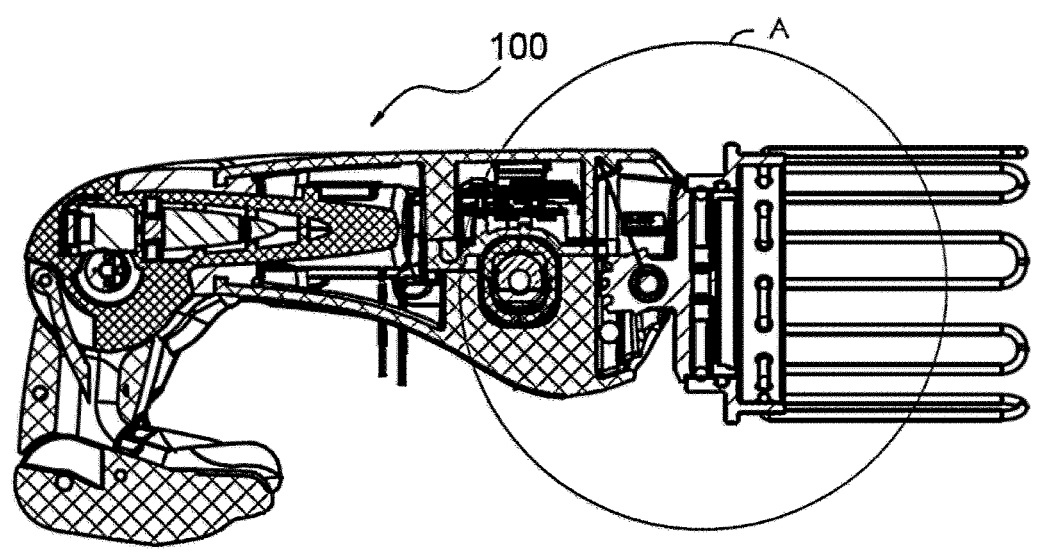
FIG. 20B is a cross-sectional side view of the hand taken along line E-E of FIG. 20A.
Figure 20C:
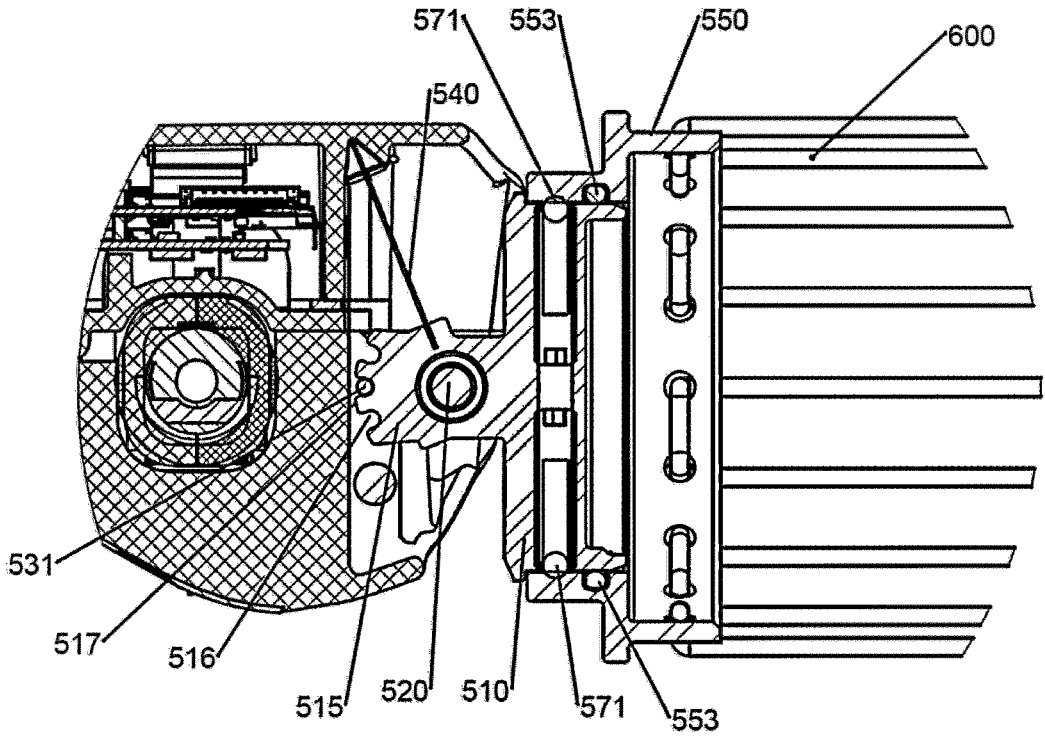
FIG. 20C is an enlarged view of area A of FIG. 20B.

In one form, the wrist joint comprises a tension member 540 to hold the palm 200 under tension. In this configuration, the palm 200 may hinge freely about the axle 520 without being substantially floppy. The tension member may extend from the positioning member 510 and press against or engage with the palm 200. In one form, as shown in FIGS. 20A to 20C, the tension member 540 comprises a leaf spring that extends from the locking arm 515 of the positioning member 510 and presses against an inner surface of the palm.

In one form, the positioning system of the wrist joint may comprise a connector 520 configured to connect the hand to an arm member. The connector 520 may be configured to attach the palm 200 to an arm member to allow the palm to rotate left and right relative to the arm member.

For example, in one form, the positioning system may comprise a positioning member 510, an axle 520, a locking member 530, as described above, and a connector 550.

The connector 550 comprises a body having a first end 550a and a second end 550b. The first end of the connector faces toward the palm of the hand and the second end is configured to face toward the arm member. In one form, the connector comprises a receiving aperture 551 that extends between its first and second ends 550a, 550b. Preferably, the connector is substantially ring shaped or tubular such that the connector comprises an opening into a substantially hollow body of the connector.

The positioning member 510 is configured to engage with the connector 550 in a rotating arrangement, such that the positioning member may rotate relative to the connector, which may be attached to the arm member in a fixed position.

In one embodiment, the second end 510b of the positioning member 510 has a substantially circular periphery configured to fit within a substantially circular receiving aperture 551 at the first end 550a of the connector 550. In one form, the positioning member 510 comprises a substantially cylindrical or conical body. The interior of the positioning member body 510 comprises an opening 590 so that the positioning member is substantially hollow. In one form, the interior of the positioning member body forms a substantially hollow tube.

The positioning member may be attached to the connector in any suitable arrangement. For example, the second end of the positioning member may be threaded to engage with a threaded first end of the connector. In another form, fasteners may be used to attach the positioning member and connector together. In a preferred form, fasteners are used to attach the positioning member and connector together without encroaching into the substantially hollow interior of the positioning member.

Figure 21:
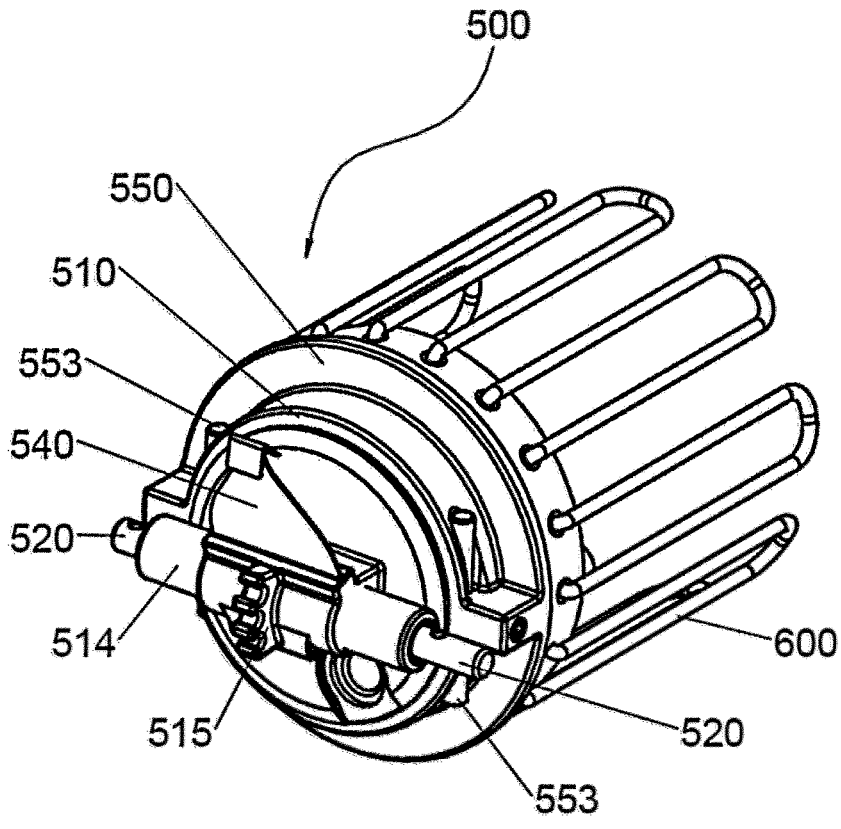
FIG. 21 is a perspective view of one form of positioning member attached to one form of connector according to the invention.

In one form, as shown in FIGS. 15 and 16, the positioning member 510 comprises a flange 518 that projects from the body of the positioning member 510. The flange is preferably positioned at or near the first end of the positioning member. At the first end 550a of the connector, the receiving aperture 551 is configured to have a diameter smaller than the diameter of the flange 518. The positioning member 510 may be attached to the connector 550 by locating the second end 510b of the positioning member within the receiving aperture 551 of the connector so that the flange abuts the first end 550a of the connector, as shown in FIG. 21. Fasteners may then be used to hold the positioning member in loosely in place within the connector so that the positioning member is able to rotate within the connector but is unable to separate from the connector.

In one form, as shown in FIG. 15, 21, 22A and 22B, a pair of adjacent holes 552 are provided on substantially opposing sides near the first end 550a of the connector. A fastener comprising a pin 553 is configured to extend between each pair of holes 552. Each pin 553 may be configured to clamp against the sides of the positioning member body 510. In one form, compression members 554, such as spring loaded projections, grub screws, or any other suitable system, may be configured to extend through holes 555 in the side wall of the connector 550 to press against the pins 553 and cause the pins 553 to loosely clamp against the positioning member 510. Optionally, the pins 553 may comprise a receiving element against which the compression members may press.

An advantage of using a spring loaded compression member is that the pins 553 press firmly against the body of the positioning member to hold the positioning member in place. However, of sufficient rotational force is applied to the palm, the positioning member may be caused to overcome the compression forces and frictional forces applied by the pins 553 to rotate relative to the connector. In this way, the fasteners automatically release and re-engage when the sufficient rotational force is removed.

An advantage of attaching the positioning member to the connector with fasteners that do not encroach on the interior surface of the positioning member, the wrist joint maximises the space in which the stump of a user's hand may project into the wrist joint. This allows the overall length and configuration of the arm member, wrist and hand to appear substantially anatomically correct.

However, this is just one arrangement in which the positioning member 510 may be attached to the connector 550. As will be appreciated, the two parts 510, 550 may be attached together in any suitable arrangement. For example, in an alternative form, the first end of the connector may instead be configured to fit within the second end of the positioning member.

The positioning member 510 may comprise at least one locking finger 570 configured to project from an outer surface of the positioning member body and to engage with an inner surface of the connector. Preferably, the positioning member comprises two locking fingers 570. In one form, as shown in FIG. 23B, each locking finger may form a spring loaded projection. For example, the locking finger may comprise a nib 571, such as a ball or ball bearing, that is held within a chamber 572 that may be formed in the body of the positioning member 510 or that may fit within an aperture 519 formed in the body of the positioning member. A biasing member, such as a spring, may be located between the nib 571 and a closed end of the chamber 572. The nib 571 projects from an open end of the chamber 572 and is clamped between the free end of the compressed spring and the inner surface of the receiving aperture 551. The connector 550 may comprise a plurality of indexing nodules 556, in the form of apertures or recesses, on its inner surface. The indexing nodules 556 may extend in a line around the inner surface of the receiving aperture 551 of the connector near the first end 550a of the connector. The nib 572 is configured to engage with any of the indexing nodules 556. However, with sufficient force, the positioning member 510 may be rotated within the connector 550 so that the compressed spring compresses further and the nib 572 is pushed out of its respective indexing nodule 556 and into the adjacent nodule. In this way, the palm 200 may be rotated laterally to cause the positioning member 510 to rotate within the connector 550. When the palm 200 reaches a desired position, the compressed spring pushes the nib 572 into the respective indexing nodule 556 to lock the palm in position. Preferably, the positioning system is configured so that the palm may rotate up to 45 degrees left and right.

Therefore, the positioning system may be configured to allow the palm to curl and flex and/or to rotate laterally.

In another form, the wrist joint is configured to attach an electric terminal device (such as a powered hook or automated hand) to an arm member. In one form, the wrist joint may comprise a body comprising a first end configured to face toward the electric terminal device and a second end configured to face toward the arm member. The wrist joint may also comprise an aperture extending into a substantially hollow region of the wrist joint body to allow a portion of a user's stump to extend through at least a portion of the wrist joint. Optionally, the aperture extends between the first and second ends of the wrist joint. For example, in one form, the body of the wrist joint may be substantially tubular or ring shaped. The wrist joint may further comprise an axle that is rotatably attached to the palm to allow the palm to hinge relative to the wrist joint.

Figure 24:
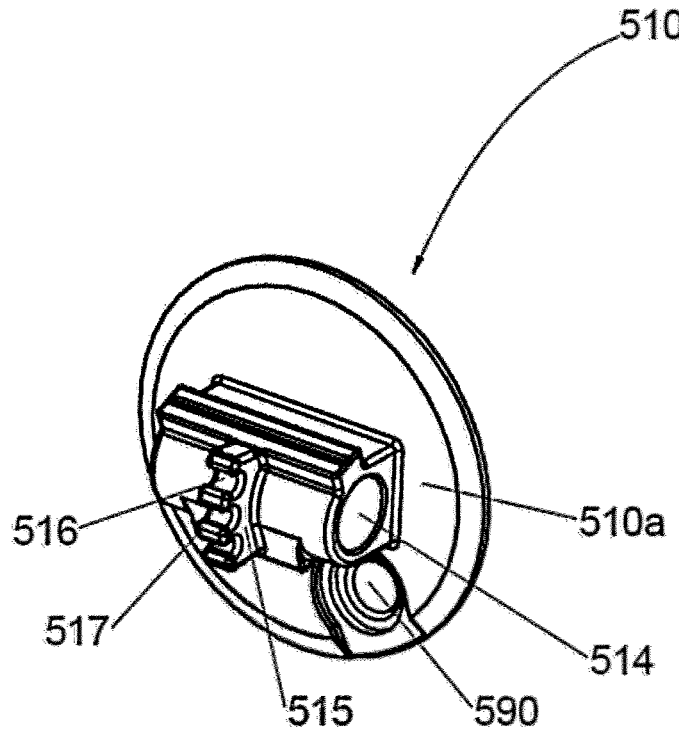
FIG. 24 is a perspective view of another form of positioning member of the invention.

In one form, as shown in FIG. 24, the wrist joint comprises a positioning member 510 comprising a substantially planar body. The positioning member may be configured to attach to a connector 520 to form the body of the wrist joint. The positioning member and/or connector may be attached to an arm member to attach the wrist joint to a user's arm. In one form, the second end 510b of the positioning member may comprise a substantially smooth surface. The positioning member may be attached to an arm member comprising or in the form of a quick disconnect wrist system, such as those known in the art. The positioning member and arm member may be attached together in any suitable way, such as by using fasteners, such as screws, or adhesive, or any other suitable form of attachment. Preferably, the second end 510b of the positioning member is screwed or bolted onto an end of an arm member, such as a quick disconnect wrist system. In one form, the connector may be located between the second end of the positioning system and the distal end of the arm member so that the connector is also attached to the arm member when the positioning member and arm member are attached together. In this arrangement, the connector is clamped between the positioning member and arm member. The positioning member is unable to rotate relative to the connector. Optionally, the arm member/quick disconnect wrist system comprises a rotating end to allow the palm to rotate left and right relative to the arm member. Therefore, the positioning system of the wrist joint may be configured to attach the palm to a conventional arm member or to a proprietary arm member.

Optionally, the positioning member and connector are formed as a single part.

The wrist joint may comprise a cable port 580 in which electrical connectors may be located to connect the palm to the arm member. For example, the positioning member and connector may each comprise substantially aligned apertures to form a cable port between the palm and arm member.

Figure 23:
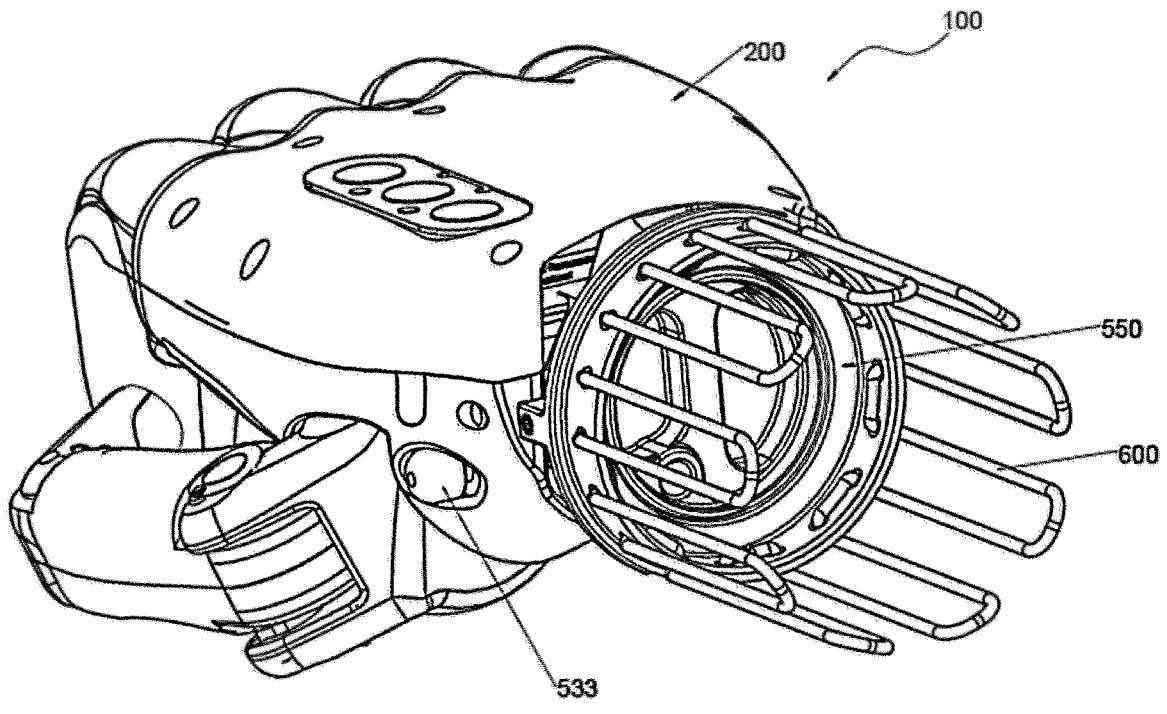
FIG. 23 is a perspective view of one form of automated hand comprising a wrist joint according to one form of the invention.

As shown in FIGS. 21 and 23, the second end of the connector 550 may comprise a sleeve attachment system 600 to attach the automated hand to an arm member in the form of a sleeve that fits over a user's stump.

An advantage of the wrist joint of the invention is that because at least a substantial portion of the positioning system is housed within the palm of the hand, the wrist joint takes up very little space between the arm member and the palm of the hand. Consequently, when the hand is used as a prosthetic, the wrist joint and the connection between the palm and arm member appear to be substantially anatomically correct.

Figure 22A:
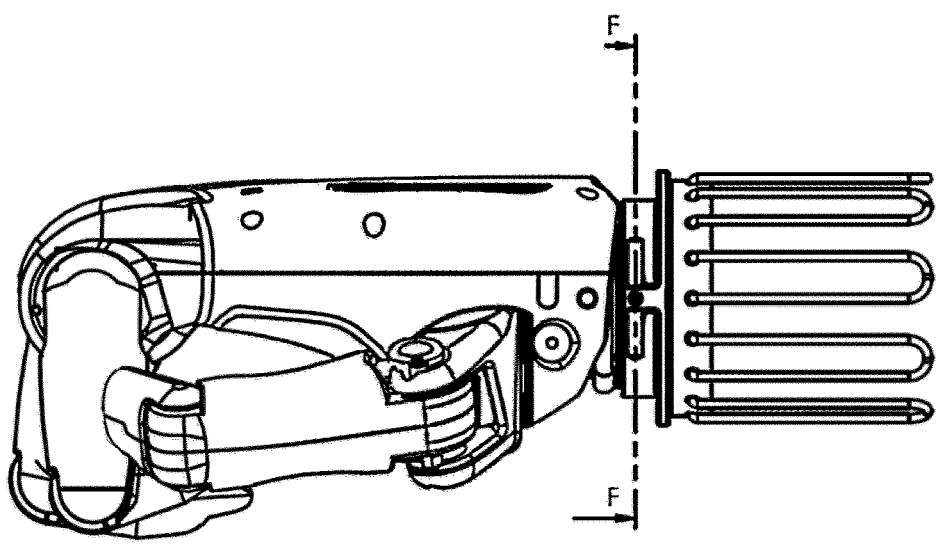
FIG. 22A is a side view of one form of hand with wrist joint in a neutral position.
Figure 22B:
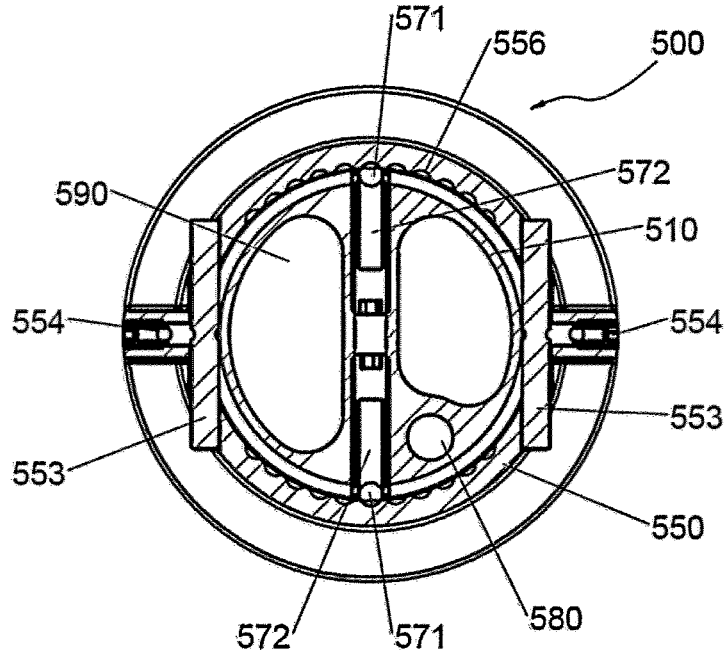
FIG. 22B is a cross-sectional end view of the wrist joint taken along line F-F of FIG. 22A.

The positioning member and connector may also be configured to be substantially hollow to maximise the length of a user's stump that can fit within the automated hand. This too helps the hand to look more anatomically correct, as can be seen in FIGS. 22B and 23.

In one form, the wrist joint may also comprise a watertight seal 560 between the positioning member and connector to prevent fluid from the hand passing into the arm member/sleeve.

Training Hand

It is necessary for a user of a prosthetic hand to create the necessary EMG (electromyography) signals to cause the hand to move to a desired position. Typically, it is necessary for a user of a prosthetic hand to practice using a practice hand for a significant period of time before the receiving the actual prosthetic hand to be used. In some forms, the practice hand may be a computer simulated hand. However, the actual prosthetic hand that will be used by the user may have different sensitivities to the practice hand. This means that the actual hand might not operate as expected, despite the user having practised with a practice hand for a long time. Therefore, the automated hand of the invention may comprise a control system and may be configured to provide training for the user as the hand is being used.

Figure 25:
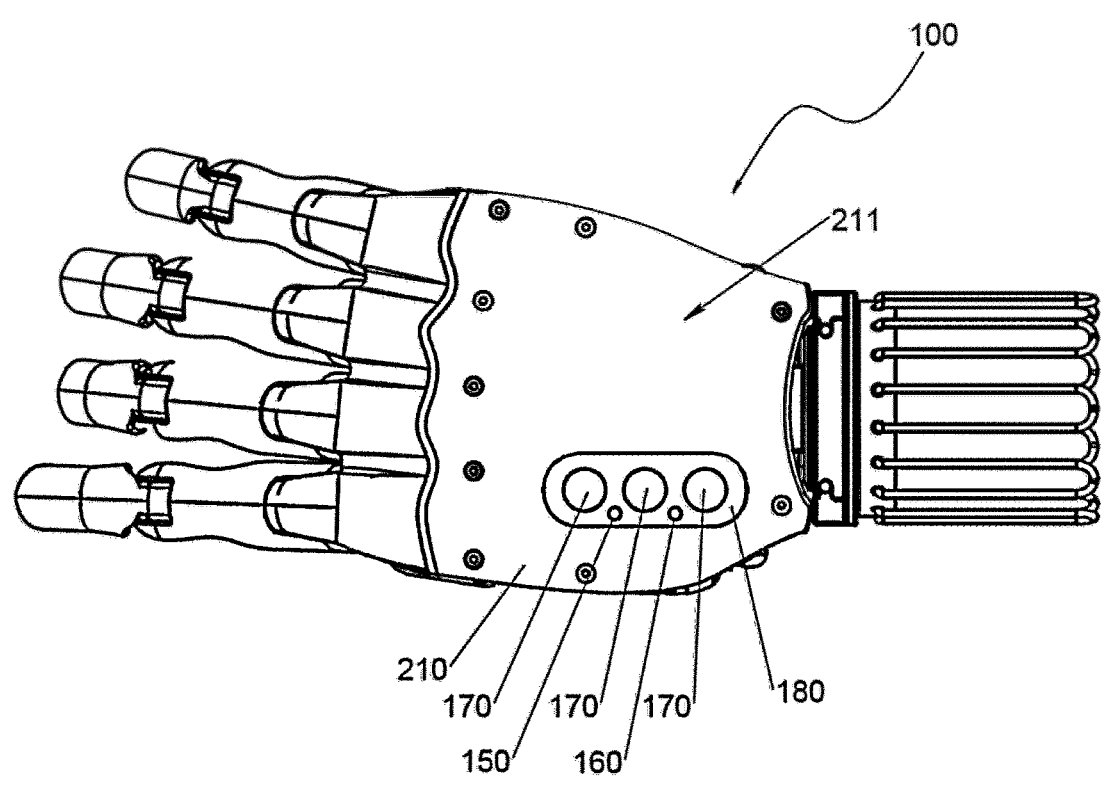
FIG. 25 is a plan view of the automated hand of FIG. 24 and comprising user interface for training purposes.
Figure 26:
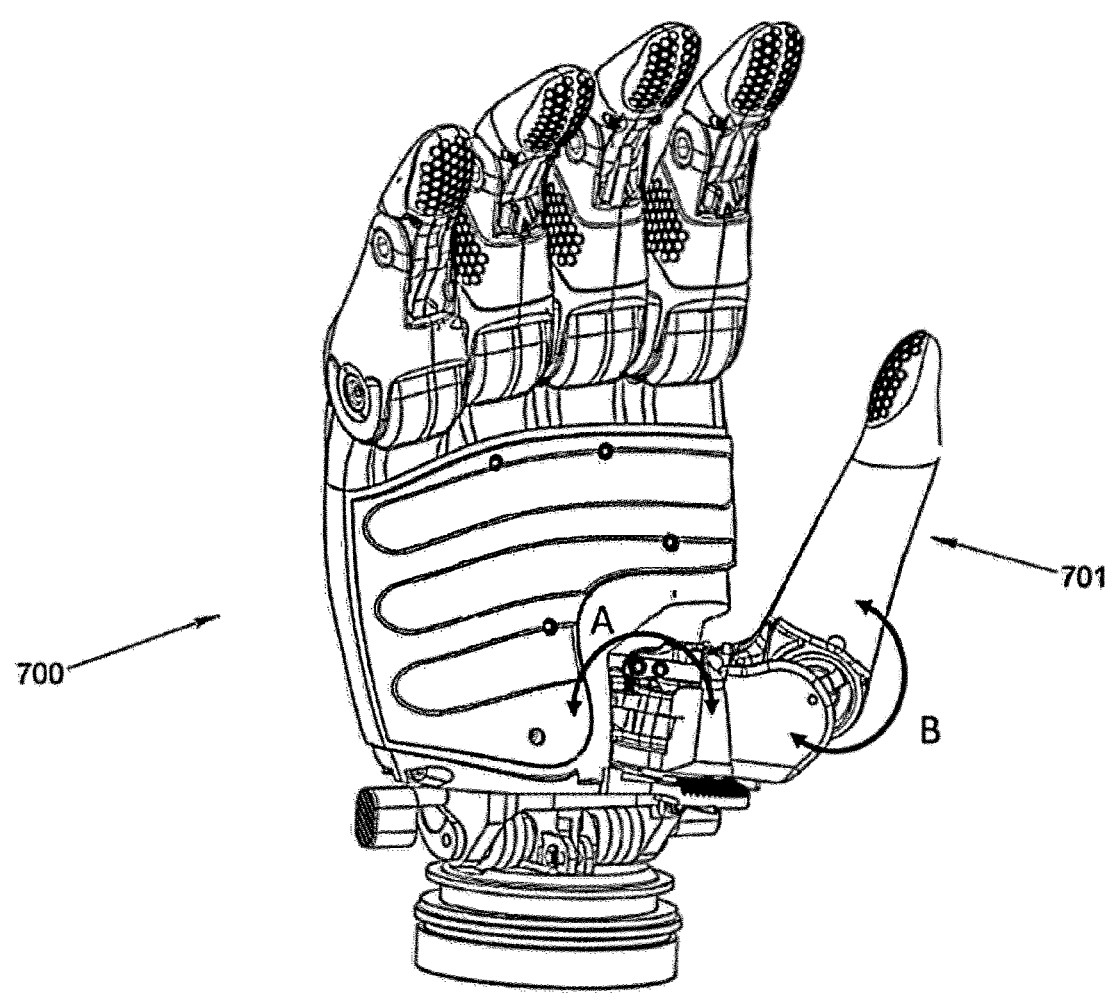
FIG. 26 is a side perspective view of an automated hand according to a second exemplary embodiment showing thumb rotation directions.
Figure 27:
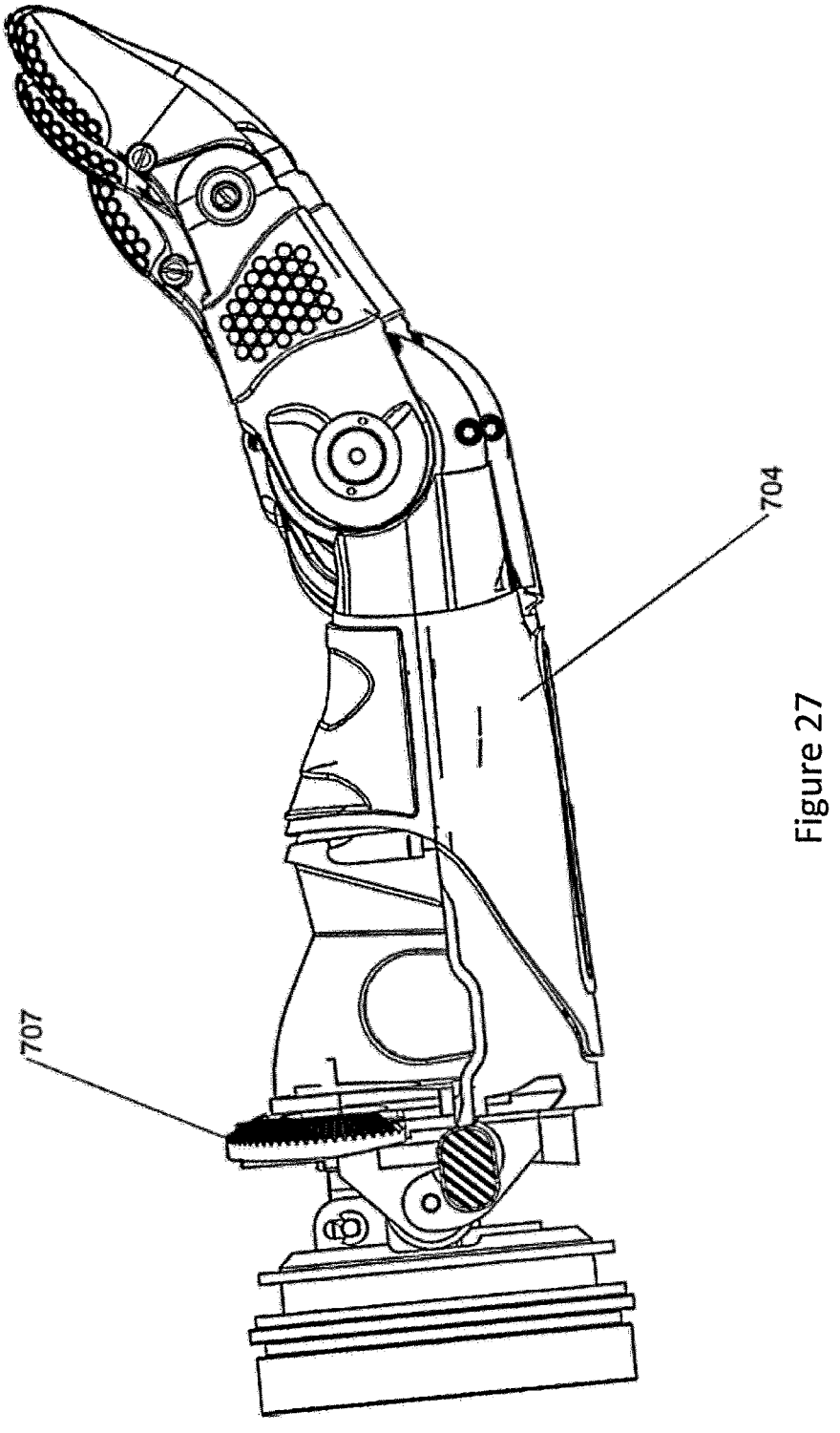
FIG. 27 is a side view of the automated hand of FIG. 26 with the thumb removed.
Figure 28:
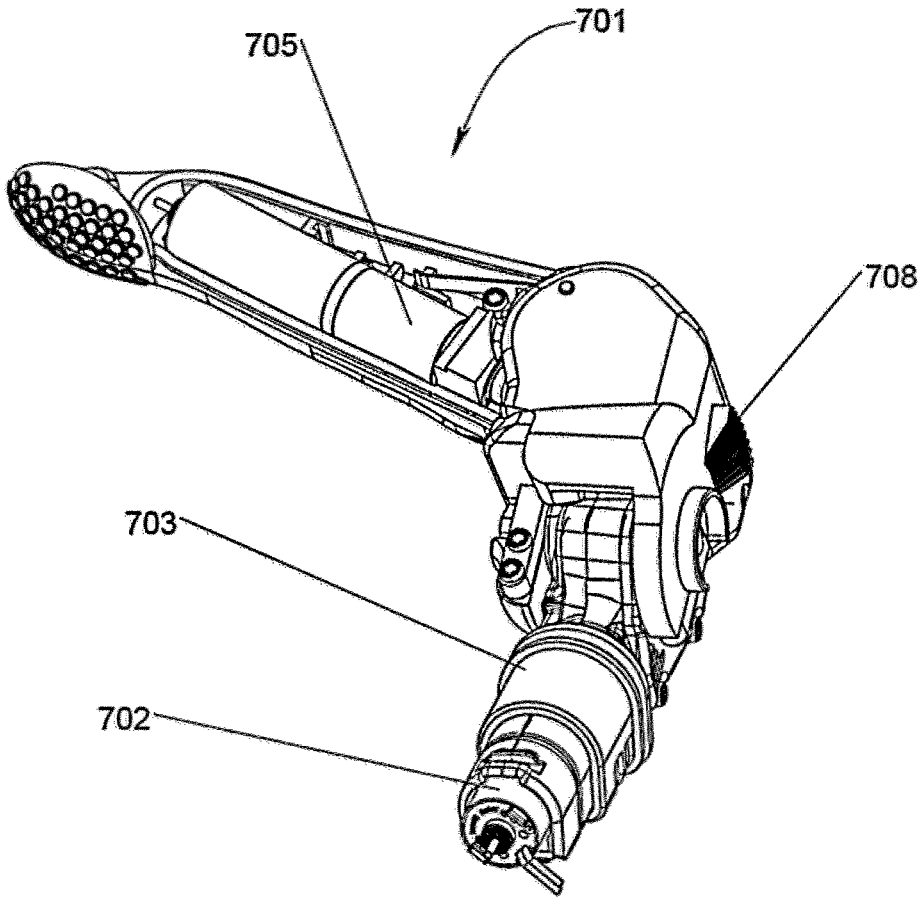
FIG. 28 is a perspective view of the thumb of the hand shown in FIG. 26.

In one form, as shown in FIG. 25, the hand 100 may comprise a control system connected to the drive motor(s) of the hand. The control system may be configured to receive one or more EMG signals from a user; one or more electronic signals from a user interface; or both. The control system may also be configured to cause the digits to assume a predetermined grip pattern depending on the signal(s) received.

The control system may be programmable to cause the hand to assume a predetermined grip pattern based on the signals received.

The hand may comprise a display in the form of one or more indicators that a signal has been received by the control system. In one form one or more indicators may be configured to indicate that an EMG signal has been received from the user. Additionally, or alternatively, one or more indicators may be configured to indicate the grip pattern of the hand 100. In yet another form, one or more indicators may be configured to indicate that a signal has been received from a user interface of the hand, such as via a Wi-Fi or Bluetooth connection. One indicator may also indicate an alarm mode.

The one or more indicators may comprise one or more visual indicators 150, audio indicators 160, or both.

In one form, the hand comprises at least one visual indicator and at least one audio indicator that a signal has been received by the control system.

Figure 54:
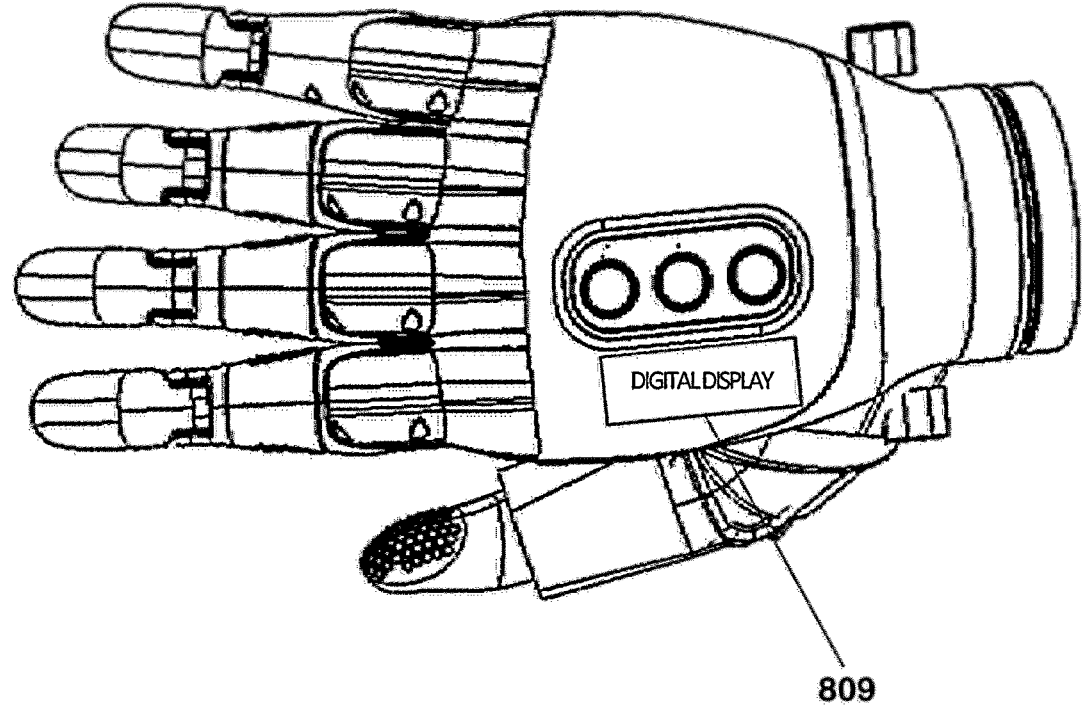
FIG. 54 is a plan view of an automated hand indicating an alphanumeric display.

The visual indicators 150 may be lights, such as LEDs, which may be of varying colours and/or may flash in various patterns depending on the position of the hand 100. Alternatively, the display may be an alphanumeric display 809 as shown in FIG. 54. An alphanumeric display enables each selected grip pattern to be displayed, specific fault conditions and detailed ranges for EMG signal strength etc.

The audio indicators 160 may be sounds created by the control system and emitted through speakers provided on the hand 100.

In one form, the hand 100 may comprise one or more visual indicators 150 and/or audio indicators located on any suitable part of the hand 100, such as the upper part 210 of the palm 200 or the wrist area 500. For example, one or more indicators 150, 160 may be located on the upper surface 211 of the upper part 210 of the palm 200. Preferably, three lights 150 are provided on the upper surface 211 of the palm.

The hand may comprise a user interface 180 through which a user may input instructions to the control system to cause the hand to assume a predetermined grip pattern. The user interface 180 may comprise one or more input members 170 through which a user may input data to cause the hand to assume a predetermined grip pattern. The one or more input members 170 may comprise one or more buttons, dials, or any other suitable system for inputting data. The user interface may be touch sensitive or mechanically operated or both.

In one form, the user interface 180 comprises one or more depressible buttons 170. In another form, the buttons may be touch sensitive. The buttons 170 may be located on any suitable part of the hand 100, such as the upper part 210, the wrist area 500, or the base of the lower part 220 of the hand. In one form, the buttons 170 are located on the upper surface 211 of the upper part 210 of the hand. In a preferred form, two or three buttons 170 are provided, as shown in FIG. 24. However, in other forms, four or more buttons may be used.

The user interface 180 may comprise a panel on the shell of the palm 200 of the hand. One or more input members 170, may be provided on the panel. Electronics connecting the input member(s) 170 to the control system may be located within the shell. Preferably, the panel 180 is sealed to avoid fluid reaching the electronics and control system. Alternatively, the electronics may be located within a sealed housing within the shell of the palm 200.

Optionally, the hand 100 comprises one or more input members 170 and one or more visual 150 and/or audio 160 indicators. The one or more input members, such as one or more buttons 170, may be located in the same area of the hand 100 as the visual indicator(s) 150 and/or audio indicator(s) 160. For example, one or more input members 170 and one or more indicators may be located on the user interface panel 180 on the hand, as described above. In one form, an LED light 150 may be located next to each input member or button 170. In one form, the hand may comprise one or more input members 170 comprising one or more visual indicators 150. For example, an LED light may be located on each button. In another example, multiple LED lights may be provided on a dial.

In one form, the number of visual and/or audio indicators may equal the number of input members, such as buttons. In other forms, the number of input members may exceed or be less than the number of visual indicators and/or audio indicators.

The control system of the hand may be configured so that signals received from one or more input members 170, EMG signals, or both may be used to cause the hand 100 to change from one grip pattern to another. For example, a user may depress one or more buttons 170 in a particular pattern to select a grip pattern, such as a grip pattern where the thumb 320 is in an opposition position and the fingers 310 and thumb 320 of the hand are curled.

A particular indicator or combination of indicators may be used to indicate that the signal received by the control system is an EMG signal or an input signal from one of the input members. For example, a red light may indicate that an EMG signal has been received and a green light may indicate that an input signal has been received from the user interface. In one form the brightness of a single LED indicator may vary in proportion to the strength to the received of received EMG signals to provide an indication of the strength of EMG signals received to the user.

The control system of the hand may be configured to store a certain number of grip patterns, such as the twenty most common grip patterns, that may be obtained by inputting data to the control system through the input member(s) 170 of the hand, EMG signals, or both. In one for an indicator is illuminated when the first grip pattern is selected so that a user may push an input button a number of times from this state to select a desired grip pattern.

The input member(s) 170 may be particularly useful when a user is unable to create the necessary EMG signal needed to achieve a particular grip pattern.

In one form, the control system may be programmed to recognise only some EMG signals. In this form, other grip patterns may be controlled by the input member(s) 170 of the user interface 180.

Therefore, the hand 100 of the invention may be configured to be used as a training tool to help train the user to become accustomed to the hand, especially the various positions of the hand.

Fluid Compatible Hand

In one form, the hand of the invention may be configured to operate when wet. For example, the hand may be configured to operate when submerged in water, without needing to use a glove or waterproof covering over the hand.

It is very difficult for an electrically powered automated hand with many moving mechanical parts to be made fluid compatible. It is even more difficult where the part of the hand have been designed to be small enough to make the hand appear to be substantially anatomically correct. To provide a water compatible hand, the construction of a typical automated hand has been re-engineered by the inventor from the ground up. As a result, the fluid compatible automated hand of the invention is configured to operate when dry and when wet. The hand is not waterproof because the interior of the hand may become wet when the hand is submerged in fluid, such as water. Instead, the hand is configured to be fluid compatible, meaning that the hand will operate even when submerged in fluid.

The hand is configured to be fluid or water compatible in several ways. For example, the drive motors of the hand may be individually housed within sealed housings. Electrical connections may be provided using any suitable fluid compatible connection, such as by using remote connection or by using ribbon cables for example. In one form, ribbon connectors are used to traverse the wrist joint between the palm and arm member to connect electronics in the palm and/or digits with electronics in the arm member, such as a sleeve. The ribbon connectors are configured to be waterproof and may also be configured to withstand the moving nature of the hand as the palm curls, flexes, and/or rotates about the wrist joint.

The controllers and electronics may be placed within one or more sealed housings, such as an electronics housing within the palm of the hand.

The palm and wrist joint may also comprise one or more watertight seals. For example, a seal may be located between the positioning member and connector of the wrist joint to prevent fluid from the automated hand entering the arm member/sleeve. In particular, the wrist joint may comprise a positioning member attached to a connector, as described above, and an arm member comprising a sleeve may also be attached to the connector. A rubberised seal is located between the attached positioning member and connector. The connector, positioning member and seal together form a sealed end to the sleeve so that fluid is unable to pass into the sleeve and damage electronic components within the sleeve. The user's stump, which will be positioned within the sleeve during use, will also be kept dry.

Where the hand is attached to an arm member using a positioning system of the invention and/or using a disconnect system, the hand is able to rotate relative to the arm member. This rotational capability is particularly beneficial when coupled with a fluid compatible hand.

The hand may be configured to be drainable. For example, the hand may comprise one or more drainage ports, such as apertures in the palm and/or digits, through which fluid may drain after the hand has been submerged in fluid. Alternatively, the fluid may drain through one or more openings that are provided between adjoining parts of the hand, such as the openings that form around the knuckle and digit joints, for example.

The automated hand of the invention is therefore configured to be floodable and drainable so that a user could use the hand to do the dishes, for example.

To help provide additional grip, a grip assisting surface, such as a tacky, textured, or high friction surface, may be provided on the contact surface of the palm of the hand and contact surfaces of the digits. The contact surface of the digits are areas of the digits that are most likely to contact an object being gripped. For example, the fingertip area may be a contact surface. In one form, the grip assisting surface may be a rubberised surface comprising rubber, silicon, or an elastomer for example.

Conventional automated hands require a glove to be used to help with grip, water resistance, and protection against general wear and tear. Known automated hands are not able to operate when submerged in fluid. Where a glove is used, the drive motors of the hand strain to move the digits against the constrictive nature of the glove. In other words, the motors need to work harder to move the digits than if no glove is used. These disadvantages may be avoided by the fluid compatible hand of the invention, because it is unnecessary for a glove to be used with the hand. Greater gain can therefore be obtained from the drive motors and less power may be consumed to move the digits of the hand from one position to another. In addition, without the constriction of a glove, the digits of the hand may move faster. The automated hand of the invention also has less risk of water damage or damage from other fluids.

Because the hand of the invention may be worn without a glove, it is possible for the hand to be used as a training hand, as described above, where one or more LED lights may be located on the hand and visible to the user.

The fluid compatible hand of the invention is also configured to be readily maintained without adversely affecting the fluid compatible nature of the hand.

Second Exemplary Embodiment

FIGS. 26 to 66 show an automated hand according to a second embodiment employing a different thumb rotation locking mechanism, wrist locking mechanism, overload knuckle clutch, removable grip plates and related features.

Those parts that are equivalent to corresponding parts in the first embodiment have been given the same numbering and the above description should be referenced in relation to those parts. The metacarpal brace has the same properties described in relation to the previous exemplary embodiment.

The actuator described below includes a connector housing the actuator although a connector need not necessarily house an actuator in alternate embodiments.

Thumb Rotation Locking

Referring now to FIGS. 26 to 30 an alternate thumb design is shown. Thumb 701 has an actuator 702 provided at its proximal end (including the actuator housing) which is also its point of attachment to palm 704. A resilient mount 703 is mounted to palm 704 and includes a cavity dimensioned to receive the actuator 702. By mounting the thumb 701 to the palm via a resilient mount 703 the thumb can absorb impact forces by elastic deformation of resilient mount 703. The resilient mount 703 preferably permits relative angular displacement of the actuator 702 with respect to the palm 704 of at least 2 degrees, and preferably at least 5 degrees. The resilient mount 703 may have material properties as set out for the metacarpal brace described above in relation to the first exemplary embodiment.

The relative movement of the thumb 701 with respect to the palm 704 may also be utilised in a thumb locking mechanism. Actuator 702 rotates thumb 701 as indicated by arrow A about an axis generally in the direction of extension of the hand. In this embodiment actuator 702 allows thumb rotation for positioning purposes when a user applies rotational force (i.e. it does not have a gear drive such as a worm drive preventing reverse drive). This enables a user to rotate the thumb into a desired position. This also allows the thumb to absorb forces caused by an accidental impact to the thumb. A second actuator 705 controls closure and extension of the thumb as indicated by arrow B.

Figure 29:
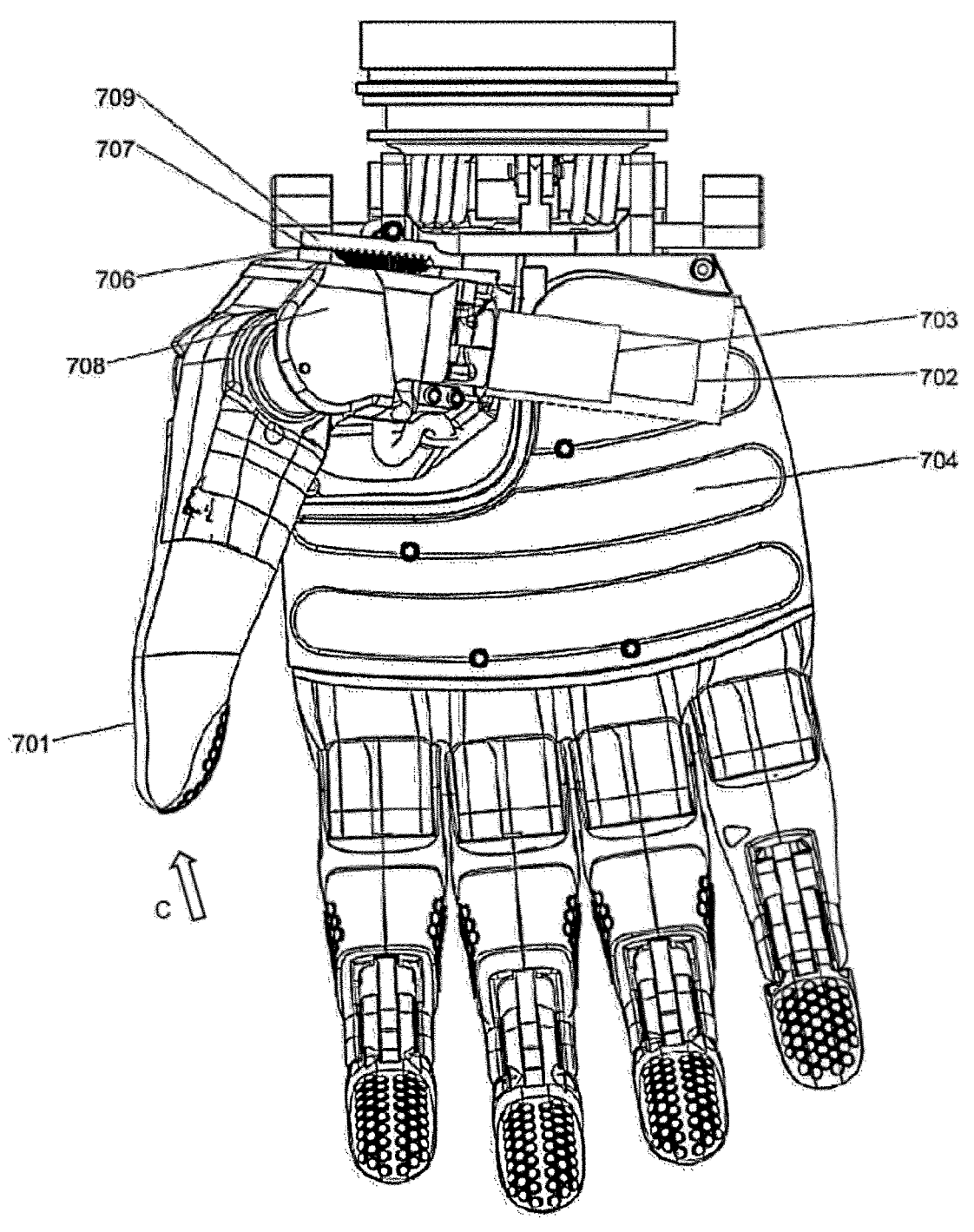
FIG. 29 is a bottom view of the hand shown in FIG. 26 with a thumb rotation lock engaged.
Figure 30:
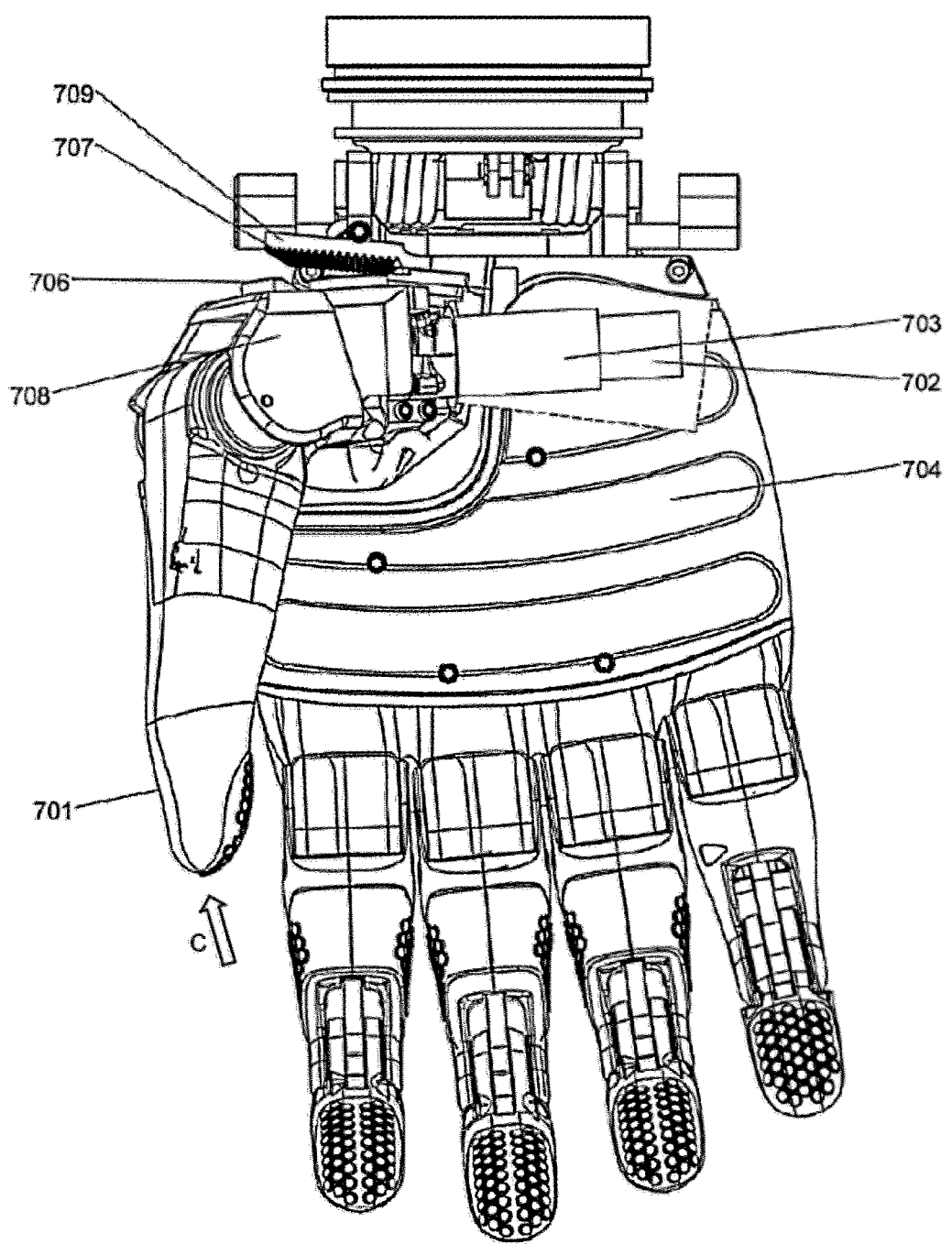
FIG. 30 is a bottom view of the hand shown in FIG. 26 with the thumb rotation lock disengaged.
Figure 31:
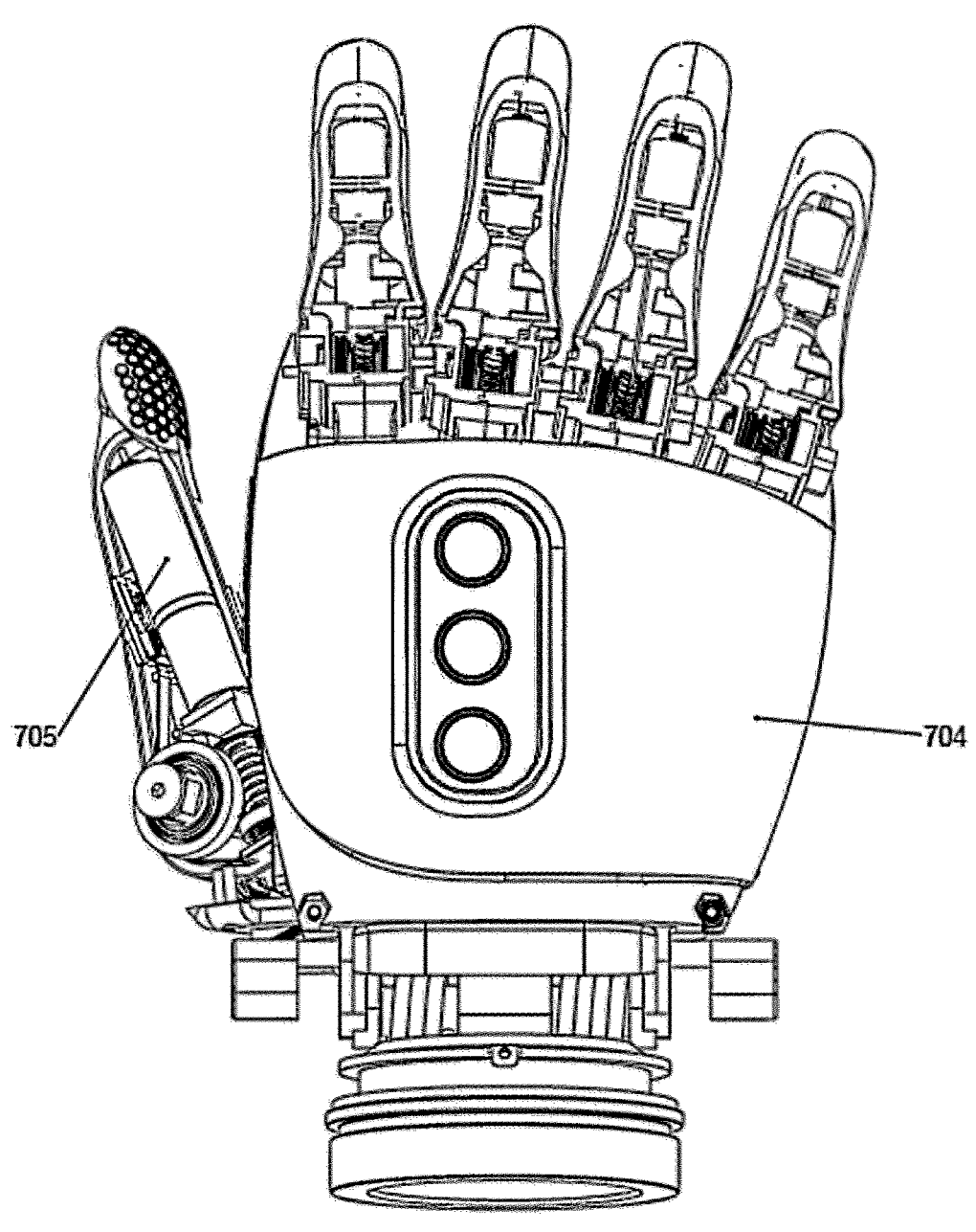
FIG. 31 is a top view of an automated hand shown in FIG. 26 with cut always showing the actuators housed in the fingers and thumb.

Due to the ability of the thumb to be rotated by applied force it is desirable to lock the thumb in a fixed rotational position during movements such as gripping an item (to prevent release due to rotation of the thumb). FIGS. 29 and 30 illustrate the operation of the thumb rotation lock. FIG. 30 shows the positions of the elements when no force is applied in direction C. When the thumb is closed against an object or another digit a force as indicated by arrow C causes actuator 702 to apply force to resilient mount 703 causing rotation of the thumb and actuator 702 as shown in FIG. 29 (the distal end of actuator 702 is seen to have moved towards the wrist). This forces block 708 against palm block 709. A first engagement surface 706 may be provided on block 708 and a second engagement surface 707 may be provided on palm block 709. When the two engagement surfaces are brought into contact this may prevent further rotation (i.e. rotation in direction A) so as to assist in retaining a grip without thumb rotation. This is particularly important where the actuator may move when force is applied (unlike a worm drive which may prevent backward rotation). Allowing rotation of the thumb may assist in thumb positioning and allow force to be dissipated without damaging the thumb. The engagement surfaces 706 and 707 may both have profiles that interengage, such as a corrugated profile such as a gear surface. Alternatively, one surface may have a high coefficient of friction, such as a brake pad material, and the other may or may not have a surface profile. A surface having a high coefficient of friction may also be contoured. In this example surface 707 has a gear profile and is formed of a resilient material to provide good grip.

This design allows a user to rotate the thumb into a desired position but still allows reliable gripping by virtue of the thumb rotation locking mechanism described above. It also absorbs forces due to accidental impacts to the thumb to avoid damage to the thumb or hand due to accidental impacts.

Figure 32:
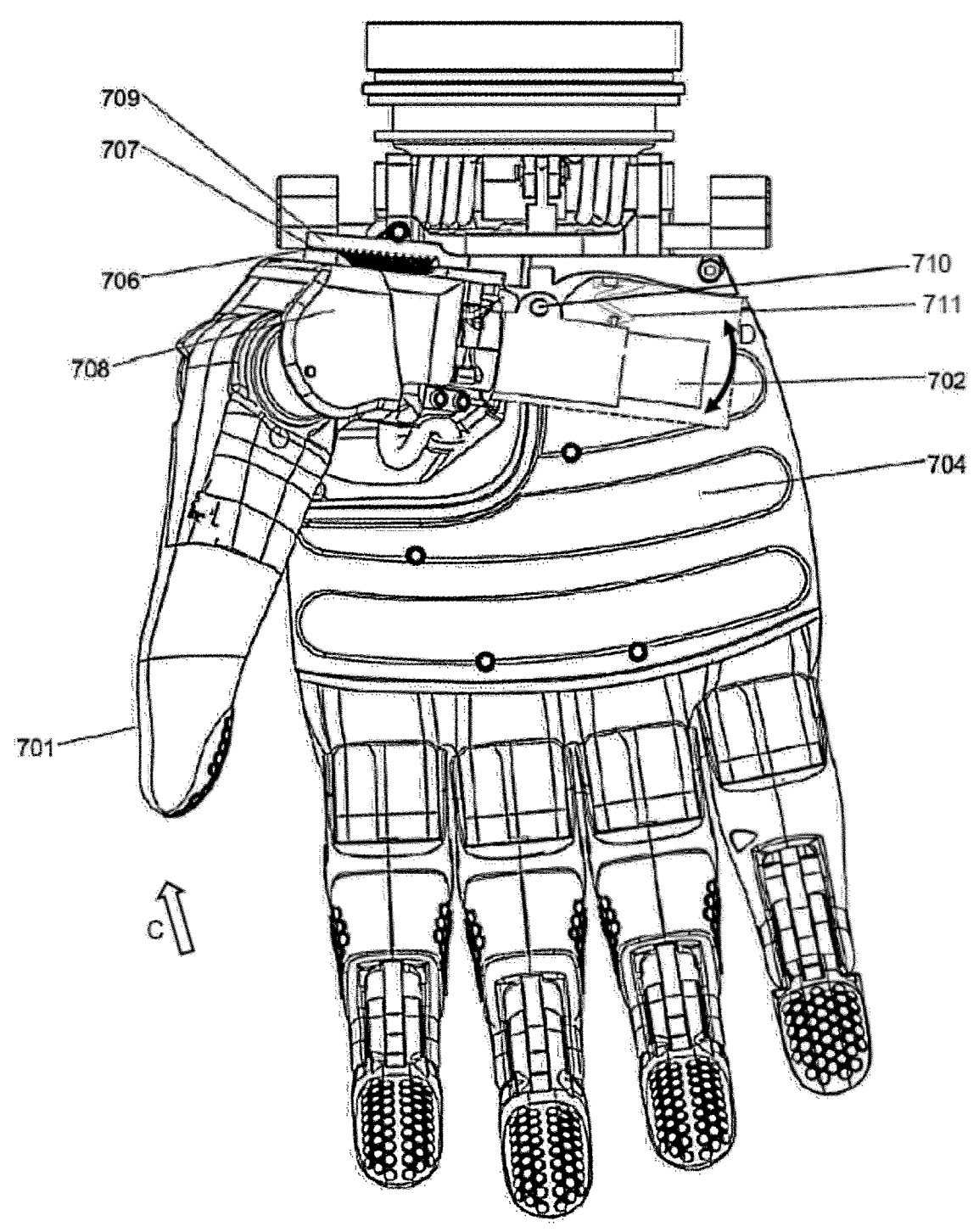
FIG. 32 is a bottom view of an alternative embodiment of the thumb rotation lock in an engaged position.

A variant of this design is shown in FIG. 32 in which the thumb rotation actuator 702 is pivotally mounted to palm 704 and biased towards a neutral position by spring 711. When force is applied in direction C during a gripping movement actuator 702 rotates about pivot point 710 as indicated by double arrow D so that engagement surfaces 706 and 707 come into contact and restrict further rotation.

Clutch

Figure 33:
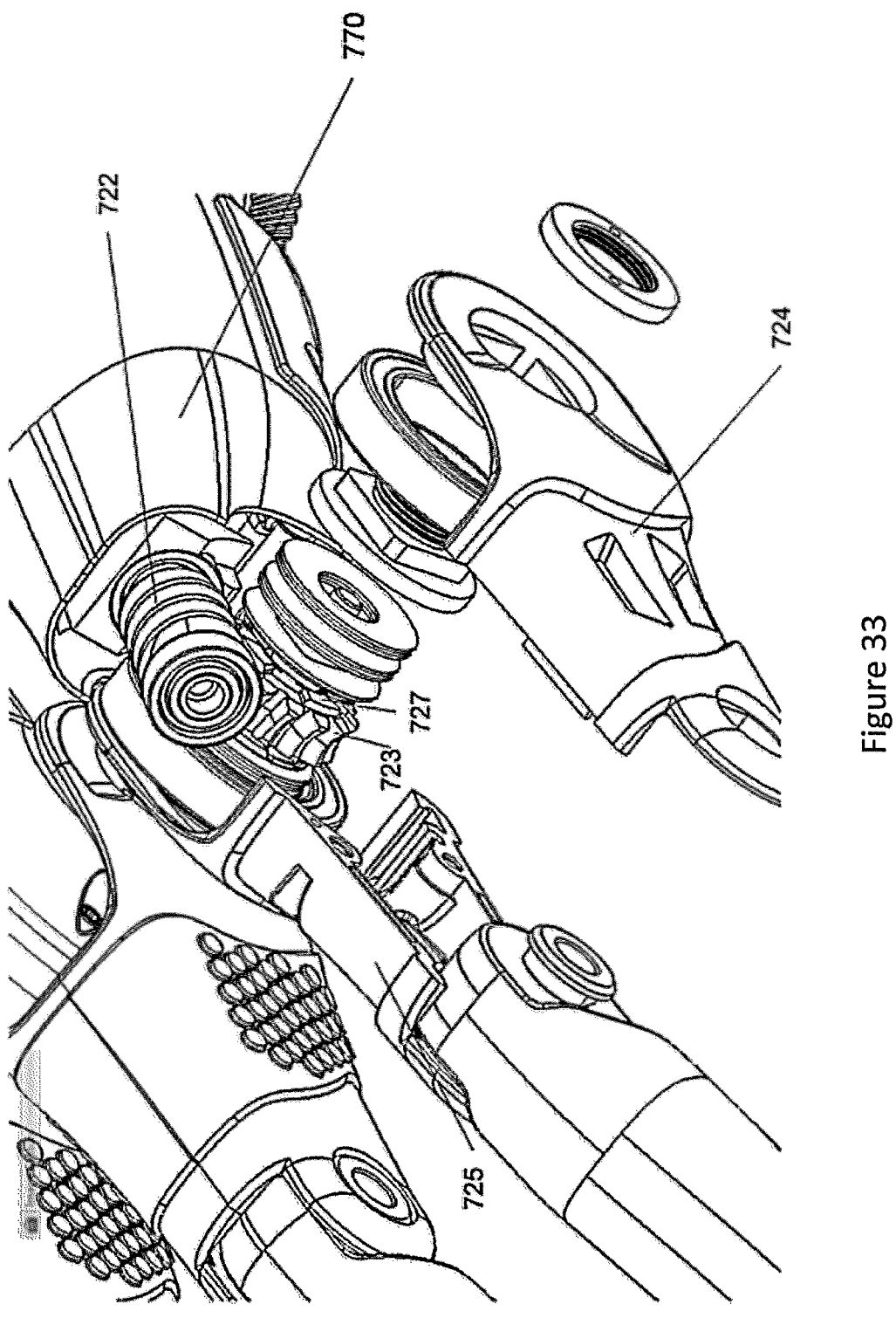
FIG. 33 is a perspective view and partial explosion of a further knuckle clutch embodiment for an automated hand.

Referring to FIGS. 33 to 41 an overload protection clutch 720 integrated into a knuckle joint will be described. Referring to FIG. 33 an actuator 726 mounted in metacarpal brace 721 located with the palm drives a worm gear 722 which in turn drives gear wheel 723. Gear wheel 723 drives left and right digit elements 724 and 725 via the overload clutch arrangement as will now be described.

Figure 34:
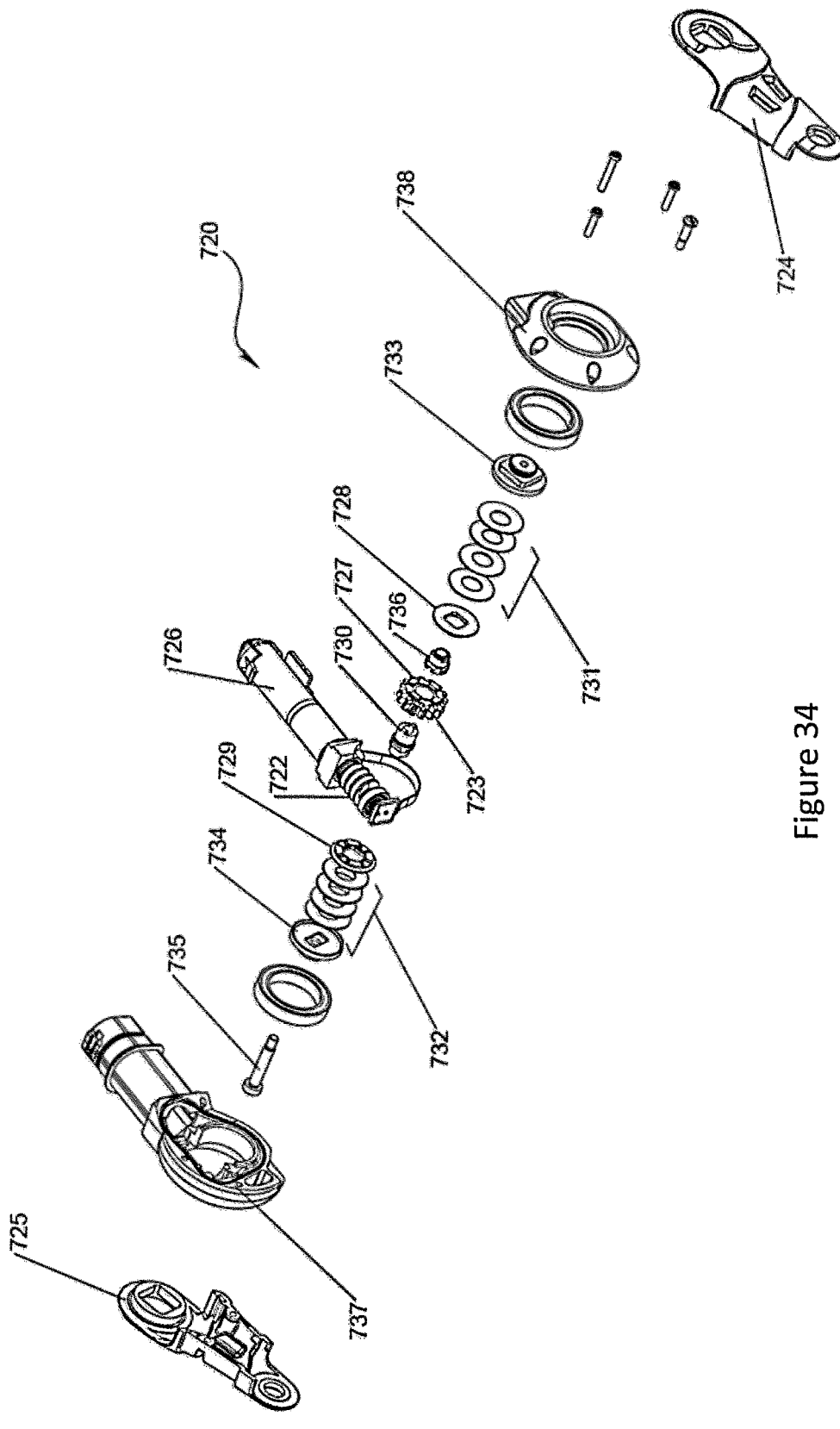
FIG. 34 is an exploded view of the knuckle clutch shown in FIG. 33.
Figure 35:
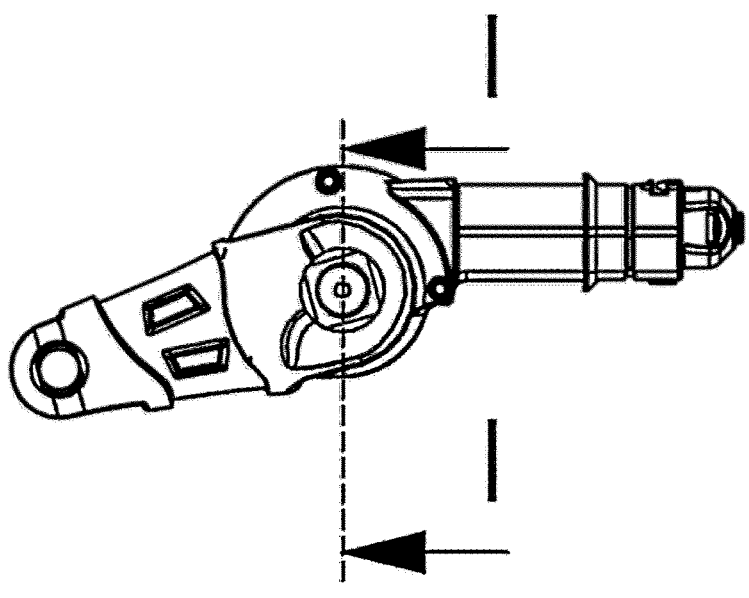
FIG. 35 is a side elevation of the clutch shown in FIG. 33.
Figure 36:
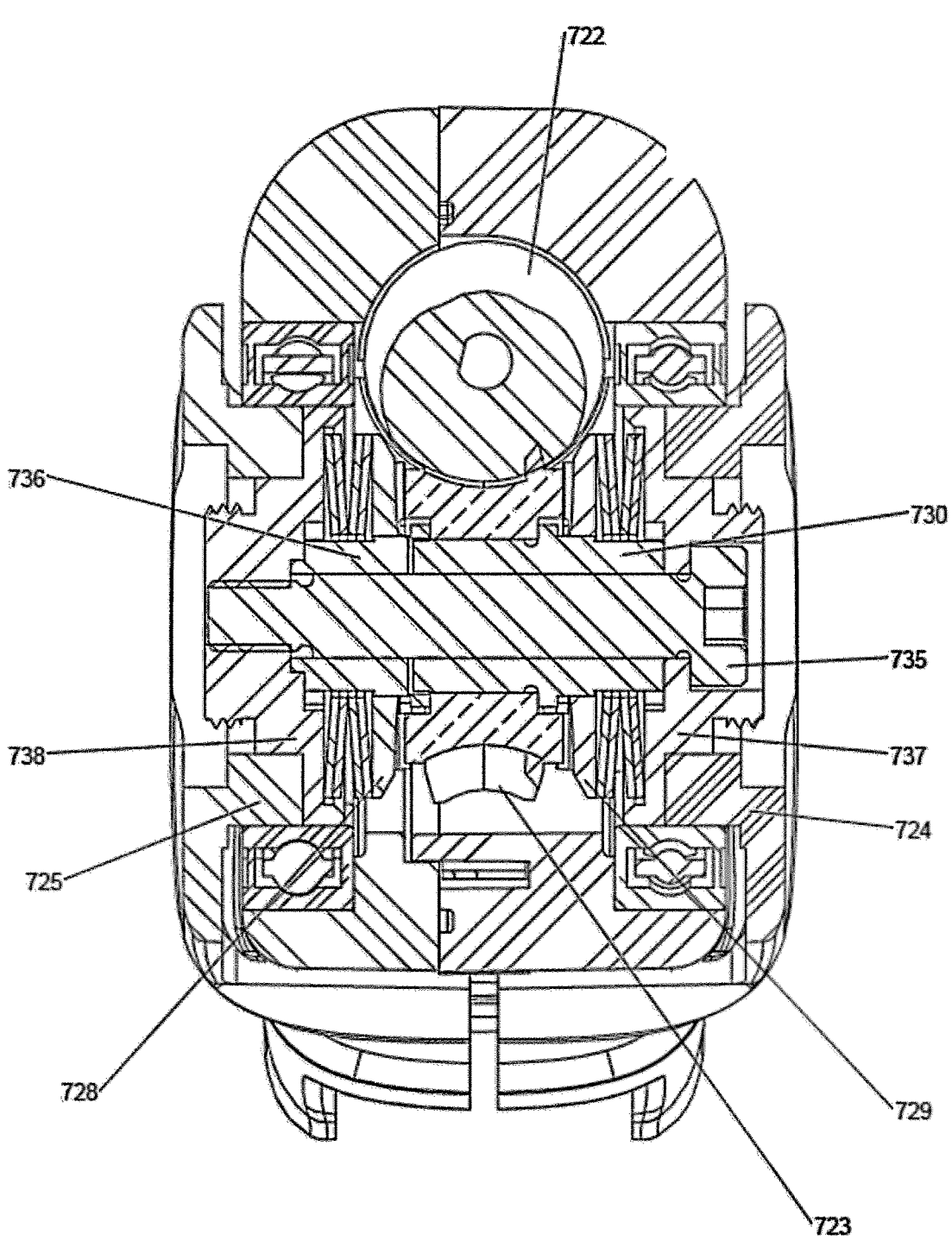
FIG. 36 is a sectional view along line I-I FIG. 35.

Referring to FIG. 34 an exploded view of the overload clutch 720 is shown. Gear wheel 723 rotates freely about axle 730 and has a series of ramps 727 provided on either side, one of which is indicated. The ramps 727 engage with complimentary ramps formed in clutch plates 728 and 729 (see ramps 739 in FIGS. 39 to 41). The clutch plates 728 and 729 are biased towards gear wheel 723 by disc springs 731 and 732. The entire "assembly" of output plates 733 and 734, disc springs 731 and 732, clutch plates 729 and 729 and axles 730 and 736 are secured together by bolt 735 to form one integral drive unit. The knuckle joint is enclosed within housing elements 737 and 738.

In normal operation actuator 726 rotates worm wheel 722, which in turn rotates gear wheel 723 (which freely rotates about axle 730). The ramps 727 of gear wheel 723 engage complementary ramps of clutch plates 728 and 729 which drives the "assembly" to rotate the left and right digit elements 724 and 725. Should an impact force be applied to a digit, or rotation of the digit be restrained at a certain level of force, the ramps 739 of the clutch plates 728 and 729 will be driven up against the ramps 727 of the gear wheel so as to apply an outward force on the clutch plates 728 and 729 compressing disc springs 731 and 732 until the ramp surfaces no longer engage, allowing rotation of clutch plates 728 and 729 with respect to gear wheel 723 to relieve the overload force applied.

Figure 38:
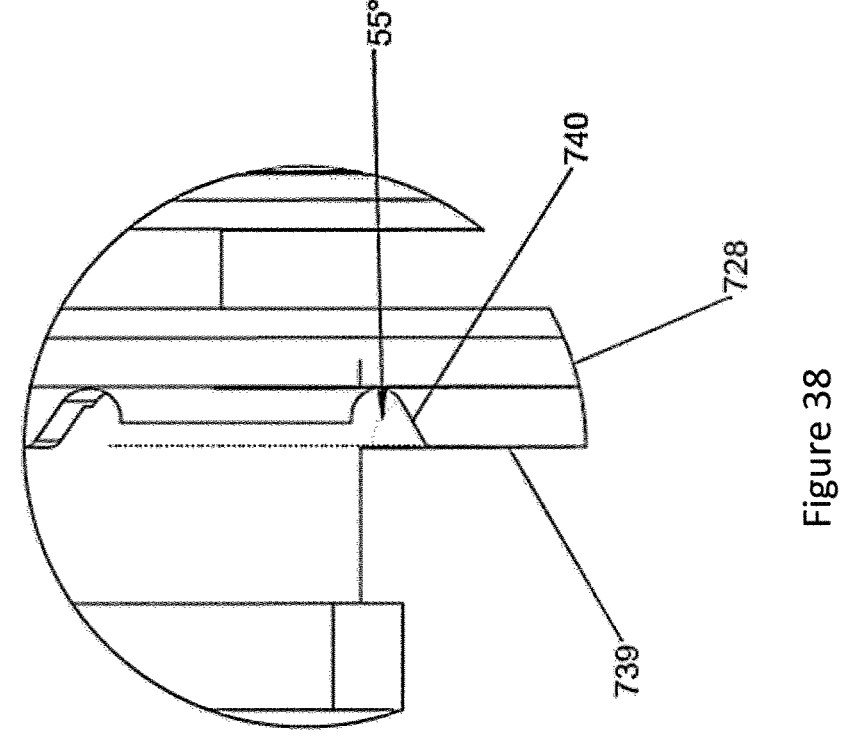
FIG. 38 is a magnified view of area J in FIG. 37 showing the clutch plate.
Figure 37:
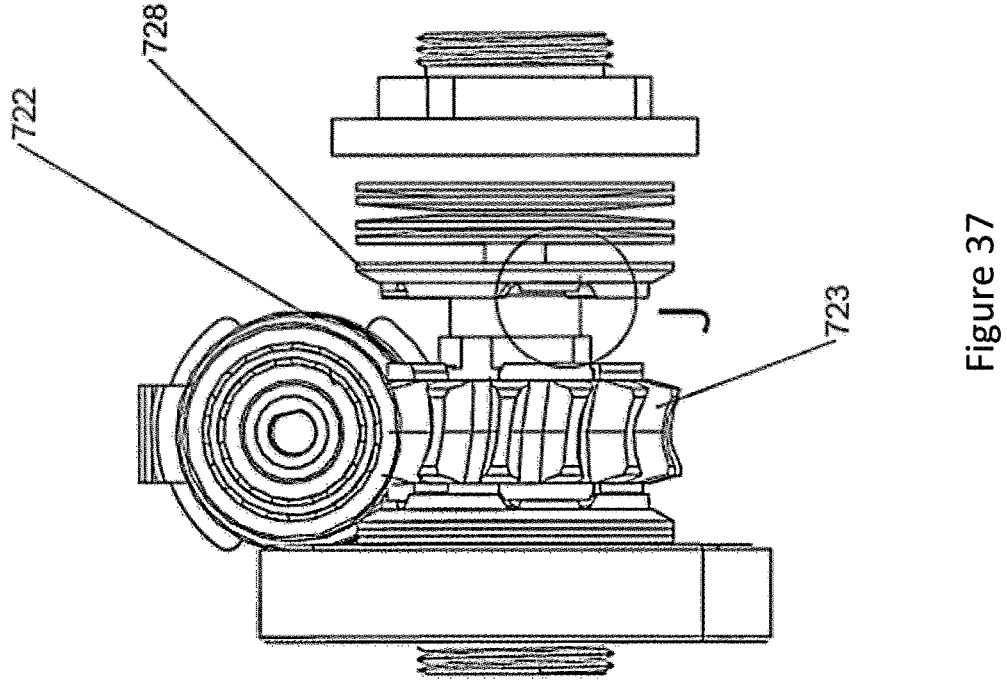
FIG. 37 is an end view of the clutch shown in FIG. 33.

Referring to FIGS. 38 to 41 the clutch plate 728 is shown in more detail (clutch plate 729 is identical). In this example four ramp sections 739 are shown but any number between 3 to 8 ramp sections may be appropriate. As shown in FIG. 38 ramp face 740 is disposed at an angle of 55° to the flat surface of ramp 739. Whilst the ramp surfaces 727 are shown to be integrally formed on gear wheel 723 it will be appreciated that clutch plates could be secured to either side of gear wheel 723 instead.

Figure 42:
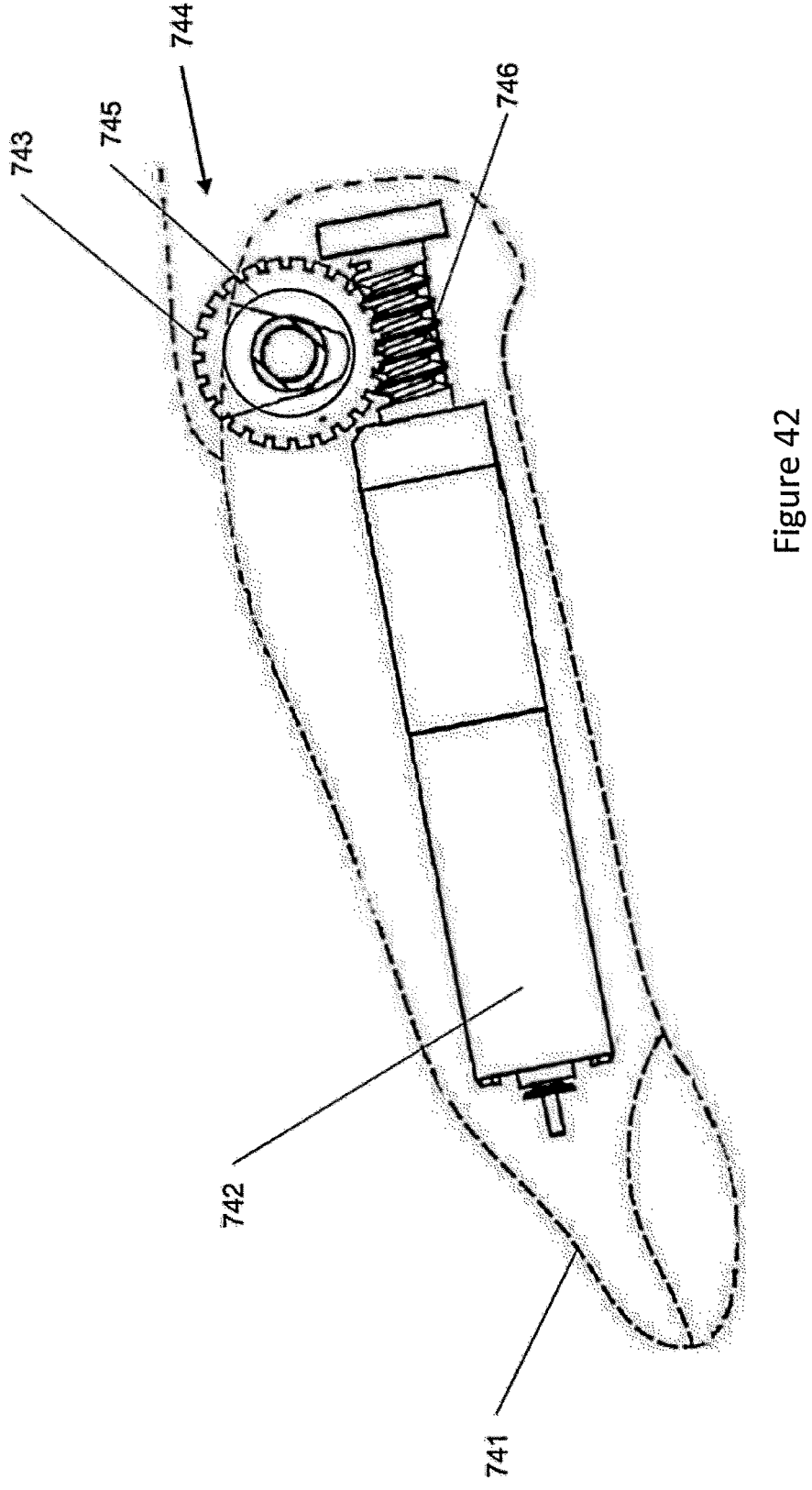
FIG. 42 is a side elevation of a clutch according to a further embodiment having a motor drive in the finger.
Figure 43:
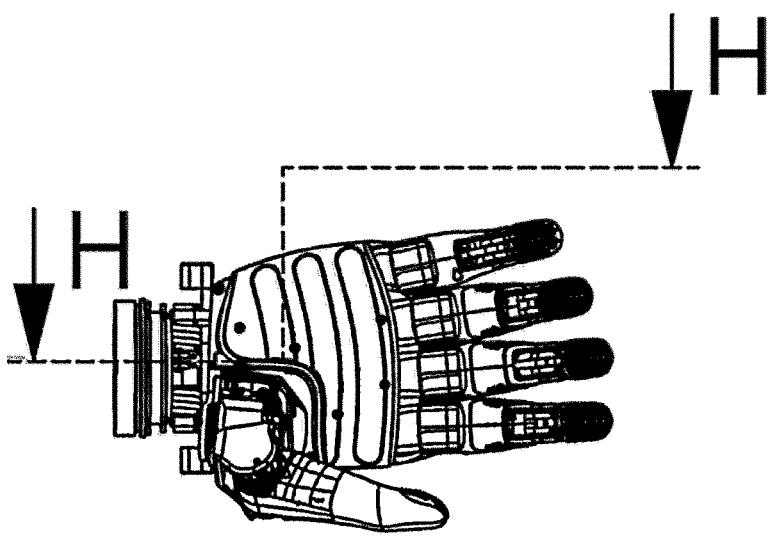
FIG. 43 is a bottom view of a wrist mechanism according to a further embodiment in a neutral position.

FIG. 42 shows an alternate embodiment in which a gear wheel 743 is mounted to palm 744 via a clutch 745 of the type described above. A motor 742 within digit 741 drives worm gear 746 to cause the finger to rotate about the palm. Should an excessive rotational force be applied to digit 741 then clutch 745 allows rotation of the gear wheel 743 with respect to the palm so as to allow rotation of the digit 741 with respect to the palm to relieve the overload force.

Integration of the clutch on the gear face provides a compact and light weight solution with reduced forces on ramp surfaces resulting in low wear of the clutch plates. The clutch releases consistently under an overload release force and provides bidirectional protection

Wrist

Figure 44:
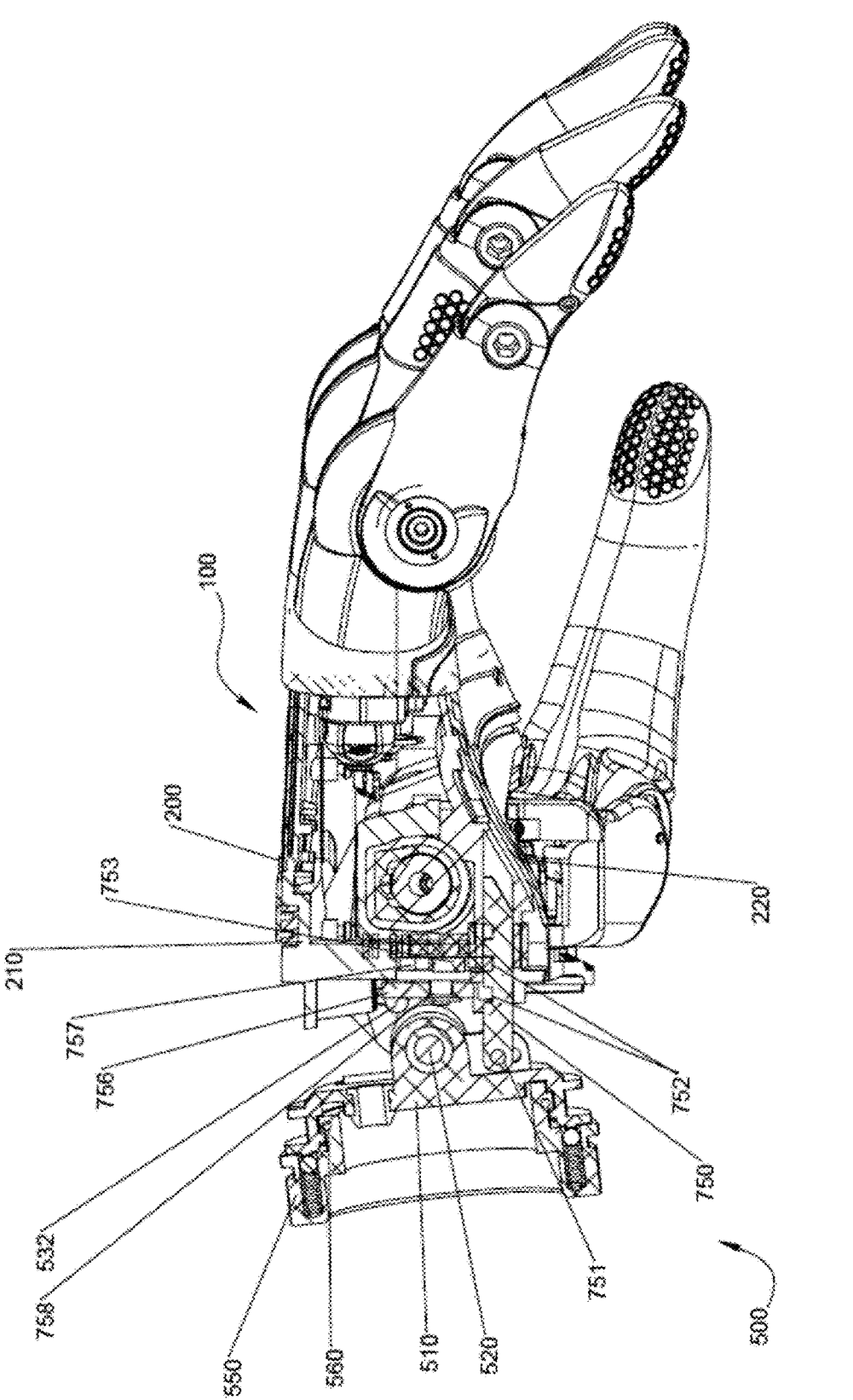
FIG. 44 is a sectional view along line H-H of FIG. 43.
Figure 45:
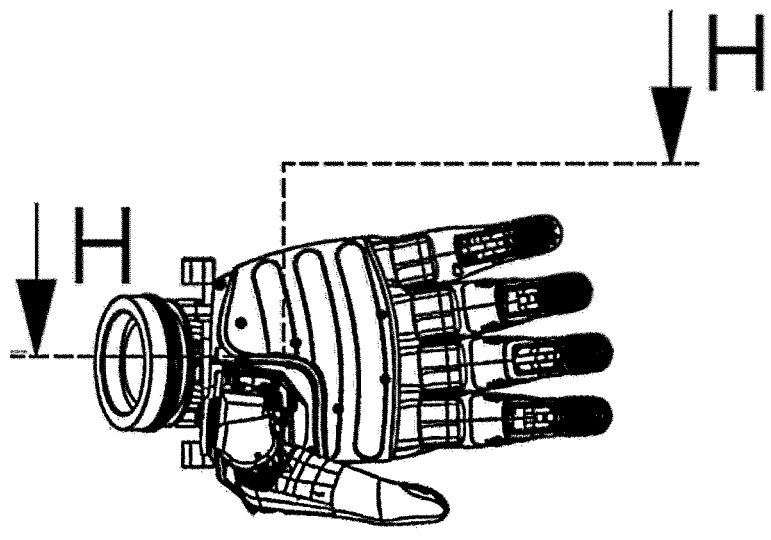
FIG. 45 is a bottom view of the hand shown in FIG. 43 in the flexion position.
Figure 46:
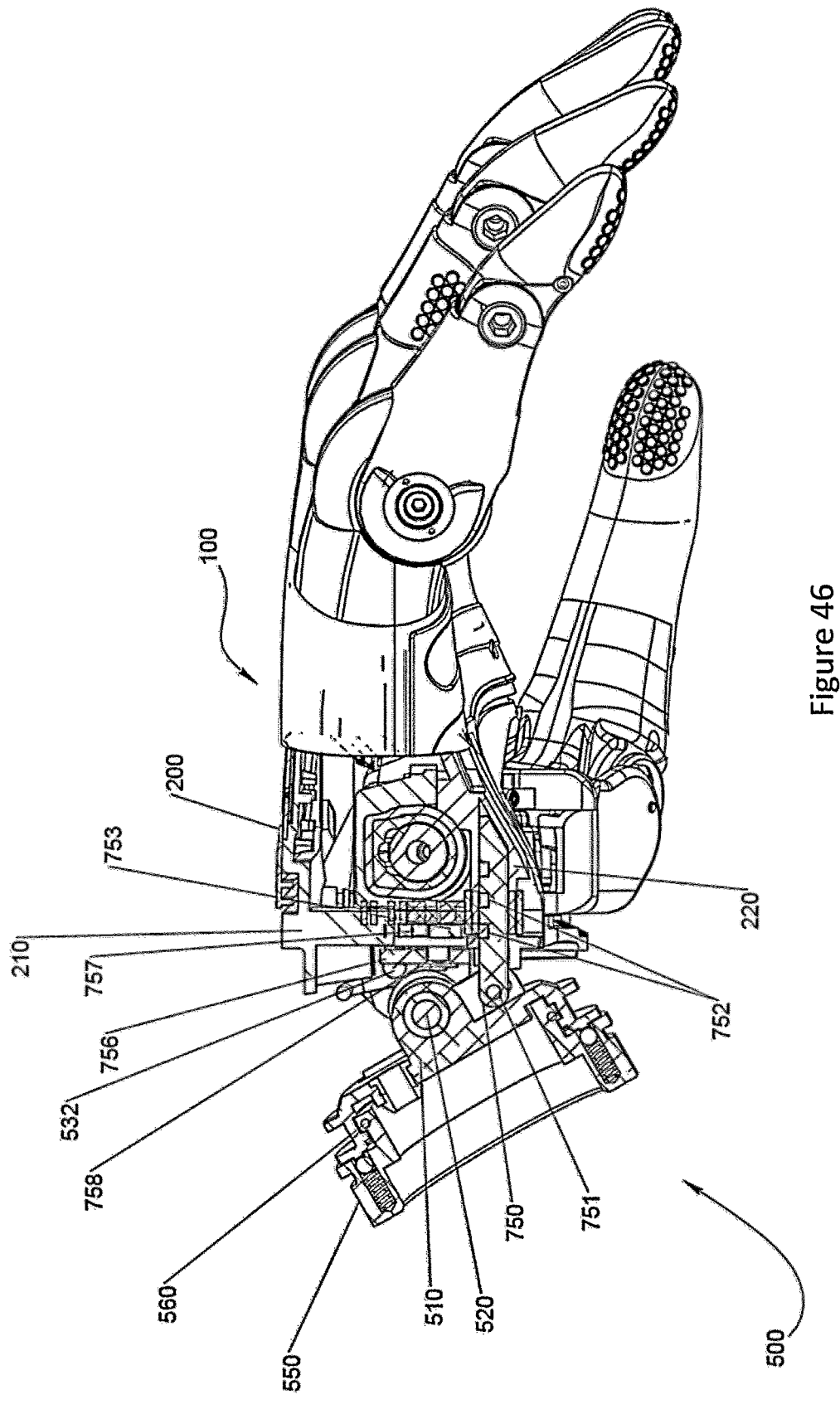
FIG. 46 is a sectional view along line H-H of FIG. 45.
Figure 47:
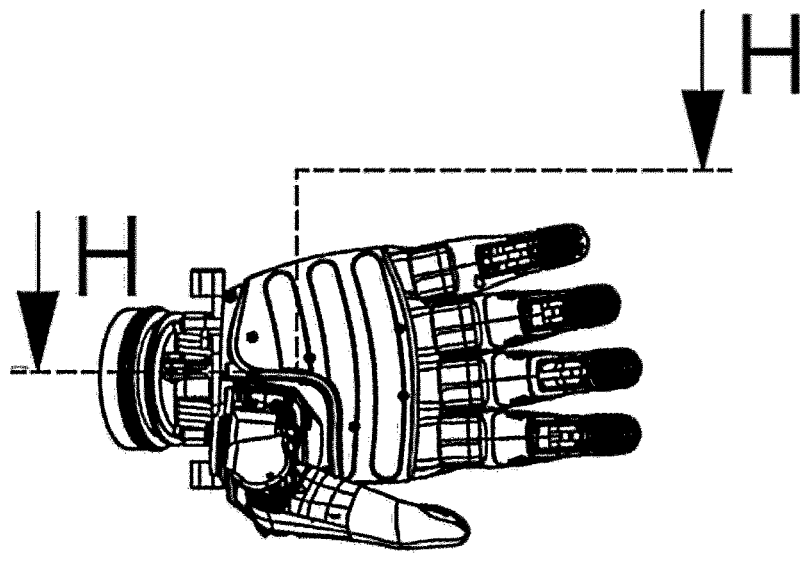
FIG. 47 is a bottom view of the hand shown in FIG. 43 in the extension position.
Figure 48:
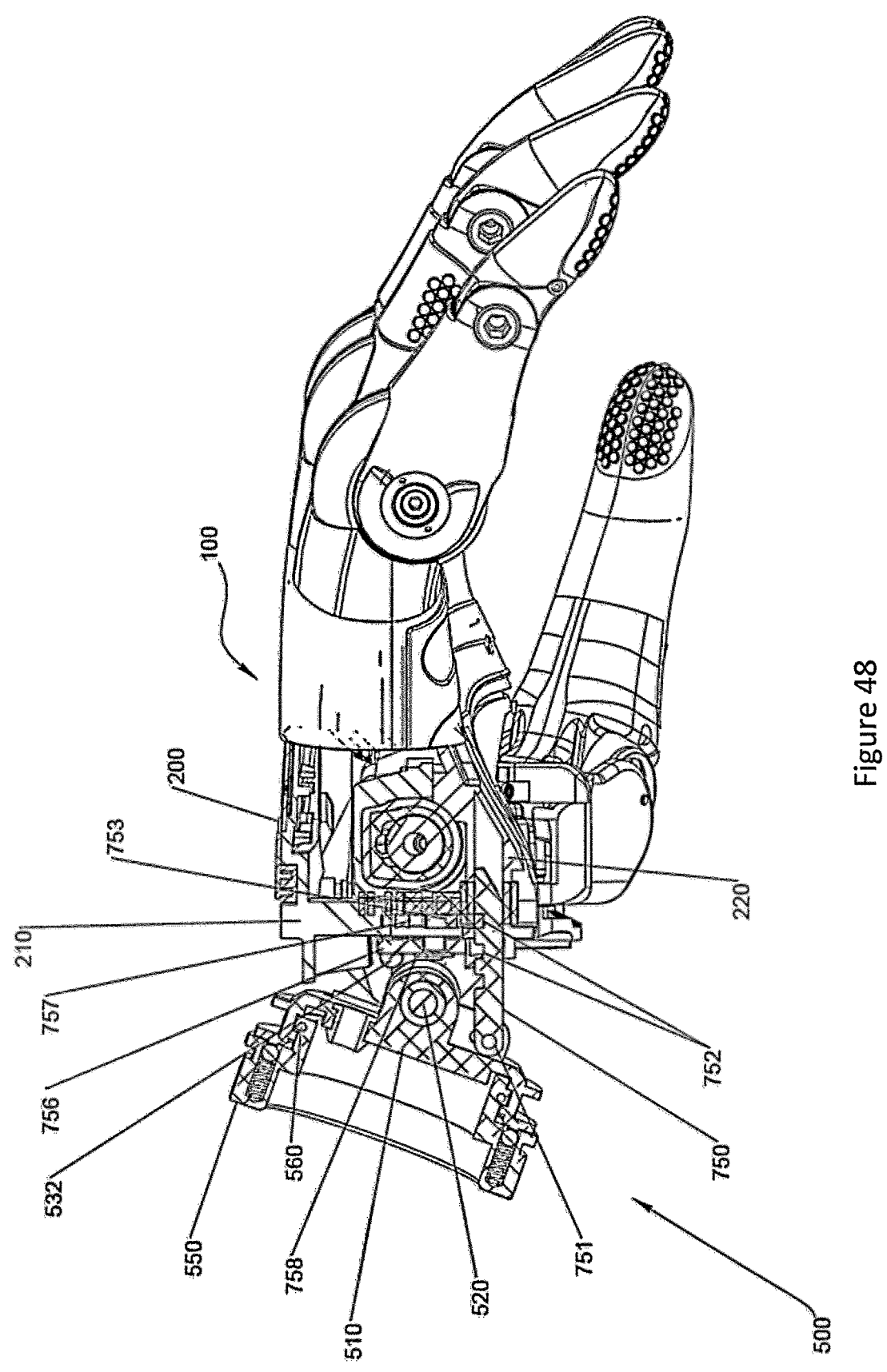
FIG. 48 is a sectional view along line H-H of FIG. 47.
Figure 49:
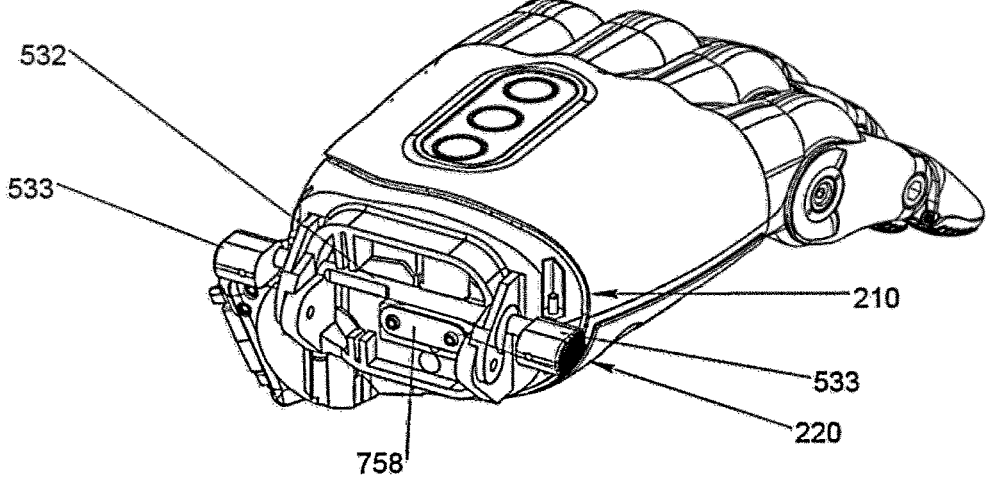
FIG. 49 is a perspective view of the back of the automated hand of FIG. 43 without the wrist portion.
Figure 50:
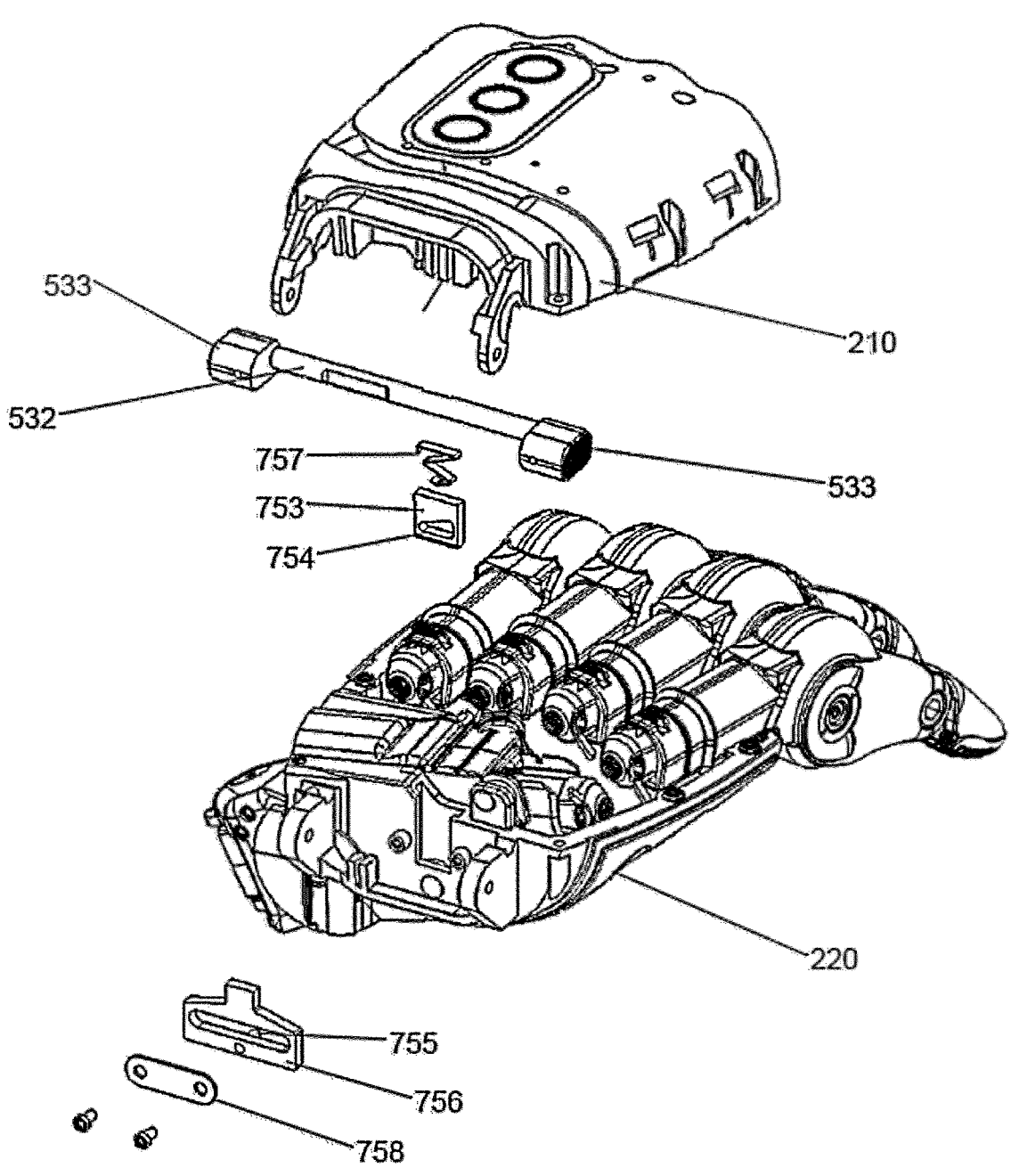
FIG. 50 is an exploded perspective view of FIG. 49.
Figure 51:
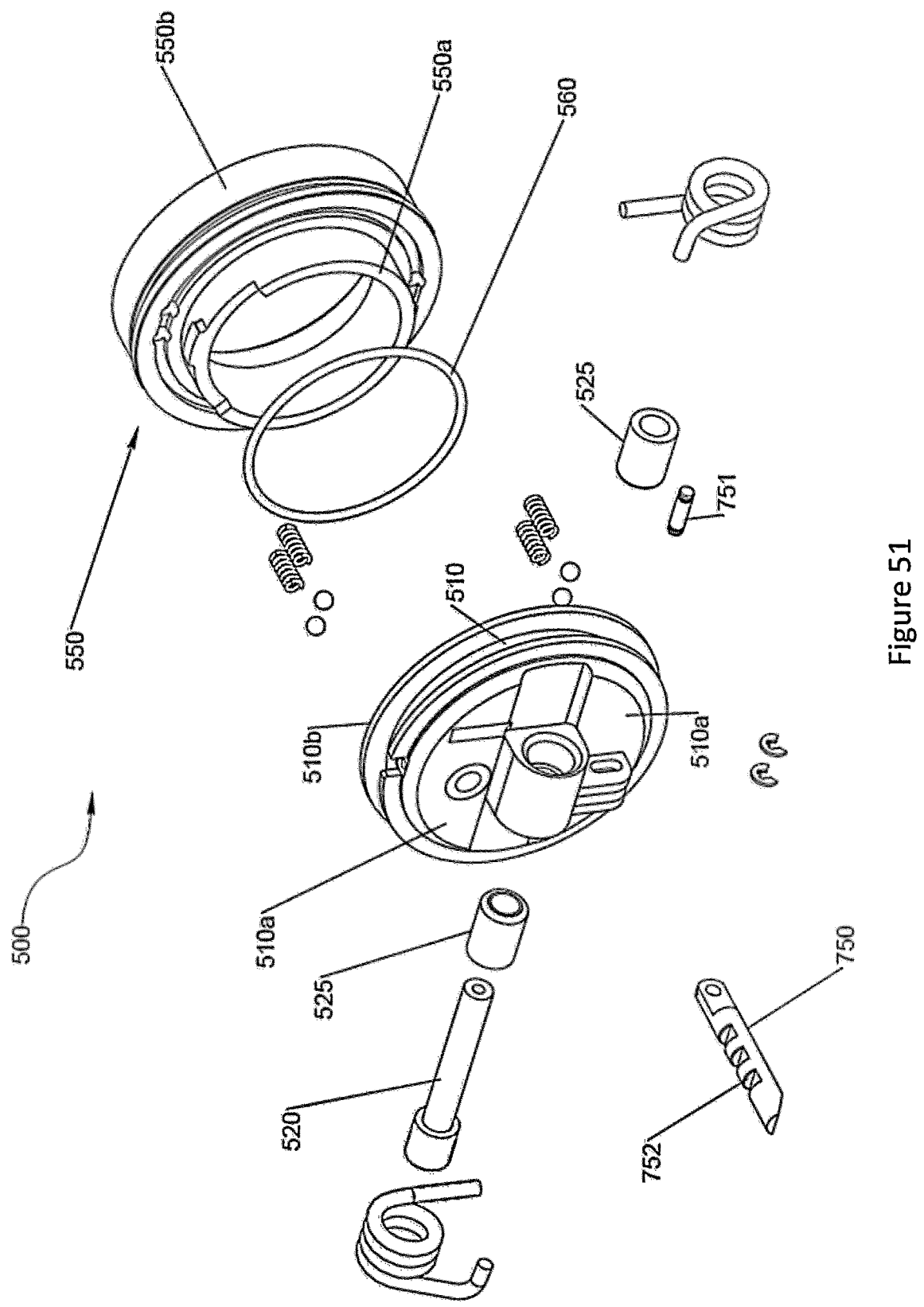
FIG. 51 is an exploded perspective of the wrist for the hand shown in FIG. 43.
Figure 52:
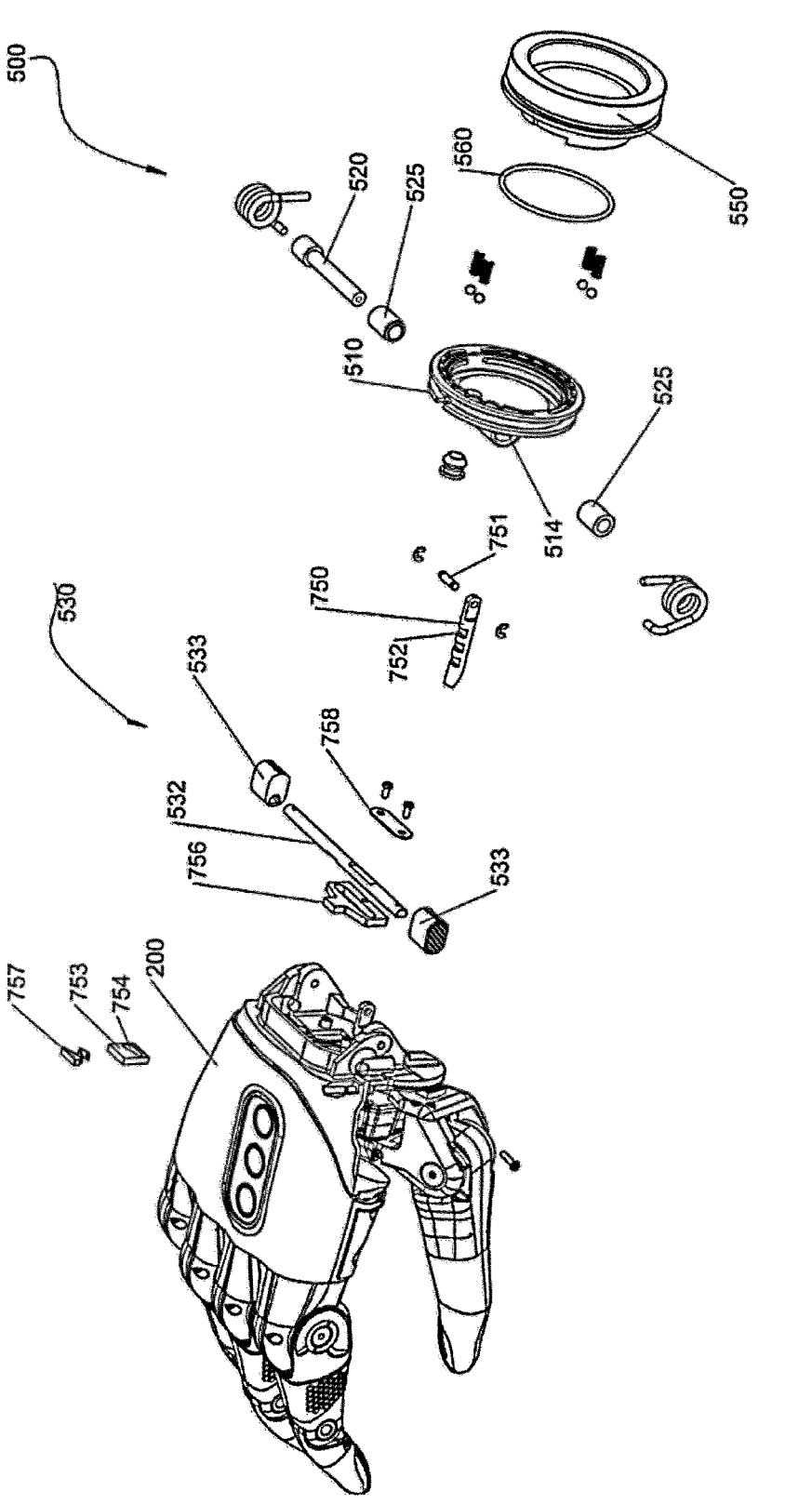
FIG. 52 is an exploded view of the complete rear assembly of the hand shown in FIG. 43.
Figure 53:
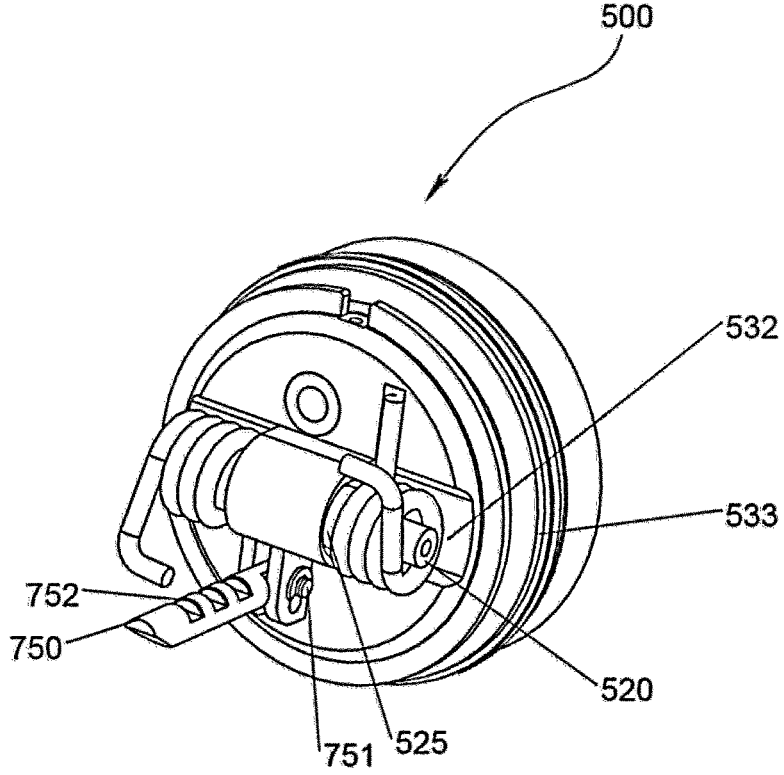
FIG. 53 is a perspective of the wrist shown in FIG. 51.

Referring now to FIGS. 43 to 53 and 55 to 56 an alternate wrist design is shown. Hand 100 is pivotally mounted to wrist 500 via axle 520. In this embodiment the wrist locking mechanism is in the form of a rod 750 pivotally mounted to wrist 500 via pin 751. Rod 750 has a number of notches 752 along its length spaced at suitable intervals to define a range of useful wrist rotations. The locking mechanism includes a locking element 753 having a diverging aperture 754. Locking element 753 is biased towards rod 750 by biasing spring 757. Pin 755 projecting from plate 756 engages within diverging aperture 754. When a stopper 533 is pushed to move sliding arm 532 to the right pin 751 is positioned at the left of diverging aperture 754 and restricts locking element 753 from being forced down to engage with a notch 752. When a stopper 533 is pushed to move sliding arm 532 to the left pin 751 is positioned at the right of diverging aperture 754 and allows locking element 753 to be forced down to engage with a notch 752 by spring 757 (if locking element 753 is not positioned adjacent a notch it will remain biased against rod 750 until aligned with a notch-at which point it will lock the wrist). FIG. 44 shows the wrist locked in a neutral position. FIG. 46 shows the wrist locked in flexion. FIG. 48 shows the wrist locked in extension.

Figure 55:
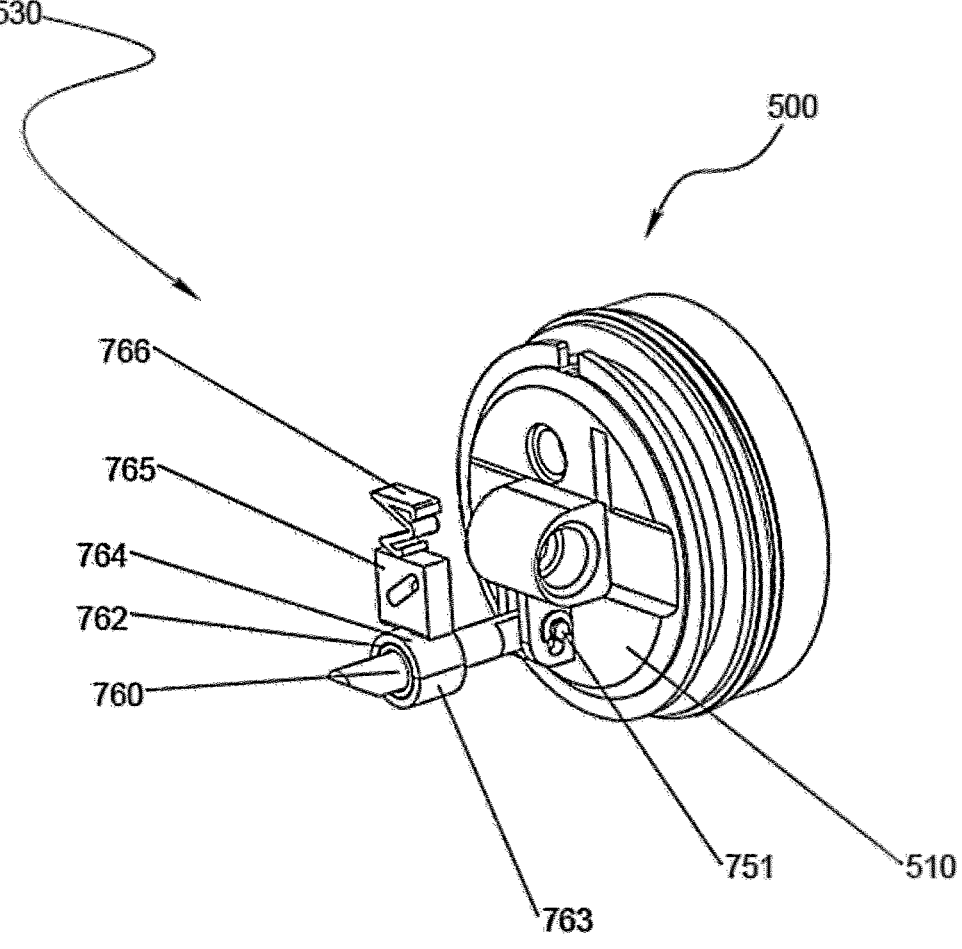
FIG. 55 is a perspective of yet another wrist embodiment.
Figure 56:
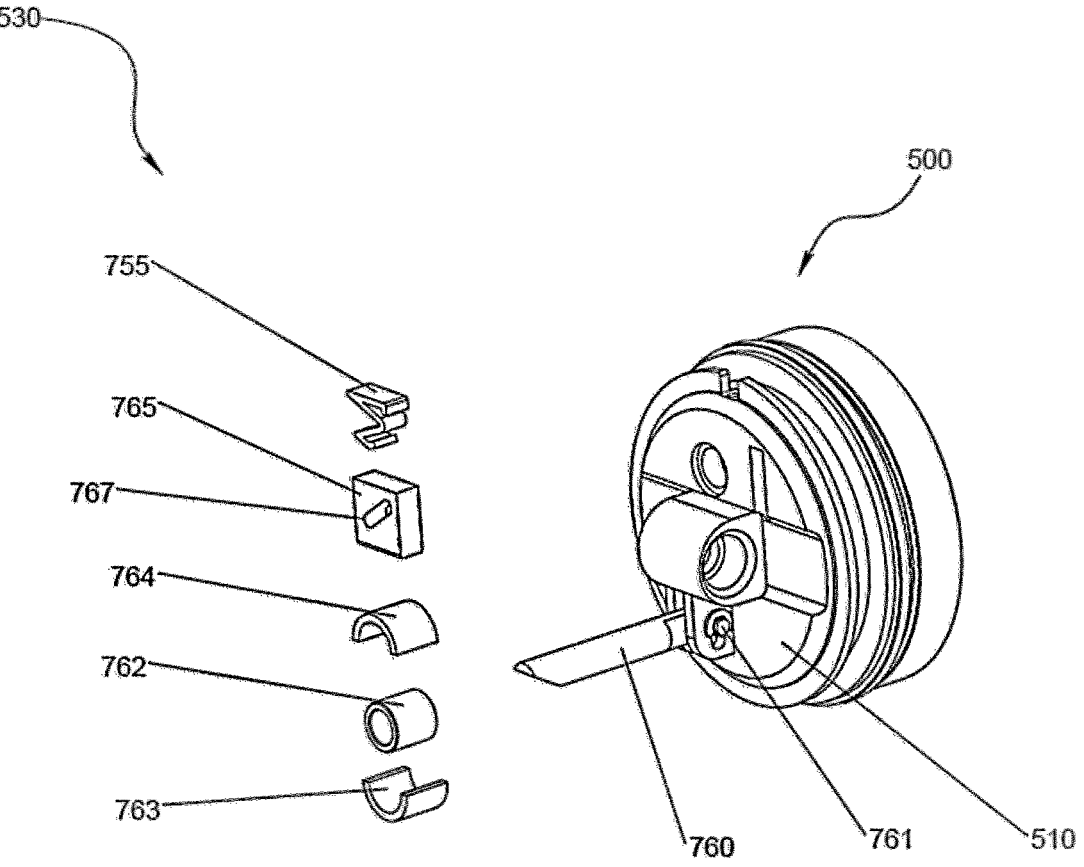
FIG. 56 is an exploded perspective view of the wrist embodiment shown in FIG. 55.
Figures 57, 58, 59:
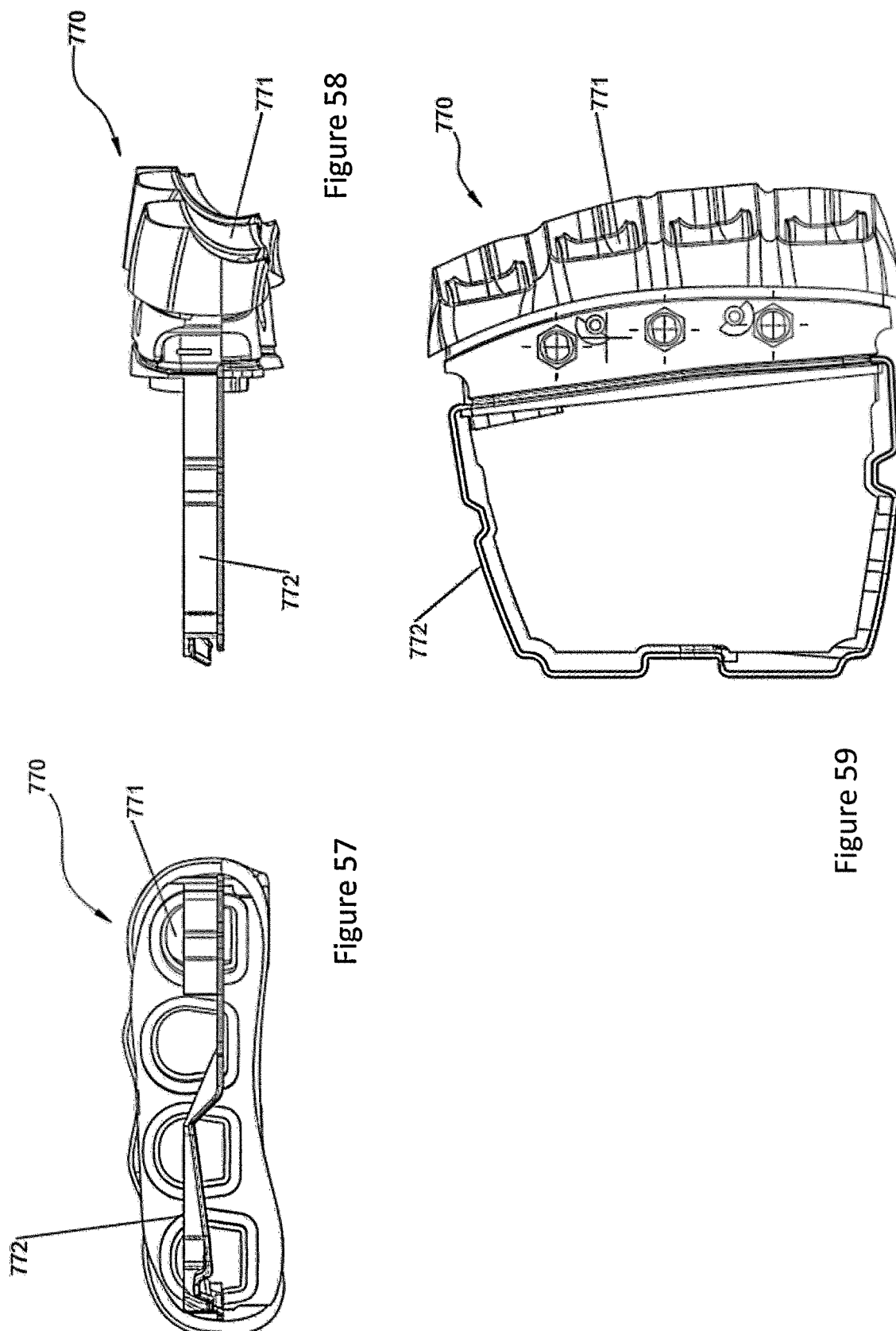
FIG. 57 is a back elevation of a Metacarpal brace according to a further embodiment.
FIG. 58 is a side elevation of the Metacarpal brace shown in FIG. 57.
FIG. 59 is a plan view of the Metacarpal brace shown in FIG. 57.
Figure 60:
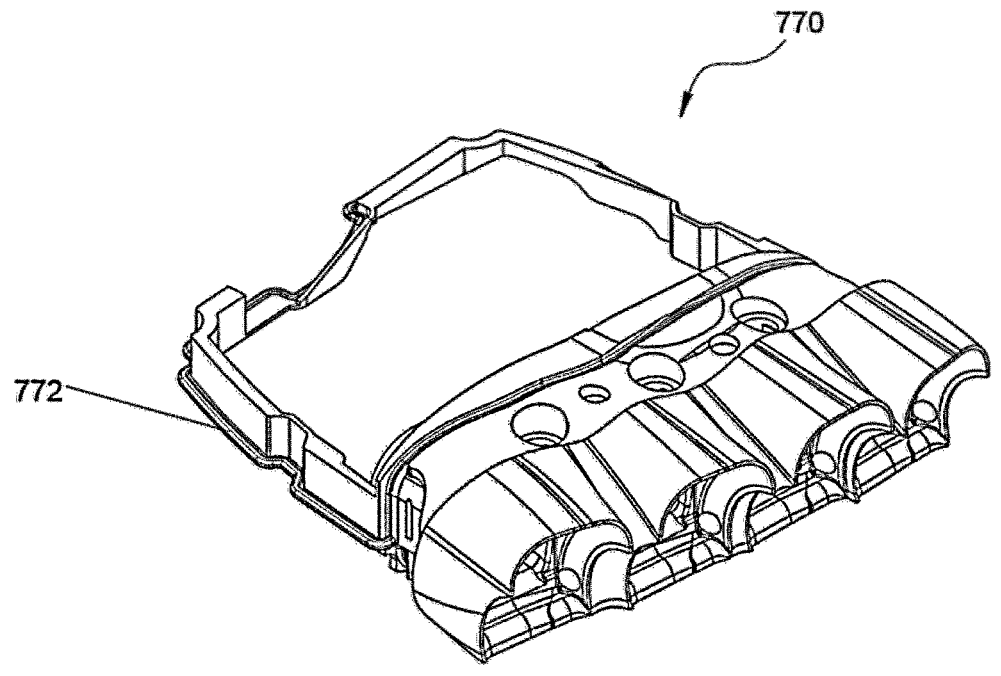
FIG. 60 is a front perspective view of the Metacarpal brace shown in FIG. 57.

Whilst in the above embodiment a variable length linkage is provided having a number of discrete positions a continuously variable linkage may also be provided with variations as shown in FIGS. 55 and 56. In this case a rod 760 is pivotally connected to wrist 500. A collar 762 formed of a resilient material is surrounded by metal half collars 763 and 764. When a stopper 533 is pushed to move sliding arm 532 to the right pin 751 is positioned at the left of angled aperture 767 and raises locking element 765. When a stopper 533 is pushed to move sliding arm 532 to the left pin 751 is positioned at the right of angled aperture 767 and forced locking element 765 to be forced down against half collar 764 which compresses resilient collar 762 and locks the position of rod 760 to lock the wrist.

By locating the locking mechanism within the palm of the hand the wrist can be of a very short and compact design. Its light and compact design enables a natural looking and functioning wrist. The compact design provides space for other components in the wrist area helping to reduce overall size of the hand and allow a fluid compatible design.

Submersible

Figure 61:
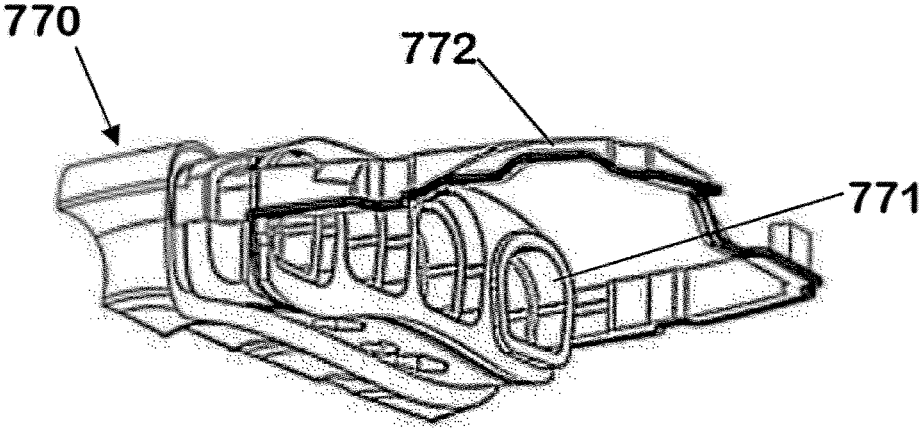
FIG. 61 is a rear perspective view of the Metacarpal brace shown in FIG. 57.
Figure 62:
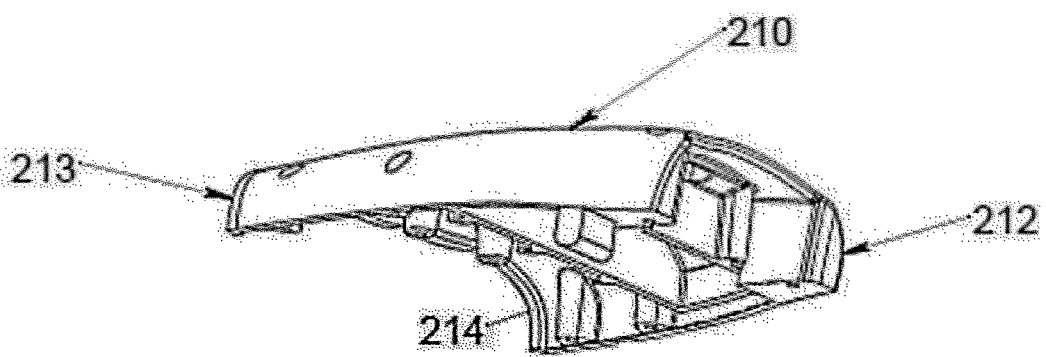
FIG. 62 is a rear perspective view of a top palm.
Figure 63:
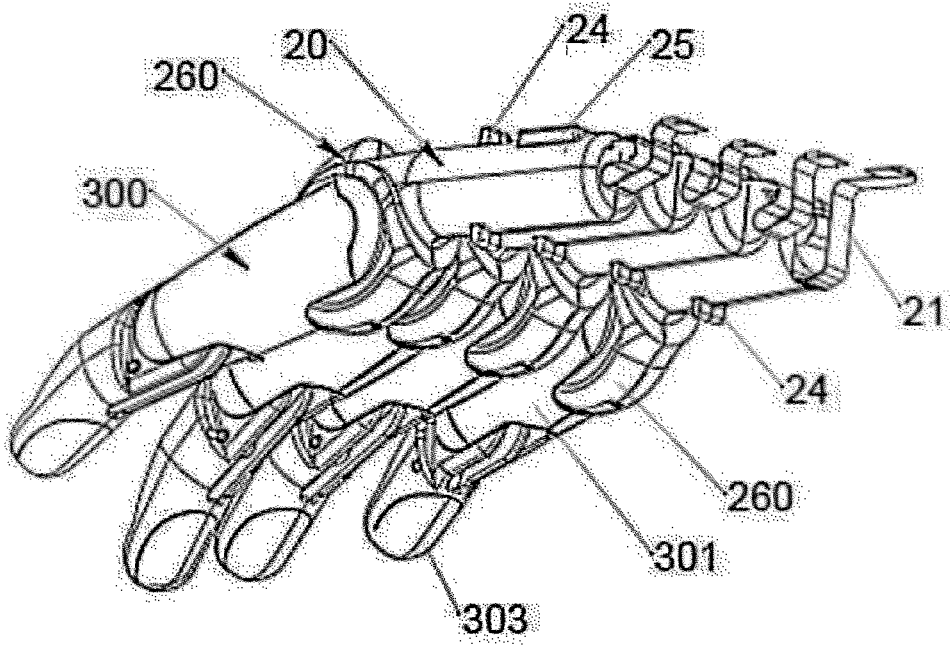
FIG. 63 is a rear perspective view of a set of digits and actuators.
Figure 64:
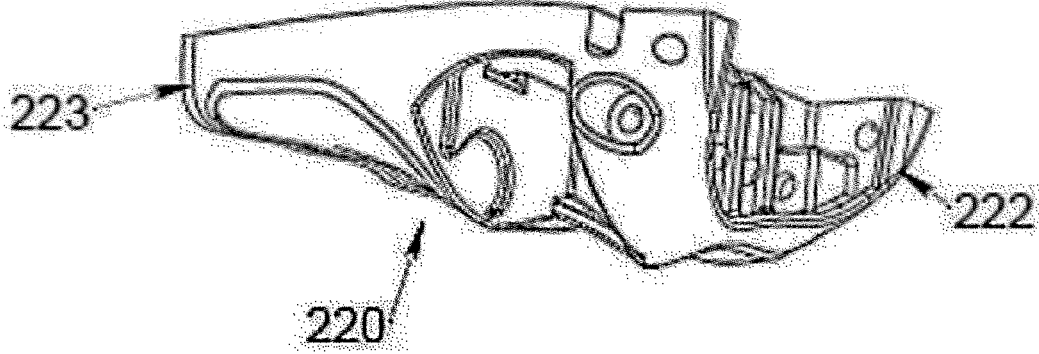
FIG. 64 is a rear perspective view of a bottom palm.

Referring now to FIGS. 57 to 64 features of design of the palm and metacarpal block enabling the automated hand to be submersible in fluid will be described. As shown in FIGS. 61, 62 and 64 the palm consists of an upper part 210, a lower part 220 and a metacarpal brace 770. In this embodiment non-circular keyhole shaped apertures 771 are provided in the metacarpal brace to mate with correspondingly shaped actuator housings to prevent rotation. A seal in the form of an O ring 772 is provided about the periphery of metacarpal block 770 to form a water tight seal with lower palm part 220 when the parts are secured together. As the actuators 20 tightly engage with resilient metacarpal block 770 a fluid tight seal is formed at this interface. The knuckle joints are of a fluid tight construction to prevent water ingress via the knuckle joints. In this way a sealed palm region (all or part) may be provided to house the motors and electronics in an area that is waterproof when submerged in fluid. This allows water ingress in other areas without impacting the functionality of the hand.

By providing a sealed palm region and sealing critical components within liquid can enter the rest of the hand making it submersible and fluid compatible without the use of a glove.

Removable Plates

Figure 65:
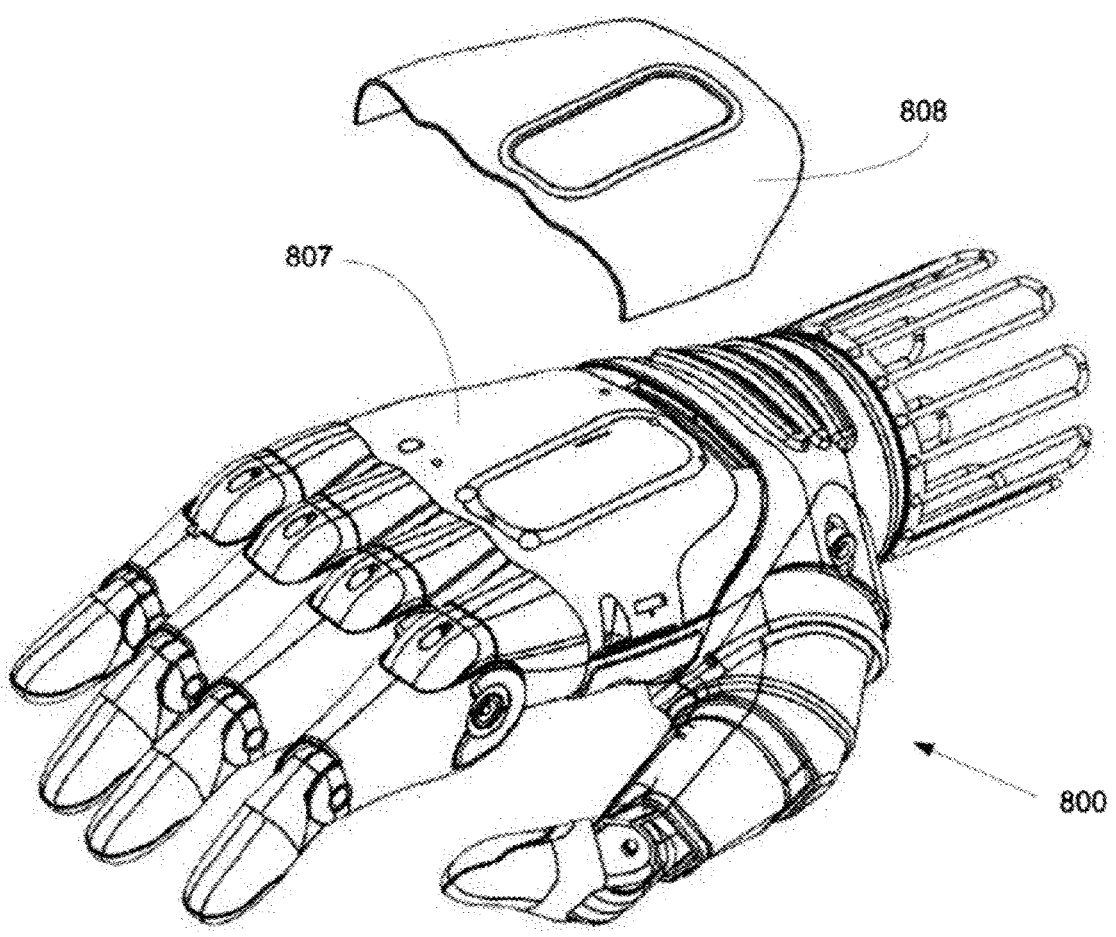
FIG. 65 is an exploded perspective view of hand and top palm cover.
Figure 66:
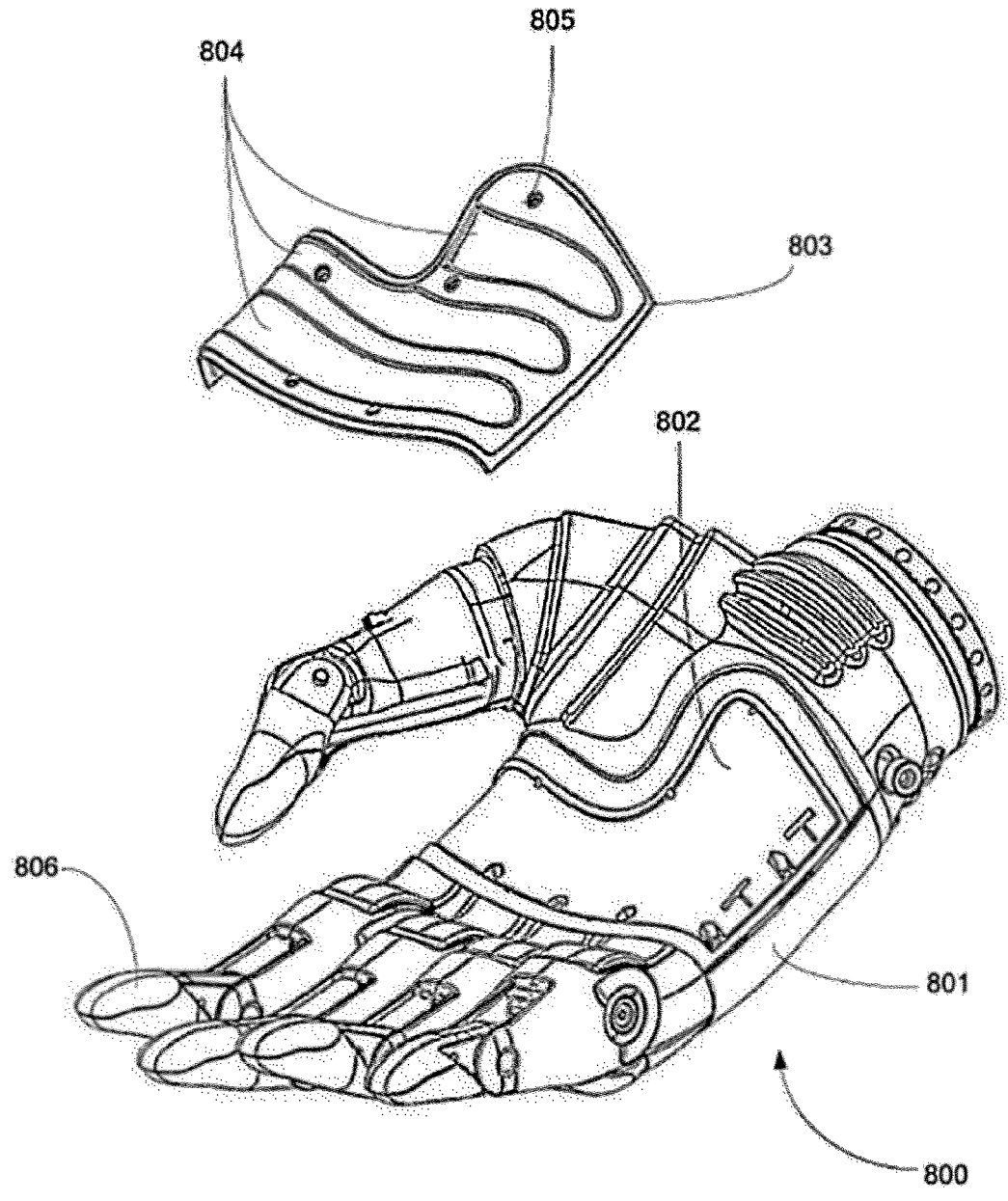
FIG. 66 is an exploded perspective view of hand and bottom palm cover.

Referring now to FIGS. 65 and 66 embodiments including removable plates are shown. The hand 800 shown in FIG. 65 includes a cavity 802 in the lower part of the submersible palm dimensioned to receive a plate 803. Apertures 805 are provided in plate 803 to allow it to be secured to palm 801 via suitable fasteners such as screws. The plate 803 may be formed of a rigid material with sections 804 of softer material provided on the surface of plate 803. The softer material may have a Shore A hardness of between 15 and 90, preferably 50 to 90, with a Shore A hardness of about 60 being found very effective. Sections 804 of softer material may be formed by over-molding or may be affixed thereto etc. These softer sections provide enhanced grip but as they are softer they are prone to wear and it is convenient to provide replaceable plates. FIG. 65 shows a replaceable plate 808 that may be secured into cavity 807 in the upper part of a palm. As well as providing replaceable palm plates fingertips 806 of digits may also be provided with a soft material layer to improve grip in a similar manner and these may be replaceable too. Due to the submersible nature of the palm the plates may simply be affixed without needing to make any watertight seal between the plate and the palm.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

For example, the invention(s) may also be used in relation to other automated and/or prosthetic limbs, such as a foot.

The invention claimed is:

1. An automated prosthetic hand comprising:

a palm comprising a display and an outer shell, the outer shell forming an upper part of the palm and a lower part of the palm, wherein the display is on the upper part of the palm;

two or more digits extending from the palm;

one or more actuators configured to cause at least one of the two or more digits to move; and a control system connected to the one or more actuators and configured to:

receive one or more electromyography (EMG) signals; and indicate on the display that the one or more EMG signals have been received, wherein the two or more digits are mounted to the palm by a mounting arrangement that allows lateral movement of the two or more digits, wherein the mounting arrangement comprises a material having a DMTA damping factor between 0.05 and 0.8 over a temperature range of −20° C. to 100° C.

2. The automated prosthetic hand of claim 1, wherein the control system is further configured to indicate, on the display, an attribute of the one or more EMG signals received, wherein the attribute is strength of the one or more EMG signals received.

3. The automated prosthetic hand of claim 1, wherein the display comprises one or more lights, wherein the one or more lights comprise one or more light-emitting diodes (LEDs).

4. The automated prosthetic hand of claim 1, wherein the display comprises an alphanumeric display.

5. The automated prosthetic hand of claim 1, wherein the control system is further configured to cause the two or more digits to assume a grip pattern depending on the one or more EMG signals received.

6. The automated prosthetic hand of claim 1, wherein the automated prosthetic hand comprises a user interface and the control system is configured to cause the two or more digits to assume a grip pattern depending on one or more signals received from the user interface.

7. The automated prosthetic hand of claim 6, wherein the user interface comprises one or more buttons.

8. The automated prosthetic hand of claim 7, wherein the one or more buttons are located in the same areas as one or more lights, wherein the one or more buttons have one or more lights thereon.

9. The automated prosthetic hand of claim 1, wherein the control system receives the one or more EMG signals from a user.

10. The automated prosthetic hand of claim 1 wherein the display is on a panel on the outer shell, wherein the panel is sealed.

11. An automated prosthetic hand comprising:

a palm comprising a display and an outer shell, wherein the display is on the outer shell;

two or more digits extending from the palm;

one or more actuators configured to cause at least one of the two or more digits to move; and a control system connected to the one or more actuators and configured to:

receive one or more electromyography (EMG) signals and/or one or more signals from a user interface located on the automated prosthetic hand;

cause the two or more digits to assume a predetermined grip pattern depending on the one or more EMG signals and/or the one or more signals from the user interface; and indicate the predetermined grip pattern on the display, wherein the two or more digits are each mounted to the palm by an articulated joint in a knuckle region of the automated prosthetic hand;

and wherein the knuckle region comprises a material having a DMTA damping factor between 0.05 and 0.8 over a temperature range of −20° C. to 100° C.

12. The automated prosthetic hand of claim 11, wherein the display is an alphanumeric display.

13. The automated prosthetic hand of claim 12, wherein the automated prosthetic hand comprises the user interface and the user interface comprises one or more depressible buttons, wherein the outer shell forms an upper part of the palm and a lower part of the palm, wherein the user interface and the alphanumeric display are located on the outer shell at the upper part of the palm, and wherein the user interface is spaced apart from the alphanumeric display such that there is a portion of the outer shell between the user interface and the alphanumeric display.

14. The automated prosthetic hand of claim 11, wherein the automated prosthetic hand comprises the user interface and the control system is configured to receive both the one or more EMG signals and the one or more signals from the user interface.

15. The automated prosthetic hand of claim 14, wherein the control system is configured to select the predetermined grip pattern for the two or more digits to assume based on both the one or more EMG signals and the one or more signals from the user interface.

16. The automated prosthetic hand of claim 11, wherein the control system receives the one or more EMG signals from a user.

17. An automated prosthetic hand comprising:

a palm;

two or more digits extending from the palm;

one or more actuators configured to cause at least one of the two or more digits to move;

a control system in the palm, the control system configured to control the one or more actuators; and a user interface on the palm;

wherein the user interface comprises one or more depressible buttons having one or more lights thereon, wherein the automated prosthetic hand further comprises wired electrical connectors within the palm, the wired electrical connectors connecting one or more depressible buttons to the control system, and wherein the two or more digits are mounted to the palm by a mounting arrangement that allows lateral movement of the two or more digits, wherein the mounting arrangement comprises a material having a DMTA damping factor between 0.05 and 0.8 over a temperature range of −20° C. to 100° C.

18. The automated prosthetic hand of claim 17, wherein the one or more lights comprise one or more light-emitting diodes (LEDs).

19. The automated prosthetic hand of claim 17, wherein the automated prosthetic hand is configured to cause the two or more digits to assume a grip pattern depending on one or more signals received from the user interface.

20. The automated prosthetic hand of claim 17, wherein the automated prosthetic hand is further configured to cause the two or more digits to assume a grip pattern depending on one or more electromyography (EMG) signals.

21. The automated prosthetic hand of claim 20, wherein the automated prosthetic hand is configured to cause one or more lights to indicate that the one or more EMG signals have been received.

22. The automated prosthetic hand of claim 21, wherein the automated prosthetic hand is configured to cause the one or more lights to indicate strength of the one or more EMG signals received.

23. The automated prosthetic hand of claim 17 wherein the one or more lights is/are configured to flash in different patterns for different grips.

24. The automated prosthetic hand of claim 17 wherein the one or more depressible buttons comprise a plurality of depressible buttons and the one or more lights comprise a plurality of lights of varying colours.

25. The automated prosthetic hand of claim 17 wherein the one or more actuators comprise a plurality of actuators, one for each of the digits, wherein the actuators are individually sealed within the digits.

\* \* \* \* \*